United States Patent [19]
Graham et al.

[11] Patent Number: 6,066,503
[45] Date of Patent: May 23, 2000

[54] RECOMBINANT DNA MOLECULES ENCODING AMINOPEPTIDASE ENZYMES AND THEIR USE IN THE PREPARATION OF VACCINES AGAINST HELMINTH INFECTIONS

[75] Inventors: Margaret Graham; Trevor Stanley Smith, both of Linton; Edward Albert Munn, Fulbourn; David Patrick Knox, Cockenzie; Joanna Jane Oliver, Edinburgh, all of United Kingdom; Susan Elizabeth Newton, Strathmore, Australia

[73] Assignee: Barbraham Institute, Cambridge, United Kingdom

[21] Appl. No.: 08/335,844

[22] PCT Filed: May 7, 1993

[86] PCT No.: PCT/GB93/00943

§ 371 Date: Jan. 9, 1995

§ 102(e) Date: Jan. 9, 1995

[87] PCT Pub. No.: WO93/23542

PCT Pub. Date: Nov. 25, 1993

[30] Foreign Application Priority Data

May 8, 1992 [GB] United Kingdom .................... 9209993

[51] Int. Cl.$^7$ ........................... C12N 15/30; C12N 15/52; C12N 15/57; A61K 39/00
[52] U.S. Cl. ........................ 435/693; 435/69.1; 435/325; 435/69.7; 435/212; 435/362; 435/252.3; 435/320.1; 435/365; 435/367; 435/252.33; 435/254.11; 435/183; 536/23.1; 536/23.2; 536/23.4; 536/23.5; 424/184.1; 424/94.1; 424/265.1; 424/199.1; 530/300; 530/350; 530/388.6; 930/240
[58] Field of Search .............................. 424/94.1, 265.1, 424/199.1, 184.1; 435/252.3, 212, 183, 320.1, 69.1, 69.7, 69.3, 325, 362, 365, 367, 252.33, 254.11; 530/388.6, 350, 300; 536/23.1, 23.5, 23.2, 23.4; 930/240

[56] References Cited

U.S. PATENT DOCUMENTS 4,879,213  11/1989  Fox et al. .

FOREIGN PATENT DOCUMENTS

| WO 00835 | 2/1988 | WIPO . |
| 9011086 | 4/1990 | WIPO . |
| 9003433 | 5/1990 | WIPO . |

OTHER PUBLICATIONS

Lehniger "Biochemistry" 2nd ed. Worth Publishers, p. 63.

Burgress et al. J. Cell Biol. (1990) vol. 111, 2129–2138.

Lazar et al. (1988) Mol. and Cell. Biol. vol. 8(3), 1247–1252.

Olsen et al., (1988) FEBS Lett. vol. 238(2), 307–314.

Look et al. (1989) J. Clin. Invest. vol. 83(4), 1299–1307.

Watt et al., "Amino Acid Sequence Deduced from a Rat Kidney cDNA Suggests It Encodes the Zn–peptidase Aminopeptidase N*", Journal of Biol. Chem., vol. 264, No. 10, pp. 5480–5487, Apr. 5, 1989.

Wu et al., "Molecular cloning of the murine BP–1/6C3 antigen: A member of the zinc–dependent metallopeptidase family", Proc. Natl., Acad. Sci. USA, vol. 87, pp. 993–997, Feb. 1990 (Immunology).

*Primary Examiner*—Anthony C. Caputa
*Assistant Examiner*—Khalid Masood
*Attorney, Agent, or Firm*—Rothwell, Figg, Ernst & Kurz

[57] ABSTRACT

The present invention provides nucleic acid molecules containing nucleotide sequences encoding helminth aminopeptidase enzymes, and antigenic fragments and functionally-equivalent variants thereof, their use in the preparation of vaccines for use against helminth parasites, and synthetic polypeptides encoded by them.

6 Claims, 42 Drawing Sheets

|        | 1                                                          | 50 |
|--------|------------------------------------------------------------|----|
| H11-3  | GGTTTAATTA CCCAAGTTTG AGGGTCTCCA TCTAG..... ..........A    |    |
| H11-2  | GGTTTAATTA CCCAAGTTTG AG........ ............ ..........A  |    |
| H11-1  | GGTTTAATTA CCCAAGTTTG AGATGACAGC AGAGGAGAGT CAGGAGCAGG     |    |

|        | 51                                                         | 100 |
|--------|------------------------------------------------------------|-----|
| H11-3  | TGACGTCGCA GGGGAGAACG CGGACATTGC TGAATCTAAC TCCAATCCGT     |     |
| H11-2  | TGACGGCGGA GTGGCAGAAG CGTCGAATCT TGGGCTTCTC ACCTATCAGC     |     |
| H11-1  | AGACGCAGCA ACCACGAAAA AATACAGTGC TACGGCTCAC CCCAATCAAG     |     |

|        | 101                                                        | 150 |
|--------|------------------------------------------------------------|-----|
| H11-3  | CTTATTGTCG CATTATTTCT AGTAGCTGCT GCAGTCGGCC TCTCTATTGG     |     |
| H11-2  | CTACTTTGTA CATTATTTGT ATTAGCTGCT GCCGTTGGAC TCTCCATTGG     |     |
| H11-1  | TCTCTCTTTG CTTTGTTAGT GGTAGCTGCT GCCGTCGGCC TCTCAATCGG     |     |

|        | 151                                                        | 200 |
|--------|------------------------------------------------------------|-----|
| H11-3  | TCTCACCTAT TACTTTACTC GCAAAGCGTT CGATACCTCA GAAAAGCCAG     |     |
| H11-2  | TCTTACCTAT TACTTCACTC GTAAAGCATT CGATACCACA CAAAAGAAC      |     |
| H11-1  | TCTCACCTAT TACTTTACAA GGAAAGCTTT TGATACTACT GGCGGAAATG     |     |

|        | 201                                                        | 250 |
|--------|------------------------------------------------------------|-----|
| H11-3  | GGAAGGATGA TACTGGTGGC AAGGACAAAG ACAATTCTCC CTCTGCGGCG     |     |
| H11-2  | AGAAGGATGA CAGTGGTGGT AAAGAAAAGG ATAATTCTCC TTCTGCAGAA     |     |
| H11-1  | GAAAAGGGGA TCAACCTATT GTCGAT...G ATAATTCCCC ATCAGCTGAA     |     |

|        | 251                                                        | 300 |
|--------|------------------------------------------------------------|-----|
| H11-3  | GAACTACTCC TTCCAAGTAA TATAAAACCA TTGTCTTACG ACTTGACGAT     |     |
| H11-2  | GAACTACTTC TTCCAACGAA CATAAAACCA GTCTCGTACG ACTTGAACAT     |     |
| H11-1  | GAATTACGTC TCCCAACAAC CATAAAACCT TTGACATACG ACTTAGTAAT     |     |

|        | 301                                                        | 350 |
|--------|------------------------------------------------------------|-----|
| H11-3  | CAAAACATAT CTACCTGGTT ATGTGGACTT CCCACCGGAG AAAAACCTCA     |     |
| H11-2  | CAAAACATAT CTACCGGGTT ACGTGAACTT TCCACCAGAA AAGAATCTCA     |     |
| H11-1  | CAAAACGTAT CTGCCAAACT ATGTAAACTA TCCACCTGAG AAAGATTTCG     |     |

|        | 351                                                        | 400 |
|--------|------------------------------------------------------------|-----|
| H11-3  | CATTCGATGG GCGTGTGGAA ATATCAATGG TTGTAATTGA GCCAACAAAG     |     |
| H11-2  | CATTTGATGC CCATGTGGAG ATTGCTATGG TTGTGGTTGA GCCTACAAAT     |     |
| H11-1  | CTATTGATGG GACTGTGGTG ATTGCTATGG AAGTTGTGGA GCCAACAAAG     |     |

|        | 401                                                        | 450 |
|--------|------------------------------------------------------------|-----|
| H11-3  | AGTATCGTAC TCAATTCAAA GAAGATCTCT GTAATACCCC AAGAATGTGA     |     |
| H11-2  | AGTATTGTGC TGAACTCGAA GAAAATCACT TTGGCACAAG GAGGATGCGA     |     |
| H11-1  | TCTATTGTGC TCAACTCGAA AAATATTCCT GTAATTGCAG ACCAGTGCGA     |     |

|        | 451                                                        | 500 |
|--------|------------------------------------------------------------|-----|
| H11-3  | ACTGGTATCG GGCGATAAAA AACTCGAAAT TGAAAGTGTA AAGGAGCACC     |     |
| H11-2  | ACTGTTCTCA GGTAATCAGA AACTTGACAT CGAAAGTGTA AAGATGCAGG     |     |
| H11-1  | ACTGTTTTCT AACAACCAAA AACTCGACAT CGAAAAGGTT GTGGATCAGC     |     |

|        | 501                                                        | 550 |
|--------|------------------------------------------------------------|-----|
| H11-3  | CAAGACTGGA AAAGGTTGAG TTTCTTATCA AAAGCCAACT GGAAAAAGAT     |     |
| H11-2  | AAAGACTTGA CAAGCTTGAG ATTACCCTCA AAAATCAGCT GCAAAAAGAT     |     |
| H11-1  | CAAGGCTGGA GAAAGTCGAA TTCGTTTTGA AGAAAAAGCT GGAGAAGAAT     |     |

|        | 551                                                        | 600 |
|--------|------------------------------------------------------------|-----|
| H11-3  | CAACAAATCT TGCTCAAGGT CGGCTACATC GGTCTCATCA GCAACAGCTT     |     |
| H11-2  | CTGAAAATCC TGCTCAAGAT CACTTACACC GGCCTTATTA GCGACACTCT     |     |

FIG. 2

```
H11-1    CAGAAAATCA CGCTCAAGAT TGTATACATT GGCCTTATCA ACGACATGCT 601                                                   650
H11-3    TGGTGGAATC TACCAGACCA CTTATACCAC CCCGGATGGC ACCCCTAAGA
H11-2    CGGTGGGCTC TACCAGTCCA TCTACACTGA TAAGGACGGA AAAACTAAGA
H11-1    TGGAGGACTT TATCGAACAA CCTACACGGA TAAAGATGGT ACAACCAAGA 651                                                   700
H11-3    TCGCTGCAGT TTCACAAAAT GAGCCCATAG ATGCTCGTCG AATGGTACCA
H11-2    TCGTTGCTGT TTCACAAAAT GAACCATCAG ACGCTCGTCG TATAGCGCCA
H11-1    TTGCTGCATG CACTCATATG GAACCGACGG ACGCCCGTCT TATGGTCCCC 701                                                   750
H11-3    TGCATGGATG AACCGAAATA CAAAGCAAAC TGGACCGTTA CTGTCATTCA
H11-2    TGCTTTGACG AACCGAAGTA CAAGGCAACA TGGACTGTCA CCGTCGTTCA
H11-1    TGTTTCGACG AGCCGACGTT TAAGGCAAAC TGGACTGTGA CTGTGATTCA 751                                                   800
H11-3    TCCAAAAGGC ACCAAAGCCG TCTCGAATGG AATCGAAGTG AACGGAGATG
H11-2    TCCCAAAGGT ACAAAGGCTG CATCGAACGG CATTGAAGCA AATGGAAAAG
H11-1    TCCGAAGGGC ACCAGTGCCG TGTCGAATGG AATAGAA... AAGGGAGAAG 801                                                   850
H11-3    GAGAGATCAG TGGTGATTGG ATCACATCGA AGTTCTTGAC TACTCCACGG
H11-2    GGGAGCTCAA GGGTGATTGG ATAACGTCTA AATTTAAAAC TACCCCACCG
H11-1    GAGAAGTCTC TGGCGATTGG GTCACAACCA GATTCGATCC AACCCCGCGA 851                                                   900
H11-3    ATGTCATCCT ACTTGTTGGC AGTTATGGTT TCAGAATTTG AATACATCGA
H11-2    ATGTCGTCCT ATTTATTGGC TATTATTGTT TGTGAATTTG AATACATTGA
H11-1    ATGCCTTCGT ATTTGATTGC TCTTGTGATT TCCGAATTTA AGTACATTGA 901                                                   950
H11-3    AGGTGAAACA AAGACGGGTG TTCGGTTCCG TATATGGTCA CGCCCAGAGG
H11-2    AGGATTTACA AAAACGGGTG TTCGGTTCCG TATATGGTCT CGACCAGAGG
H11-1    AAATTATACG AAAAGCGGTG TTCGATTCCG AATTCCGGCT CGTCCGGAAG 951                                                   1000
H11-3    CAAAGAAGAT GACACAATAT GCTCTGCAAT CTGGTATCAA GTGCATAGAA
H11-2    CGAAACGAAT GACGGCATAC GCTTTGGATG CTGGCATCAG ATGCCTGGAG
H11-1    CTATGAAGAT GACAGAATAT GCCATGATAG CTGGAATCAA ATGTTTGGAT 1001                                                  1050
H11-3    TTCTACGAAG ATTTCTTTGA TATCAGATTC CCTCTGAAGA AACAAGATAT
H11-2    TTCTATGAGA AGTTCTTTGA CATAAAATTC CCTCTGGAAA AACAAGATAT
H11-1    TACTATGAGG ACTTCTTCGG GATCAAATTC CCACTTCCAA AACAAGATAT 1051                                                  1100
H11-3    GATTGCCCTT CCTGATTTCT CTGCCGGTGC CATGGAGAAT TGGGGCCTCA
H11-2    GATTGCTCTT CCTGATTTCA CCGCTGGTGC CATGGAAAAC TGGGGCCTTA
H11-1    GGTTGCTCTT CCTGACTTCT CATCTGGTGC TATGGAGAAC TGGGGTCTCA 1101                                                  1150
H11-3    TCACTTACAG GGAAAACTCT TTGTTGTACG ATGACAGATT CTATGCACCG
H11-2    TCACTTATAG AGAGGATTCT CTCCTATACG ATGAAAAAAT TTATGCACCG
H11-1    TCACATACAG GGAGGGTTCC GTGCTCTACG ATGAAAACCT CTACGGACCA 1151                                                  1200
```

FIG. 2 (contd)

```
                1150
H11-3   ATGAATAAAC AGCGAATTGC TCGCATTGTT GCTCATGAGC TTGCTCATCA
H11-2   ATGAATAAAC AGCGGGTTGC TCTCGTAGTT GCTCACGAGC TTGCTCATCA
H11-1   ATGAATAAGG AGCGGGTTGC AGAAGTGATC GCGCACGAAC TTGCACATCA 1201                                           1250
H11-3   GTGGTTCGGC GACTTGGTTA CGATGAAGTG GTGGGATAAT TTGTGGTTGA
H11-2   GTGGTTCGGC AATCTGGTCA CACTGAAGTG GTGGGATGAT ACGTGGTTGA
H11-1   GTGGTTCGGT AATTTGGTCA CGATGAAGTG GTGGGATAAC CTATGGCTGA 1251                                           1300
H11-3   ATGAAGGTTT TGCAAGATTC ACAGAATTTA TTGGAGCTGG TCAGATAACT
H11-2   ACGAAGGTTT TGCAACATTT GTTGAGTATC TTGGAATGGA CGAAATTAGC
H11-1   ACGAAGGATT CGCGTCATTC GTGGAATACA TCGGAGCCGA CTTCATCAGC 1301                                           1350
H11-3   CAAGATGACG CCAGAATGAG GAACTACTTC CTGATTGATG TACTTGAACG
H11-2   CACAACAATT TCAGAACGCA AGATTTCTTC TTGCTCGATG GAATGGATCG
H11-1   GATGGTCTAT GGGAAATGAA AGATTTCTTC CTGCTGGCAC CGTACACAAG 1351                                           1400
H11-3   CGCTTTGAAA GCTGATTCGG TAGCGTCAAG CCATCCACTT TCCTTCAGAA
H11-2   CGGAATGAGA GCTGACTCGG CAGCATCGAG CCATCCGCTT TCGTTTAGGA
H11-1   TGGTATTACG GCTGATGCAG TAGCTTCAAG CCATCCGCTT TCCTTCAGAA 1401                                           1450
H11-3   TCGACAAAGC TGCAGAAGTT GAAGAAGCCT TTGATGATAT CACATACGCC
H11-2   TTGACAAAGC GGCAGAAGTT GCCGAAGCCT TTGACGATAT TTCATACGCC
H11-1   TAGATAAGGC TGCAGATGTA TCAGAAGCGT TCGATGATAT CACATACCGT 1451                                           1500
H11-3   AAAGGAGCTT CTGTTCTTAC TATGCTGAGA GCCTTGATTG GAGAAGAAAA
H11-2   AAGGGAGCGT CAGTTCTCAC TATGCTACGG GCTTTGATTG GAGAGGACAA
H11-1   AAAGGAGCAT CCGTTCTTCA ATGCTATTG AATTTAGTTG GGGACGAAAA 1501                                           1550
H11-3   ACATAAGCAT GCAGTATCGC AGTACCTCAA GAAGTTCTCG TATAGCAATG
H11-2   TTACAGGAAT GCTGTTGTGC AATACCTCAA GAAGTTCTCC TACAGCAATG
H11-1   TTTCAAGCAG TCTGTTTCGC GTTACCTCAA GAAGTTTTCA TATGATAATG 1551                                           1600
H11-3   CAGAAGCGAC TGATCTATGG GCAGTTTTTG ATGAAGTTGT CACTGACGTC
H11-2   CACAAGCAGC CGATCTGTGG AACGTCTTCA ATGAAGTTGT CAAAGGTGTT
H11-1   CGGCTGCTGA AGATTTATGG GCAGCATTCG ACGAAACCGT CCAAGGTATA 1601                                           1650
H11-3   GAAGGTCCAG ACGGCAAACC TATGAAAACC ACAGAGTTTG CAAGTCAGTG
H11-2   AAGGGTCCTG ACGGCAACGT CATGAAAATC GACCAATTTA CCGATCAGTG
H11-1   ACCGGACCTA ATGGTGGACC ATTGAAAATG TCCGAGTTTG CGCCACAATG 1651                                           1700
H11-3   GACGACTCAG ATGGGCTTCC CAGTTATTTC CGTAGCAGAG TTTAACTCGA
H11-2   GACGTATCAG ATGGGTTATC CTGTGGTTAA AGTAGAAGAA TTTAATGCGA
H11-1   GACAACTCAG ATGGGGTTCC CTGTTCTTAC TGTCGAGTCG GTTAACGCAA 1701                                           1750
H11-3   CTACTTTGAA ATTAACGCAA AGTCGATATG AGGCGAATAA AGACGCTGTG
H11-2   CCGCCCTAAA GGTTACGCAG AGCCGGTACA AGACAAATAA AGACGCCTTG
H11-1   CGACTTTGAA AGTCACCCAA AAACGATACA GGCAGAACAA GGATGCAAAG
```

FIG. 2 (contd)

```
        1751                                                    1800
H11-3   GAGAAAGAGA AGTACCGTCA CCCGAAATAC GGATTTAAAT GGGATATTCC
H11-2   GAACCAGAGA AATATCGTAA TCCAAAATAC GGGTTCAAGT GGGATGTTCC
H11-1   GAACCAGAGA AGTACCGTCA TCCAACTTAT GGGTTCAAAT GGGATGTTCC 1801                                                    1850
H11-3   ACTGTGGTAT CAGGAAGGCG ATAAGAAGGA GATAAAGCGA ACATGGTTGA
H11-2   CCTATGGTAT CAGGAAGGCA ATAGCAAAGA GGTGAAGCGA ACATGGCTAA
H11-1   TCTGTGGTAT CAGGAAGATG AA...CAGCA AGTGAAAAGA ACTTGGTTAA 1851                                                    1900
H11-3   GAAGAGATGA ACCGCTTTAC TTGCATGTTA GTGATGCTGG CGCTCCCTTT
H11-2   AAAGAGATGA ACCGCTGTAC TTGAACGTCA ACAATCGGGA TACATCCCTT
H11-1   AAAGAGAGGA ACCGCTCTAT TTCCATGTAA GCAATTCTGA TTCGTCAGTT 1901                                                    1950
H11-3   GTGGTGAACG CAGACCGCTA TGGATTTTAT CGACAAAATC ATGACGCTAA
H11-2   GTGGTGAACG CTGATCGACA TGGATTTTAT CGACAAAACT ATGATGCCAA
H11-1   GTGGTGAATG CCGAACGTCG TGCTTTTTGC CGATCAAACT ATGACGCTAA 1951                                                    2000
H11-3   TGGTTGGAAA AAGATAATCA AGCAGCTCAA GGATAATCAT GAGGTTTACA
H11-2   CGGTTGGAAA AAGATAATCA AGCAGCTCAA GAAAGATCAC AAGGTCTTCG
H11-1   CGGTTGGAGG AACATTATGA GAAGACTCAA GCAGAATCAT AAGGTCTATG 2001                                                    2050
H11-3   GTCCCCGGAC AAGGAATGTC ATCATTAGCG ATGCGTTTGC TGCGGCTGCA
H11-2   GTCCAAGGAC AAGGAACGCT ATCATAAGCG ATGCATTTGC TGCAGCTACG
H11-1   GTCCACGAAC AAGAAACGCT CTCATAAGTG ATGCGTTTGC AGCAGCTGCA 2051                                                    2100
H11-3   ACTGACGCAA TTGAGTATGA GACTGTATTT GAACTTCTGA ATTATGCCGA
H11-2   ATTGACGCAA TCGACTATGA AACTGTATTC GAACTACTTG AATATGCCAA
H11-1   GTTGAGGAAA TGAATTACGA GACCGTATTT GAAATGCTCA AATACACCGT 2101                                                    2150
H11-3   AAAAGAAACG GAATATCTAC CATTAGAAAT CGCAATGTCC GGGATCTCTT
H11-2   AAATGAAGAG GAATTCTTGC CTTGGAAGGA AGCTCTGTCC GGCATGTTCG
H11-1   GAAAGAAGAG GATTACTTAC CATGGAAGGA GGCAATATCA GGATTCAATA 2151                                                    2200
H11-3   CGATTTTGAA ATACTTCCCT ACCGAGCCAG AGGCAAAGCC AGCTCAAACA
H11-2   CAGTTTTAAA GTTCTTCGGT AATGAGCCGG AGACAAAACC AGCTAGAGCT
H11-1   CAATTTTGGA CTTTTTCGGC AGCGAACCCG AATCTCAATG GGCTTCGGAA 2201                                                    2250
H11-3   TACATGATGA ACATATTGAA ACCGATGTAT GAAAAAAGCA GTATCGACTT
H11-2   TACATGATGA GCATATTAGA ACCGATGTAT AATAAGAGCA GCATTGATTA
H11-1   TACATGCGAA AACTGATGAA GCCAATTTAT GACAAGAGTA GCATCAAGTT 2251                                                    2300
H11-3   CATTGCCAAT AACTACAGAA ATGACAAGCT GTTTTTCCAA ATCAACCTCC
H11-2   CATCGTCAAG AATTATTTGG ATGATACGTT ATTCACAAAA ATTAATACTC
H11-1   TATAGCGGAG AACTACAAAA AAGATTCGCT TTTCTTCAAA AATAATCTCC 2301                                                    2350
H11-3   AAAAAGATGT CATTGATATG TTCTGCGCCC TCGGATCGCA AGACTGCAGG
H11-2   AAAAGGATAT CATTGATGCA TATTGTTCCC TTGGATCAAA GGACTGTATA
```

FIG.2 (contd)

```
H11-1    AAATAGCTGT TATTGACACA TACTGTGGTC TTGGAGGCAA AGAATGTCTT 2351                                                2400
H11-3    AAGAAATATA AAAAACTTTT CGATGACGAA GTCATGAACA AATGCAGGGA
H11-2    AAGCAATATA AGGATATCTT CTACGATGAG GTTATGCCCA AGTGTAAGGC
H11-1    GAAGAAATGA AAAAGCTTTT TGACAAGGAG GTCATG...A AATGTCAACC 2401                                                2450
H11-3    TGGTCAAGCA GCAACCGAAT GCGTAAGAAT CGCCGCTCCT CTCCGATCAA
H11-2    CGGGGAAGCA GCAACCAAAT GCGTTAAGGT TTCCGCTCCT CTTCGAGCCA
H11-1    TGGTCAGCAA GCGACCGACT GCGTAAAGGT AACTGCTCCT CTCCGAAAAA 2451                                                2500
H11-3    GTGTTTATTG TTATGGTGTG AAGGAAGGCG GTGATTATGC TTCCGACAAG
H11-2    ATGTTTACTG TTATGGTGTA CAGGAAGGTG GTGAAGAAGC TTTTGAAAAG
H11-1    CTGTTTACTG CTATGGGGTC CAGGAAGGCG GTGATGAGGC ATTCGACAAG 2501                                                2550
H11-3    GTGATGGAGC TTTATACGGC CGAAACACTC GCCCTAGAAA AAGACTTCCT
H11-2    GTGATGGGGC TGTATCTAGC AGAAGATGTT CAACTGGAGA AGGGTATCCT
H11-1    GTGATGGAAC TATATAATGC GGAACAAGTG CAGTTGGAGA AAGACAGTCT 2551                                                2600
H11-3    ACGCCTAGCA TTGGGATGTC ATAAAGATGT TACTGCTTTG AAAGGACTTC
H11-2    GTTCAAAGCC TTGGCATGCC ACAAAGATGT TACAGCTCTA AAAGAACTTC
H11-1    ACGTGAAGCA TTGGGATGCC ATAAAGACGT TACAGCTCTA AAGGGACTTC 2601                                                2650
H11-3    TCTTGCGGGC TCTGGACAGG AATTCGTCGT TCGTACGTAT GCAGGATATC
H11-2    TTTTGCGAGC CCTGGACCGT AAATCGTCGT TTGTGCGTCT TCAGGATGTC
H11-1    TTATGCTGGC TTTGGATCGG AATTCGTCAT TTGTGCGTCT TCAAGATGCT 2651                                                2700
H11-3    CCAAGTGCTT TCAACGATGT AGCAGCAAAT CCTATTGGCG AAGAATTCAT
H11-2    CCTACCGCTT TCCGTGCTGT ATCTGAAAAC CCTGTGGGCG AAGAATTCAT
H11-1    CATGATGTGT TTAACATTGT ATCCAGAAAT CCTGTTGGAA ACGAACTGCT 2701                                                2750
H11-3    TTTCAATTTC CTTATTGAGA GATGGCCAGA TATCATTGAA AGTATAGGAA
H11-2    GTTCAATTTC CTAATGGAGA GATGGGAGGA ATCACTGCG AGCTTGGAAA
H11-1    GTTCAATTTC CTCACAGAGC GATGGGAAGA GATACTTGAA AGTTTGTCAA 2751                                                2800
H11-3    CGAAGCACAC ATATGTTGAG AAAGTGATAC CAGCCTGCAC TTCAGGAATC
H11-2    CAGAACACAG AGCAGTTGAT AAAGTGGTCG GCGCTTGTTG CACAGGAATT
H11-1    TACGACACAG ATCAGTTGAT CGAGTGATCA AAGCCTGTAC TCGAGGACTA 2801                                                2850
H11-3    CGCTCACAAC AGCAGATTGA CCAGCTGAAG AATCTGCAGA AAAATGGCAT
H11-2    CGCTCCCAAC AACAAATAGA TCAGCTGAAG AATCTACAGA AGAACAATGC
H11-1    CGATCCAGGG AACAAGTACA ACAGTTGAAG AATCTATACA AAAATGACAA 2851                                                2900
H11-3    GAACGCTCGT CAATTCGGTG CATTCGATAA AGCAATCGAA CGAGCACAAA
H11-2    GCAGGCTAAG AAGTTCGGCT CATTCACCCA GGAAATCGAA AAAGGAGAAC
H11-1    GCGTGCTCGC GAATACGGTG CATTTGGTGG GGCAATAGAA AGATCGGAAC 2901                                                2950
```

```
H11-3    ATAGGGTGGA TTGGATTAAA AAACATTTCC AAAAATTAGC GGCTTTCTTC
H11-2    ATAAAATTGC CTGGATCAAG AAACATTTTC ACAGATTATC GGAATTCTTC
H11-1    ACAGAGTCAA ATGGATTGAG AAACATTTCC GAAAACTAGC AGCTTTCTTC 2951       2958
H11-3    AAGAAAGCCA CCTTGTAA
H11-2    AAGAGAGCAA GATCATAG
H11-1    AAAAAATCTA ATTCATAA
```

FIG. 2 (contd)

```
              1                                                             50
M1                         C GCGGACATTG CTGAATCTAA CTCCAATCCG
AustM1     ATGACGTCGC AGGGGAGAAC GCGGACATTG CTGAATCTAA CTCCAATCCG
H11-3      ATGACGTCGC AGGGGAGAAC GCGGACATTG CTGAATCTAA CTCCAATCCG 51                                                            100
M1         TCTTATTGTC GCATTATTTC TAGTAGCTGC TGCAGTCGGC CTCTCTATTG
AustM1     TCTTATTGTC GCATTATTTC TAGTAGCTGC TGCAGTCGGC CTCTCTATTG
H11-3      TCTTATTGTC GCATTATTTC TAGTAGCTGC TGCAGTCGGC CTCTCTATTG 101                                                           150
M1         GTCTCACCTA TTACTTTACT CGCAAAGCGT TCGATACCTC AGAAAAGCCA
AustM1     GTCTCACCTA TTACTTTACT CGCAAAGCGT TCGATACCTC AGAAAAGCCA
H11-3      GTCTCACCTA TTACTTTACT CGCAAAGCGT TCGATACCTC AGAAAAGCCA 151                                                           200
M1         GGGAAGGATG ATACTGGTGG CAAGGACAAA GACAATTCTC CCTCTGCGGC
AustM1     GGGAAGGATG ATACTGGTGG CAAGGACAAA GACAATTCTC CCTCTGCGGC
H11-3      GGGAAGGATG ATACTGGTGG CAAGGACAAA GACAATTCTC CCTCTGCGGC 201                                                           250
M1         GGAACTACTT CTTCCAAGTA ATATAAAACC ATTGTCTTAC GACTTGACGA
AustM1     GGAACTACTC CTTCCAAGTA ATATAAAACC ATTGTCTTAC GACTTGACGA
H11-3      GGAACTACTC CTTCCAAGTA ATATAAAACC ATTGTCTTAC GACTTGACGA 251                                                           300
M1         TCAAAACATA TCTACCTGGT TATGTGGACT TCCCACCGGA GAAAAACCTC
AustM1     TCAAAACATA TCTACCTGGT TATGTGGACT TCCCACCGGA GAAAAACCTC
H11-3      TCAAAACATA TCTACCTGGT TATGTGGACT TCCCACCGGA GAAAAACCTC 301                                                           350
M1         ACATTCGACG GGCG
AustM1     ACATTCGATG GGCGTGTGGA AATATCAATG GTTGTAATTG AGCCAACAAA
H11-3      ACATTCGATG GGCGTGTGGA AATATCAATG GTTGTAATTG AGCCAACAAA 351                                                           400
AustM1     GAGTATCGTA CTCAATTCAA AGAAGATCTC TGTAATACCC CAAGAATGTG
H11-3      GAGTATCGTA CTCAATTCAA AGAAGATCTC TGTAATACCC CAAGAATGTG 401                                                           450
AustM1     AACTGGTATC GGGCGATAAA AAATTCGAAA TTGAAAGTGT AAAGGAGCAC
H11-3      AACTGGTATC GGGCGATAAA AAACTCGAAA TTGAAAGTGT AAAGGAGCAC 451                                                           500
AustM1     CCAAGACTGG AAAAGGTTGA GTTTCTTATC AAAAGCCAAC TGGAAAAAGA
H11-3      CCAAGACTGG AAAAGGTTGA GTTTCTTATC AAAAGCCAAC TGGAAAAAGA 501                                                           550
AustM1     TTCACAAATC TTGCTCAAGT CGGCTTACAT CGGTCTCATC AGCAACAGCC
H11-3      TCAACAAATC TTGCTCAAGG TCGGCTACAT CGGTCTCATC AGCAACAGCT 551                                                           600
AustM1     TTGGTGGAAT CTACCAGACC ACTTATACCA CCCCGGATGG CACCCCTAAG
H11-3      TTGGTGGAAT CTACCAGACC ACTTATACCA CCCCGGATGG CACCCCTAAG 601                                                           650
AustM1     ATCGCTGCAG TTTCACAAAA TGAGCCCATA GATGCTCGTC GAATGGTACC
H11-3      ATCGCTGCAG TTTCACAAAA TGAGCCCATA GATGCTCGTC GAATGGTACC
```

FIG. 3

```
                651                                                      700
AustM1   ATGCATGGAT GAACCGAAAT ACAAAGCAAA CTGGACCGTT ACTGTCATTC
H11-3    ATGCATGGAT GAACCGAAAT ACAAAGCAAA CTGGACCGTT ACTGTCATTC 701                                                      750
AustM1   ATCCAAAAGG CACCAAAGCC GTCTCGAATG GAATCGAAGT GAACGGAGAT
H11-3    ATCCAAAAGG CACCAAAGCC GTCTCGAATG GAATCGAAGT GAACGGAGAT 751                                                      800
AustM1   GGAGAGATCA GTGGTGATTG GATCACATCG AAGTTCTTGA CTACTCCACG
H11-3    GGAGAGATCA GTGGTGATTG GATCACATCG AAGTTCTTGA CTACTCCACG 801                                                      850
AustM1   GATGTCATCC TACTTGTTGG CAGTTATGGT TTCAGAATTT GAATACATCG
H11-3    GATGTCATCC TACTTGTTGG CAGTTATGGT TTCAGAATTT GAATACATCG 851                                                      900
AustM1   AAGGTGAAAC AAAGACGGGT GTTCGGTTCC GTATATGGTC ACGCCCAGAG
H11-3    AAGGTGAAAC AAAGACGGGT GTTCGGTTCC GTATATGGTC ACGCCCAGAG 901                                                      950
AustM1   GCAAAGAAGA TGACACAATA TGCTCTGCAA TCTGGTATCA AGTGCATA
H11-3    GCAAAGAAGA TGACACAATA TGCTCTGCAA TCTGGTATCA AGTGCATAGA 951                                                     1000
H11-3    ATTCTACGAA GATTTCTTTG ATATCAGATT CCCTCTGAAG AAACAAGATA 1001                                                     1050
H11-3    TGATTGCCCT TCCTGATTTC TCTGCCGGTG CCATGGAGAA TTGGGGCCTC 1051                                                     1100
H11-3    ATCACTTACA GGGAAAACTC TTTGTTGTAC GATGACAGAT CTATGCACC 1101                                                     1150
H11-3    GATGAATAAA CAGCGAATTG CTCGCATTGT TGCTCATGAG CTTGCTCATC 1151                                                     1200
H11-3    AGTGGTTCGG CGACTTGGTT ACGATGAAGT GGTGGGATAA TTTGTGGTTG 1201                                                     1250
H11-3    AATGAAGGTT TTGCAAGATT CACAGAATTT ATTGGAGCTG GTCAGATAAC 1251                                                     1300
H11-3    TCAAGATGAC GCCAGAATGA GGAACTACTT CCTGATTGAT GTACTTGAAC 1301                                                     1350
H11-3    GCGCTTTGAA AGCTGATTCG GTAGCGTCAA GCCATCCACT TTCCTTCAGA 1351                                                     1400
H11-3    ATCGACAAAG CTGCAGAAGT TGAAGAAGCC TTTGATGATA TCACATACGC 1401                                                     1450
H11-3    CAAAGGAGCT TCTGTTCTTA CTATGCTGAG AGCCTTGATT GGAGAAGAAA 1451                                                     1500
H11-3    AACATAAGCA TGCAGTATCG CAGTACCTCA AGAAGTTCTC GTATAGCAAT 1501                                                     1550
```

FIG. 3 (contd)

| | | | | |
|---|---|---|---|---|
| H11-3 | GCAGAAGCGA | CTGATCTATG | GGCAGTTTTT | GATGAAGTTG | TCACTGACGT |

| 1551 | | | | 1600 |
|---|---|---|---|---|
| H11-3 | CGAAGGTCCA | GACGGCAAAC | CTATGAAAAC | CACAGAGTTT | GCAAGTCAGT |

| 1601 | | | | 1650 |
|---|---|---|---|---|
| H11-3 | GGACGACTCA | GATGGCTTC | CCAGTTATTT | CCGTAGCAGA | GTTTAACTCG |

| 1651 | | | | 1700 |
|---|---|---|---|---|
| H11-3 | ACTACTTTGA | AATTAACGCA | AAGTCGATAT | GAGGCGAATA | AAGACGCTGT |

| 1701 | | | | 1750 |
|---|---|---|---|---|
| H11-3 | GGAGAAAGAG | AAGTACCGTC | ACCCGAAATA | CGGATTTAAA | TGGGATATTC |

| 1751 | | | | 1800 |
|---|---|---|---|---|
| H11-3 | CACTGTGGTA | TCAGGAAGGC | GATAAGAAGG | AGATAAAGCG | AACATGGTTG |

| 1801 | | | | 1850 |
|---|---|---|---|---|
| H11-3 | AGAAGAGATG | AACCGCTTTA | CTTGCATGTT | AGTGATGCTG | GCGCTCCCTT |

| 1851 | | | | 1900 |
|---|---|---|---|---|
| H11-3 | TGTGGTGAAC | GCAGACCGCT | ATGGATTTTA | TCGACAAAAT | CATGACGCTA |

| 1901 | | | | 1950 |
|---|---|---|---|---|
| H11-3 | ATGGTTGGAA | AAAGATAATC | AAGCAGCTCA | AGGATAATCA | TGAGGTTTAC |

| 1951 | | | | 2000 |
|---|---|---|---|---|
| H11-3 | AGTCCCCGGA | CAAGGAATGT | CATCATTAGC | GATGCGTTTG | CTGCGGCTGC |

| 2001 | | | | 2050 |
|---|---|---|---|---|
| H11-3 | AACTGACGCA | ATTGAGTATG | AGACTGTATT | TGAACTTCTG | AATTATGCCG |

| 2051 | | | | 2100 |
|---|---|---|---|---|
| H11-3 | AAAAGAAAC | GGAATATCTA | CCATTAGAAA | TCGCAATGTC | CGGGATCTCT |

| 2101 | | | | 2150 |
|---|---|---|---|---|
| H11-3 | TCGATTTTGA | AATACTTCCC | TACCGAGCCA | GAGGCAAAGC | CAGCTCAAAC |

| 2151 | | | | 2200 |
|---|---|---|---|---|
| H11-3 | ATACATGATG | AACATATTGA | AACCGATGTA | TGAAAAAAGC | AGTATCGACT |

| 2201 | | | | 2250 |
|---|---|---|---|---|
| H11-3 | TCATTGCCAA | TAACTACAGA | AATGACAAGC | TGTTTTTCCA | AATCAACCTC |

| 2251 | | | | 2300 |
|---|---|---|---|---|
| H11-3 | CAAAAGATG | TCATTGATAT | GTTCTGCGCC | CTCGGATCGC | AAGACTGCAG |

| 2301 | | | | 2350 |
|---|---|---|---|---|
| H11-3 | GAAGAAATAT | AAAAAACTTT | TCGATGACGA | AGTCATGAAC | AAATGCAGGG |

| 2351 | | | | 2400 |
|---|---|---|---|---|
| H11-3 | ATGGTCAAGC | AGCAACCGAA | TGCGTAAGAA | TCGCCGCTCC | TCTCCGATCA |

| 2401 | | | | 2450 |
|---|---|---|---|---|
| H11-3 | AGTGTTTATT | GTTATGGTGT | GAAGGAAGGC | GGTGATTATG | CTTCCGACAA |

| 2451 | | | | 2500 |
|---|---|---|---|---|
| H11-3 | GGTGATGGAG | CTTTATACGG | CCGAAACACT | CGCCCTAGAA | AAAGACTTCC |

FIG. 3 (contd)

```
        2501                                              2550
H11-3   TACGCCTAGC ATTGGGATGT CATAAAGATG TTACTGCTTT GAAAGGACTT 2551                                              2600
H11-3   CTCTTGCGGG CTCTGGACAG GAATTCGTCG TTCGTACGTA TGCAGGATAT 2601                                              2650
H11-3   CCCAAGTGCT TTCAACGATG TAGCAGCAAA TCCTATTGGC GAAGAATTCA 2651                                              2700
H11-3   TTTTCAATTT CCTTATTGAG AGATGGCCAG ATATCATTGA AAGTATAGGA 2701                                              2750
H11-3   ACGAAGCACA CATATGTTGA GAAAGTGATA CCAGCCTGCA CTTCAGGAAT 2751                                              2800
H11-3   CCGCTCACAA CAGCAGATTG ACCAGCTGAA GAATCTGCAG AAAAATGGCA 2801                                              2850
H11-3   TGAACGCTCG TCAATTCGGT GCATTCGATA AAGCAATCGA ACGAGCACAA 2851                                              2900
H11-3   AATAGGGTGG ATTGGATTAA AAAACATTTC CAAAAATTAG CGGCTTTCTT 2901         2919
H11-3   CAAGAAAGCC ACCTTGTAA
```

FIG. 3 (contd)

| H11-2 | GGTTTAATTA | CCCAAGTTTG | AGATGACGGC | GGAGTGGCAG | AAGCGTCGAA | 50 |
| --- | --- | --- | --- | --- | --- | --- |
| H11-2 | TCTTGGGCTT | CTCACCTATC | AGCCTACTTT | GTACATTATT | TGTATTAGCT | 100 |
| H11-2 | GCTGCCGTTG | GACTCTCCAT | TGGTCTTACC | TATTACTTCA | CTCGTAAAGC | 150 |
| H11-2 | ATTCGATACC | ACACAAAAAG | AACAGAAGGA | TGACAGTGGT | GGTAAAGAAA | 200 |
| H11-2 | AGGATAATTC | TCCTTCTGCA | GAAGAACTAC | TTCTTCCAAC | GAACATAAAA | 250 |
| H11-2 | CCAGTCTCGT | ACGACTTGAA | CATCAAAACA | TATCTACCGG | GTTACGTGAA | 300 |
| H11-2 | CTTTCCACCA | GAAAAGAATC | TCACATTTGA | TGCCCATGTG | AGATTGCTA | 350 |
| H11-2 | TGGTTGTGGT | TGAGCCTACA | AATAGTATTG | TGCTGAACTC | GAAGAAAATC | 400 |
| H11-2 | ACTTTGGCAC | AAGGAGGATG | CGAACTGTTC | TCAGGTAATC | AGAAACTTGA | 450 |
| H11-2 | CATCGAAAGT | GTAAAGATGC | AGGAAAGACT | TGACAAGCTT | GAGATTACCC | 500 |
| H11-2 | TCAAAAATCA | GCTGCAAAAA | GATCTGAAAA | TCCTGCTCAA | GATCACTTAC | 550 |
| H11-2 | ACCGGCCTTA | TTAGCGACAC | TCTCGGTGGG | CTCTACCAGT | CCATCTACAC | 600 |
| H11-2 | TGATAAGGAC | GGAAAAACTA | AGATCGTTGC | TGTTTCACAA | AATGAACCAT | 650 |
| H11-2 | CAGACGCTCG | TCGTATAGCG | CCATGCTTTG | ACGAACCGAA | GTACAAGGCA | 700 |
| H11-2 | ACATGGACTG | TCACCGTCGT | TCATCCCAAA | GGTACAAAGG | CTGCATCGAA | 750 |
| H11-2 | CGGCATTGAA | GCAAATGGAA | AAGGGGAGCT | CAAGGGTGAT | TGGATAACGT | 800 |
| H11-2 | CTAAATTTAA | AACTACCCCA | CCGATGTCGT | CCTATTTATT | GGCTATTATT | 850 |
| H11-2 | GTTTGTGAAT | TTGAATACAT | TGAAGGATTT | ACAAAAACGG | GTGTTCGGTT | 900 |
| H11-2 | CCGTATATGG | TCTCGACCAG | AGGCGAAACG | AATGACGGCA | TACGCTTTGG | 950 |
| H11-2 | ATGCTGGCAT | CAGATGCCTG | GAGTTCTATG | AGAAGTTCTT | TGACATAAAA | 1000 |
| H11-2 | TTCCCTCTGG | AAAAACAAGA | TATGATTGCT | CTTCCTGATT | TCACCGCTGG | 1050 |
| H11-2 | TGCCATGGAA | AACTGGGGCC | TTATCACTTA | TAGAGAGGAT | TCTCTCCTAT | 1100 |
| H11-2 | ACGATGAAAA | AATTTATGCA | CCGATGAATA | AACAGCGGGT | TGCTCTCGTA | 1150 |
| H11-2 | GTTGCTCACG | AGCTTGCTCA | TCAGTGGTTC | GGCAATCTGG | TCACACTGAA | 1200 |
| H11-2 | GTGGTGGGAT | GATACGTGGT | TGAACGAAGG | TTTTGCAACA | TTTGTTGAGT | 1250 |
| H11-2 | ATCTTGGAAT | GGACGAAATT | AGCCACAACA | ATTTCAGAAC | GCAAGATTTC | 1300 |
| H11-2 | TTCTTGCTCG | ATGGAATGGA | TCGCGGAATG | AGAGCTGACT | CGGCAGCATC | 1350 |
| H11-2 | GAGCCATCCG | CTTTCGTTTA | GGATTGACAA | AGCGGCAGAA | GTTGCCGAAG | 1400 |
| H11-2 | CCTTTGACGA | TATTTCATAC | GCCAAGGGAG | CGTCAGTTCT | CACTATGCTA | 1450 |

FIG. 4

```
H11-2  CGGGCTTTGA TTGGAGAGGA CAATTACAGG AATGCTGTTG TGCAATACCT  1500
H11-2  CAAGAAGTTC TCCTACAGCA ATGCACAAGC AGCCGATCTG TGGAACGTCT  1550
H11-2  TCAATGAAGT TGTCAAAGGT GTTAAGGGTC CTGACGGCAA CGTCATGAAA  1600
H11-2  ATCGACCAAT TTACCGATCA GTGGACGTAT CAGATGGGTT ATCCTGTGGT  1650
H11-2  TAAAGTAGAA GAATTTAATG CGACCGCCCT AAAGGTTACG CAGAGCCGGT  1700
H11-2  ACAAGACAAA TAAAGACGCC TTGGAACCAG AGAAATATCG TAATCCAAAA  1750
H11-2  TACGGGTTCA AGTGGGATGT TCCCCTATGG TATCAGGAAG GCAATAGCAA  1800
H11-2  AGAGGTGAAG CGAACATGGC TAAAAAGAGA TGAACCGCTG TACTTGAACG  1850
H11-2  TCAACAATCG GGATACATCC CTTGTGGTGA ACGCTGATCG ACATGGATTT  1900
H11-2  TATCGACAAA ACTATGATGC CAACGGTTGG AAAAAGATAA TCAAGCAGCT  1950
H11-2  CAAGAAAGAT CACAAGGTCT TCGGTCCAAG GACAAGGAAC GCTATCATAA  2000
H11-2  GCGATGCATT TGCTGCAGCT ACGATTGACG CAATCGACTA TGAAACTGTA  2050
H11-2  TTCGAACTAC TTGAATATGC CAAAAATGAA GAGGAATTCT TGCCTTGGAA  2100
H11-2  GGAAGCTCTG TCCGGCATGT TCGCAGTTTT AAAGTTCTTC GGTAATGAGC  2150
H11-2  CGGAGACAAA ACCAGCTAGA GCTTACATGA TGAGCATATT AGAACCGATG  2200
H11-2  TATAATAAGA GCAGCATTGA TTACATCGTC AAGAATTATT TGGATGATAC  2250
H11-2  GTTATTCACA AAAATTAATA CTCAAAAGGA TATCATTGAT GCATATTGTT  2300
H11-2  CCCTTGGATC AAAGGACTGT ATAAAGCAAT ATAAGGATAT CTTCTACGAT  2350
H11-2  GAGGTTATGC CCAAGTGTAA GGCCGGGGAA GCAGCAACCA AATGCGTTAA  2400
H11-2  GGTTTCCGCT CCTCTTCGAG CCAATGTTTA CTGTTATGGT GTACAGGAAG  2450
H11-2  GTGGTGAAGA AGCTTTTGAA AAGGTGATGG GGCTGTATCT AGCAGAAGAT  2500
H11-2  GTTCAACTGG AGAAGGGTAT CCTGTTCAAA GCCTTGGCAT GCCACAAAGA  2550
H11-2  TGTTACAGCT CTAAAAGAAC TTCTTTTGCG AGCCCTGGAC CGTAAATCGT  2600
H11-2  CGTTTGTGCG TCTTCAGGAT GTCCCTACCG CTTTCCGTGC TGTATCTGAA  2650
B2                                               GGGA       4
H11-2  AACCCTGTGG GCGAAGAATT CATGTTCAAT TTCCTAATGG AGAGATGGGA  2700
B2     GGAAATCACT GCGAGCTTGG AAACAGAACA CAGAGCAGTT GATAAAGTGG   54
H11-2  GGAAATCACT GCGAGCTTGG AAACAGAACA CAGAGCAGTT GATAAAGTGG  2750
B2     TCGGCGCTTG TTGCACAGGA ATTCGCTCCC AACAACAAAT AGATCAGCTG  104
H11-2  TCGGCGCTTG TTGCACAGGA ATTCGCTCCC AACAACAAAT AGATCAGCTG  2800
B2     AAGAAGAATC TACAGAAGAA CAATGCGCAG GCTAAGAAGT TC........  154
```

FIG. 4 (cont'd)

```
H11-2  AAGAA...TC TACAGAAGAA CAATGCGCAG GCTAAGAAGT TCGGCTCATT 2850

B2     .......... .......... .....CATAA AATTGCCTGG ATCAAGAAAC  204
H11-2  CACCCAGGAA ATCGAAAAAG GAGAACATAA AATTGCCTGG ATCAAGAAAC 2900

B2     ATTTTCACAG ATTATCGGAA TTCTTCAAGA GAGCAAGATC ATAGCTTTTC
H11-2  ATTTTCACAG ATTATCGGAA TTCTTCAAGA GAGCAAGATC ATAGCTTTTC 2950

B2     ACACTGAGCT CCAATTTTAA CGTCTTCAAA CTAGGAGACA GTTTTGCTGA
H11-2  ACACTGAGCT CCAATTTTAA CGTCTTCAAA CTAGGAGACA GTTTTGCTGA 3000

B2     AAAGTCAGTT TCACATTTTC CGTTTGAATG CCATCCATTC GAATACAACC
H11-2  AAAGTCAGTT TCACATTTTC CGTTTGAATG CCATCCATTC GAATACAACC 3050

B2     AA...CCCCA TTTTAAGTAC CTTTCATTCA CAGTGATTAC TAAATTTCGA
H11-2  AATAATACCA TTTTAAGTAC CTTTCATTCA CAGTGATTAC TGAATTTCGA 3100

B2     ATATATTATG AAGCTTGTAT CTTGAACGTT ATGATCGGTG ACTTTCAATT
H11-2  ATATATCATG AAGCTTGTAT CTTGAACGTT ATGATCGGTG ACTTTCAATT 3150

B2     TATAGAGCTC ACTCTCCATT TTGTAGCTGT GATGACTTGC ATTTAAGACC
H11-2  TATAGAGCTC ACTCTCCATT TTGTAGCTGT GATGACTTGC ATTTAAGACC 3200

B2     CACCATTTAC CAGCCTATAA TCTTTCCCCA ATACATTCCA AACTCCGATC
H11-2  CACCATTTAC CAGCCTAGAA TCTTTCCCCA ATACATTCCA AACTCCGATC 3250

B2     ACCTCCACCG CTGACAATGC CCAGATTTGT TTCTTTGTCT GCTATCCATC
H11-2  ACCTCCACCG CTGACAATGC CCAGATTTGT TTTTTTGTCT GCTATCCATC 3300

B2     TAACTGTTTC GAT
H11-2  TAACTGTTTC GATCGCCGGT TGTTTGTCAA TTGCTTATCT GATAAATATT 3350

H11-2  GACGTTGGTG T                                             3361
```

FIG. 4 (contd)

```
         1                                                    50
H11-1  GGTTTAATTA CCCAAGTTTG AGATGACAGC AGAGGAGAGT CAGGAGCAGG 51                                                   100
H11-1  AGACGCAGCA ACCACGAAAA AATACAGTGC TACGGCTCAC CCCAATCAAG 101                                                  150
H11-1  TCTCTCTTTG CTTTGTTAGT GGTAGCTGCT GCCGTCGGCC TCTCAATCGG 151                                                  200
H11-1  TCTCACCTAT TACTTTACAA GGAAAGCTTT TGATACTACT GGCGGAAATG 201                                                  250
H11-1  GAAAAGGGGA TCAACCTATT GTCGATGATA ATTCCCCATC AGCTGAAGAA 251                                                  300
H11-1  TTACGTCTCC CAACAACCAT AAAACCTTTG ACATACGACT TAGTAATCAA 301                                                  350
H11-1  AACGTATCTG CCAAACTATG TAAACTATCC ACCTGAGAAA GATTTCGCTA 351                                                  400
H11-1  TTGATGGGAC TGTGGTGATT GCTATGGAAG TTGTGGAGCC AACAAAGTCT 401                                                  450
H11-1  ATTGTGCTCA ACTCGAAAAA TATTCCTGTA ATTGCAGACC AGTGCGAACT 451                                                  500
H11-1  GTTTTCTAAC AACCAAAAAC TCGACATCGA AAAGGTTGTG GATCAGCCAA 501                                                  550
H11-1  GGCTGGAGAA AGTCGAATTC GTTTTGAAGA AAAAGCTGGA GAAGAATCAG 551                                                  600
H11-1  AAAATCACGC TCAAGATTGT ATACATTGGC CTTATCAACG ACATGCTTGG 601                                                  650
H11-1  AGGACTTTAT CGAACAACCT ACACGGATAA AGATGGTACA ACCAAGATTG 651                                                  700
H11-1  CTGCATGCAC TCATATGGAA CCGACGGACG CCCGTCTTAT GGTCCCCTGT 701                                                  750
H11-1  TTCGACGAGC CGACGTTTAA GGCAAACTGG ACTGTGACTG TGATTCATCC 751                                                  800
H11-1  GAAGGGCACC AGTGCCGTGT CGAATGGAAT AGAAAAGGGA GAAGGAGAAG 801                                                  850
H11-1  TCTCTGGCGA TTGGGTCACA ACCAGATTCG ATCCAACCCC GCGAATGCCT 851                                                  900
H11-1  TCGTATTTGA TTGCTCTTGT GATTCCGAA TTTAAGTACA TTGAAAATTA 901                                                  950
AustB1                                  AATTCC GGCTCGTCCG GAAGCTATGA
H11-1  TACGAAAAGC GGTGTTCGAT TCCGAATTCC GGCTCGTCCG GAAGCTATGA
```

FIG. 5

```
                951                                                 1000
AustB1  AGATGACAGA ATATGCCATG ATAGCTGGAA TCAAATGTTT GGATTACTAT
H11-1   AGATGACAGA ATATGCCATG ATAGCTGGAA TCAAATGTTT GGATTACTAT 1001                                                 1050
AustB1  GAGGACTTCT TCGGGATCAA ATTCCCACTT CCAAAACAAG ATATGGTTGC
H11-1   GAGGACTTCT TCGGGATCAA ATTCCCACTT CCAAAACAAG ATATGGTTGC 1051                                                 1100
AustB1  TCTTCCTGAC TTCTCATCTG GTGCTATGGA GAACTGGGGT CTCATCACAT
H11-1   TCTTCCTGAC TTCTCATCTG GTGCTATGGA GAACTGGGGT CTCATCACAT 1101                                                 1150
AustB1  ACAGGGAGGG TTCCGTGCTC TACGATGAAA ACCTCTACGG ACCAATGAAT
H11-1   ACAGGGAGGG TTCCGTGCTC TACGATGAAA ACCTCTACGG ACCAATGAAT 1151                                                 1200
AustB1  AAGGAGCGGG TTGCAGAAGT GATCGCGCAC GAACTTGCAC ATCAGTGGTT
H11-1   AAGGAGCGGG TTGCAGAAGT GATCGCGCAC GAACTTGCAC ATCAGTGGTT 1201                                                 1250
AustB1  CGGTAATTTG GTCACGATGA AGTGGTGGGA TAACCTATGG CTGAACGAAG
H11-1   CGGTAATTTG GTCACGATGA AGTGGTGGGA TAACCTATGG CTGAACGAAG 1251                                                 1300
AustB1  GATTCGCGTC ATTCGTGGAA TACATCGGAG CCGACTTCAT CAGCGATGGT
H11-1   GATTCGCGTC ATTCGTGGAA TACATCGGAG CCGACTTCAT CAGCGATGGT 1301                                                 1350
AustB1  CTATGGGAAA TGAAAGATTT CTTCCTGCTG GCACCGTACA CAAGTGGTAT
H11-1   CTATGGGAAA TGAAAGATTT CTTCCTGCTG GCACCGTACA CAAGTGGTAT 1351                                                 1400
AustB1  TACGGCTGAT GCAGTAGCTT CAAGCCATCC GCTTTCCTTC AGAATAGATA
H11-1   TACGGCTGAT GCAGTAGCTT CAAGCCATCC GCTTTCCTTC AGAATAGATA 1401                                                 1450
AustB1  AGGCTGCAGA TGTATCAGAA GCGTTCGATG ATATCACATA CCGTAAAGGA
H11-1   AGGCTGCAGA TGTATCAGAA GCGTTCGATG ATATCACATA CCGTAAAGGA 1451                                                 1500
AustB1  GCATCCGTTC TTCAAATGCT ATTGAATTTA GTTGGGGACG AAAATTTCAA
H11-1   GCATCCGTTC TTCAAATGCT ATTGAATTTA GTTGGGGACG AAAATTTCAA 1501                                                 1550
AustB1  GCAGTCTGTT TCGCGTTACC TCAAGAAGTT TTCATATGAT AATGCGGCTG
H11-1   GCAGTCTGTT TCGCGTTACC TCAAGAAGTT TTCATATGAT AATGCGGCTG 1551                                                 1600
AustB1  CTGAAGATTT ATGGGCAGCA TTCGACGAAA CCGTCCAAGG TATAACCGGA
H11-1   CTGAAGATTT ATGGGCAGCA TTCGACGAAA CCGTCCAAGG TATAACCGGA 1601                                                 1650
AustB1  CCTAATGGTG GACCATTGAA AATGTCCGAG TTTGCGCCAC AATGGACAAC
H11-1   CCTAATGGTG GACCATTGAA AATGTCCGAG TTTGCGCCAC AATGGACAAC 1651                                                 1700
AustB1  TCAGATGGGG TTCCCTGTTC TTACTGTCGA GTCGGTTAAC GCAACGACTT
```

FIG. 5 (contd)

```
H11-1     TCAGATGGGG TTCCCTGTTC TTACTGTCGA GTCGGTTAAC GCAACGACTT 1701                                                    1750
AustB1    TGAAAGTCAC CCAAAAACGA TACAGGCAGA ACAAGGATGC AAAGGAACCA
H11-1     TGAAAGTCAC CCAAAAACGA TACAGGCAGA ACAAGGATGC AAAGGAACCA 1751                                                    1800
AustB1    GAGAAGTACC GTCATCCAAC TTATGGGTTC AAATGGGATG TTCCTCTGTG
H11-1     GAGAAGTACC GTCATCCAAC TTATGGGTTC AAATGGGATG TTCCTCTGTG 1801                                                    1850
AustB1    GTATCAGGAA GATGAACAGC AAGTGAAAAG AACTTGGTTA AAAAGAGAGG
H11-1     GTATCAGGAA GATGAACAGC AAGTGAAAAG AACTTGGTTA AAAAGAGAGG 1851                                                    1900
AustB1    AACCGCTCTA TTTCCATGTA AGCAATTCTG ATTCGTCAGT TGTGGTGAAT
H11-1     AACCGCTCTA TTTCCATGTA AGCAATTCTG ATTCGTCAGT TGTGGTGAAT 1901                                                    1950
AustB1    GCCGAACGTC GTGCTTTTTG CCGATCAAAC TATGACGCTA ACGGTTGGAG
H11-1     GCCGAACGTC GTGCTTTTTG CCGATCAAAC TATGACGCTA ACGGTTGGAG 1951                                                    2000
AustB1    GAACATTATG AGAAGACTCA AGCAGAATCA TAAGGTCTAT GGTCCACGAA
H11-1     GAACATTATG AGAAGACTCA AGCAGAATCA TAAGGTCTAT GGTCCACGAA 2001                                                    2050
AustB1    CAAGAAACGC TCTCATAAGT GATGCGTTTG CAGCAGCTGC AGTTGAGGAA
H11-1     CAAGAAACGC TCTCATAAGT GATGCGTTTG CAGCAGCTGC AGTTGAGGAA 2051                                                    2100
AustB1    ATGAATTACG AGACCGTATT TGAAATGCTC AAATACACCG TGAAAGAAGA
H11-1     ATGAATTACG AGACCGTATT TGAAATGCTC AAATACACCG TGAAAGAAGA 2101                                                    2150
AustB1    GGATTACTTA CCATGGAAGG AGGCAATATC AGGATTCAAT ACAATTTTGG
B1a                                      GCAATATC AGGATTCAAT ACAATTTTGG
H11-1     GGATTACTTA CCATGGAAGG AGGCAATATC AGGATTCAAT ACAATTTTGG 2151                                                    2200
AustB1    ACTTTTTCGG CAGCGAACCC GAATCTCAAT GGGCTTCGGA ATACATGCGA
B1a       ACTTTTTCGG CAGCGAACCC GAATCTCAAT GGGCTTCGGA ATACATGCGA
H11-1     ACTTTTTCGG CAGCGAACCC GAATCTCAAT GGGCTTCGGA ATACATGCGA 2201                                                    2250
AustB1    AAACTGATGA AGCCAATTTA TGACAAGAGT AGCATCAAGT TTATAGCGGA
B1a       AAACTGATGA AGCCAATTTA TGACAAGAGT AGCATCAAGT TTATAGCGGA
H11-1     AAACTGATGA AGCCAATTTA TGACAAGAGT AGCATCAAGT TTATAGCGGA 2251                                                    2300
AustB1    GAACTACAAA AAAGATTCGC TTTTCTTCAA AAATAATCTC CAAATAGCTG
B1a       GAACTACAAA AAAGATTCGC TTTTCTTCAA AAATAATCTC CAAATAGCTG
H11-1     GAACTACAAA AAAGATTCGC TTTTCTTCAA AAATAATCTC CAAATAGCTG 2301                                                    2350
AustB1    TTATTGACAC ATACTGTGGT CTTGGAGGCA AGAATGTCT TGAAGAAATG
B1a       TTATTGACAC ATACTGTGGT CTTGGAGGCA AGAATGTCT TGAAGAAATG
H11-1     TTATTGACAC ATACTGTGGT CTTGGAGGCA AGAATGTCT TGAAGAAATG
```

FIG. 5 (contd)

```
              2351                                                    2400
AustB1   AAAAAGCTTT TTGACAAGGA GGTCATGAAA TGTCAACCTG GTCAGCAAGC
   B1a   AAAAAGCTTT TTGACAAGGA GGTCATGAAA TGTCAACCTG GTCAGCAAGC
  H11-1  AAAAAGCTTT TTGACAAGGA GGTCATGAAA TGTCAACCTG GTCAGCAAGC 2401                                                    2450
AustB1   GACCGACTGC GTAAAGGTAA CTGCTCCTCT CCGAAAAACT GTTTACTGCT
   B1a   GACCGACTGC GTAAAGGTAA CTGCTCCTCT CCGAAAAACT GTTTACTGCT
  H11-1  GACCGACTGC GTAAAGGTAA CTGCTCCTCT CCGAAAAACT GTTTACTGCT 2451                                                    2500
AustB1   ATGGGGTCCA GGAAGGCGGT GATGAGGCAT TCGACAAGGT GATGGAACTA
   B1a   ATGGGGTCCA GGAAGGCGGT GATGAGGCAT TCGACAAGGT GATGGAACTA
  H11-1  ATGGGGTCCA GGAAGGCGGT GATGAGGCAT TCGACAAGGT GATGGAACTA 2501                                                    2550
AustB1   TATAATGCGG AACAAGTGCA GTTGGAGAAA GACAGTCTAC GTGAAGCATT
   B1a   TATAATGCGG AACAAGTGCA GTTGGAGAAA GACAGTCTAC GTGAAGCATT
  H11-1  TATAATGCGG AACAAGTGCA GTTGGAGAAA GACAGTCTAC GTGAAGCATT 2551                                                    2600
AustB1   GGGATGCCAT AAAGACGTTA CAGCTCTAAA GGGACTTCTT ATGCTGGCTT
   B1a   GGGATGCCAT AAAGACGTTA CAGCTCTAAA GGGACTTCTT ATGCTGGCTT
  H11-1  GGGATGCCAT AAAGACGTTA CAGCTCTAAA GGGACTTCTT ATGCTGGCTT 2601                                                    2650
AustB1   TGGATCGGAA TTC
   B1a   TGGATC
  H11-1  TGGATCGGAA TTCGTCATTT GTGCGTCTTC AAGATGCTCA TGATGTGTTT 2651                                                    2700
  H11-1  AACATTGTAT CCAGAAATCC TGTTGGAAAC GAACTGCTGT TCAATTTCCT 2701                                                    2750
  H11-1  CACAGAGCGA TGGGAAGAGA TACTTGAAAG TTTGTCAATA CGACACAGAT 2751                                                    2800
  H11-1  CAGTTGATCG AGTGATCAAA GCCTGTACTC GAGGACTACG ATCCAGGGAA 2801                                                    2850
  H11-1  CAAGTACAAC AGTTGAAGAA TCTATACAAA AATGACAAGC GTGCTCGCGA 2851                                                    2900
  H11-1  ATACGGTGCA TTTGGTGGGG CAATAGAAAG ATCGGAACAC AGAGTCAAAT 2901                                                    2950
  H11-1  GGATTGAGAA ACATTTCCGA AAACTAGCAG CTTTCTTCAA AAAATCTAAT 2951                                                    3000
  H11-1  TCATAATTCT GAAATGGCTA TAACTAGCAC ACTGGATAGT TGTCTCGAAT 3001                                                    3050
  H11-1  CATCCAAAAA GATTAATGAT GTTTTTTTAC TAGATAATAT GGAGATATTC 3051                    3084
  H11-1  TGTAAATTTG TCATCGATTC AAGTGTCTGT ATTG
```

MTAEESQEQETQQPRKNTVLRLTPIKSLFALLVVAAAVGLSIGLTYYFTRKAFDTTGGNGKGDQPIVDDNSPSAEELRLPTTIKPLTYDLVIKTYLPNYV

NYPPEKDFAIDGTVVIAMEVVEPTKSIVLNSKNIPVIADQCELFSNNQKLDIEKVVDQPRLEKVEFVLKKKLEKNQKITLKIVYIGLINDMLGGLYRTTY

TDKDGTTKIAACTHMEPTDARLMVPCFDEPTFKANWTVTVIHPKGTSAVSNGIEKGEGEVSGDWVTTRFDPTPRMPSYLIALVISEFFKYIENYTKSGVRF

RIPARPEAMKGTEYAMIAGIKCLDYEDFFGIKFPLPKQDMVALPDFSSGAMENWGLITYREGSVLYDENLYGPMNKERVAEVIAHELAHQWFGNLVTMK

WWDNLWLNEGFASFVEYIGADFISDGLWEMQDFFLLAPYTSGITADAVASSHPLSFRIDKAADVSEAFDDITYRKGASVLQMLLNLVGDENFKQSVSRYL

KKFSYDNAAAEDLWAAFDETVQGITGPNGGPLKMSEFAPQWTTQMGFPVLTVESVNATTLKVTQKRYRQNKDAKEPEKYRHPTYGFKWDVPLWYQEDEQQ
                                                                                    |||||||||
Pep.B                                                                                        MGFPVLTVES

VKRTWLKREEPLYFHVSNSDSSVVVNAERRAFCRSNYDANGWRNIMRRLKQNHKVYGPRTRNALISDAFAAAVEEMNYETVFEMLKYTVKEEDYLPWKE

AISGFNTILDFFGSEPESQWASEYMRKLMKPIYDKSSIKFIAENYKDSLFFKNNLQIAVIDTYCGLGGKECLEEMKGLFDKEVMKCQPGQQATDCVKVT

APLRKTVYCYGVQEGGDEAFDKMELYNAEQVQLEKDSLREALGCHKDVTALKGLLMLALDRNSFVRLQDAHDVFNIVSRNPVGNELLFNFLTERWEEI
                                                                                   |||| ||
Pep.C                                                                                    MLALDYHSXFV

LESLSIRHRSVDRVIKACTRGLRSREQVQQLRNLYKNDKRAREYGAFGGAIERSEHRVWIEKHFRKLAAFFKKSNS*

FIG. 7a

```
                    10         20         30         40         50         60         70         80         90        100
                     .          .          .          .          .          .          .          .          .          .
          MTAEWQKRRILGFSPISLLCTLFVLAAAVGLSIGLTYYFTRKAFDTTQKEQKDDSGGKEKDNSPSAEELLLPTNIKPVSYDLNIKTYLPQYVNFPPEKNL
                                                                |||||||||||||||||||||:|::||||
                                                                DNSPSAEELLLPTNIKPVSYDLKIATYLPG
SEQ ID NO: 16

110        120        130        140        150        160        170        180        190        200
            .          .          .          .          .          .          .          .          .          .
          TFDAHVEIAMVVVEPTNSIVLNSKKITLAQGGCELFSGNQKLDIESVKMQERLDKLEITLKNQLQKDLKILLKITYTGLISDTLGGLYQSIYTDKGKTK 210        220        230        240        250        260        270        280        290        300
            .          .          .          .          .          .          .          .          .          .
          IVAVSQNEPSDARRIAPCFDEPKYKATWTVTVHPKGTKAASNGIEANGKGELKGDWITSKFKTTPMSSYLLAIIVCEFEYIEGFTKTGVRFRIWSRPE 310        320        330        340        350        360        370        380        390        400
            .          .          .          .          .          .          .          .          .          .
          AKRMTAYALDAGIRCLEFYEKFFDIKFPLEKQDMIALPDFTAGAMENWGLITYREDSLLYDEKIYAPMNKQRVALVVAHELAHQWFGNLVTLKWWDDTWL
                                                          ||||||||||:|||
                                                          LAYDEKSYAPDNKQY
SEQ ID NO: 18

410        420        430        440        450        460        470        480        490        500
            .          .          .          .          .          .          .          .          .          .
          NEGFATFVEYLGMDEISHNNFRTQDFFLLDGMDRGMRADSAASSHPLSFRIDKAAEVAEAFDISYAKGASVLTMLRALIGEDNYRNAVVQYLKKFSYSN
                                                          ||||||:|::||
                                                          KAAEVAEAFDXIXXXKG 510        520        530        540        550        560        570        580        590        600
            .          .          .          .          .          .          .          .          .          .
          AQAADLWNVFNEVVKGVKGPDGNVMKIDQFTDQWTYQMGYPVVKVEEFNATALKVTQSRYKTNKDALEPEKYRNPKYGFKWDVPLWYQEGNSKEVKRTWL
                                   |||||||||||||| ||||
                                   MGYPVVKVEEFXATAL
Pep D 610        620        630        640        650        660        670        680        690        700
            .          .          .          .          .          .          .          .          .          .
          KRDEPLYLNVNRDTSLVVNADRHGFYRQNYDANGWKKIIKQLKKDHKVFGPRTRNAIISDAFAAATIDAIDYETVPELLEYAKNEEEFLPWKEALSGMF
Pep A 710        720        730        740        750        760        770        780        790        800
            .          .          .          .          .          .          .          .          .          .
          AVLKFFGNEPETKPARAYMMSILEPMYNKSSIDYIVNYLDDTLFTKINTQKDIIDAYCSLGSKDCIKQYKDIFYDEVMPKCKAGEAATKCVV3APLRA 810        820        830        840        850        860        870        880        890        900
            .          .          .          .          .          .          .          .          .          .
          NVYCYGVQEGGEEAFEKVMGLYLAEDVQLEKGILFKALACHKDVTALKELLLRALDRKSSFVRLQDVPTAFRAVSENPVGEEFMFNFLMERWEEITASLE
                                    ||||||:|| ||||
                                    LYLAEDVQLKKGILF
SEQ ID NO: 17

910        920        930        940        950        960        970
            .          .          .          .          .          .          .
          TEHRAVDKVVGACCTGIRSQQQIDQLKNLQKNNAQACKFGSFTQBIEKGEHKIAWIKKHFHRLSEFFKRARS*
```

FIG. 7b

```
Pep E
           10        20        30        40        50        60        70        80        90       100
            .         .         .         .         .         .         .         .         .         .
     MTSQGRTRTLLNLTPIRLIVALFLVAAAVGLSIGLTYYFTRKAFDTSEKPGKDDTGGKDKDNSPSAAELLLPSNIKPLSYDLTIKTYLPGYVDFPPEKNL 110       120       130       140       150       160       170       180       190       200
            .         .         .         .         .         .         .         .         .         .
     TFDGRVEISMVVIEPTKSIVLNSKKISVIPQECELVSGDKKLEIESVKEHPRLEKVEFLIKSQLEKDQQILLKVGYIGLISNSFGGIYQTTYTTPDGTPK 210       220       230       240       250       260       270       280       290       300
            .         .         .         .         .         .         .         .         .         .
     IAAVSQNEPIDARRMVPCMDEPKYKANWTVTVIHPKGTKAVSNGIEVNGDGEISGDWITSKFLTTPRMSSYLLAVMVSEFEYIEGETKTGVRFRIWSRPE 310       320       330       340       350       360       370       380       390       400
            .         .         .         .         .         .         .         .         .         .
     AKKMTQYALQSGIKCIEFYEDFFDIRFPLKKQDMIALPDFSAGAMENWGLITYRENSLLYDDRFYAPMNKQRIARIVAHELAHQWFGDLVTMKWWDNLWL 410       420       430       440       450       460       470       480       490       500
            .         .         .         .         .         .         .         .         .         .
     NEGFARFTEFIGAGQITQDDARMRNYFLIDVLERALKADSVASSHPLSFRIDKAAEVEEAFDDITYAKGASVLTMLRALIGEEKHKHAVSQYLKKFSYSN
                                                        ||:|:|||||||:|::|
                                                        KAVEVAEAFDDITYXXGPS 510       520       530       540       550       560       570       580       590       600
            .         .         .         .         .         .         .         .         .         .
     AEATDLWAVFDEVTDVEGPDGKPMKTTEFASQWTTQMGFPVISVAEFNSTTLKLTQSRYEANKDAVEKEKYRHPKCYGFKWDIPLWYQEGDKKEIKRTWL 610       620       630       640       650       660       670       680       690       700
            .         .         .         .         .         .         .         .         .         .
     RRDEPLYLHVSDAGAPFVVNADRYGFYRQNHDANGWKKIIKQLKDNHEVYSPRTRNVIISDAFAAAATDAIEYETVFELLNYAEKETEYLPLEIAMSGIS 710       720       730       740       750       760       770       780       790       800
            .         .         .         .         .         .         .         .         .         .
     SILKYFPTEPEAKPAQTYMMNILKPMYEKSSIDFIANNYRNDKLFFQINLQKDVIDMFCALGSQDCRRKYKLFDDEVMRKCRDGQAATECVRIAAPLRS 810       820       830       840       850       860       870       880       890       900
            .         .         .         .         .         .         .         .         .         .
     SVYCYGVKEGGDYASDKVMELYTAETLALEKDFLRLALGCHKDVTALKGLLLRALDRNSSFVRMQDIPSAFNDVAANPIGEEFIFNFLIERWPDIIESIG 910       920       930       940       950       960       970
            .         .         .         .         .         .         .
     TKHTYVEKVIPACTSGIRSQQQIDQLKNLQKNGMNARQFGAFDKAIERAQNRVDWIKKHFQKLAAFFKKATL*
```

FIG. 7c

P = POLYHEDRIN PROMOTER

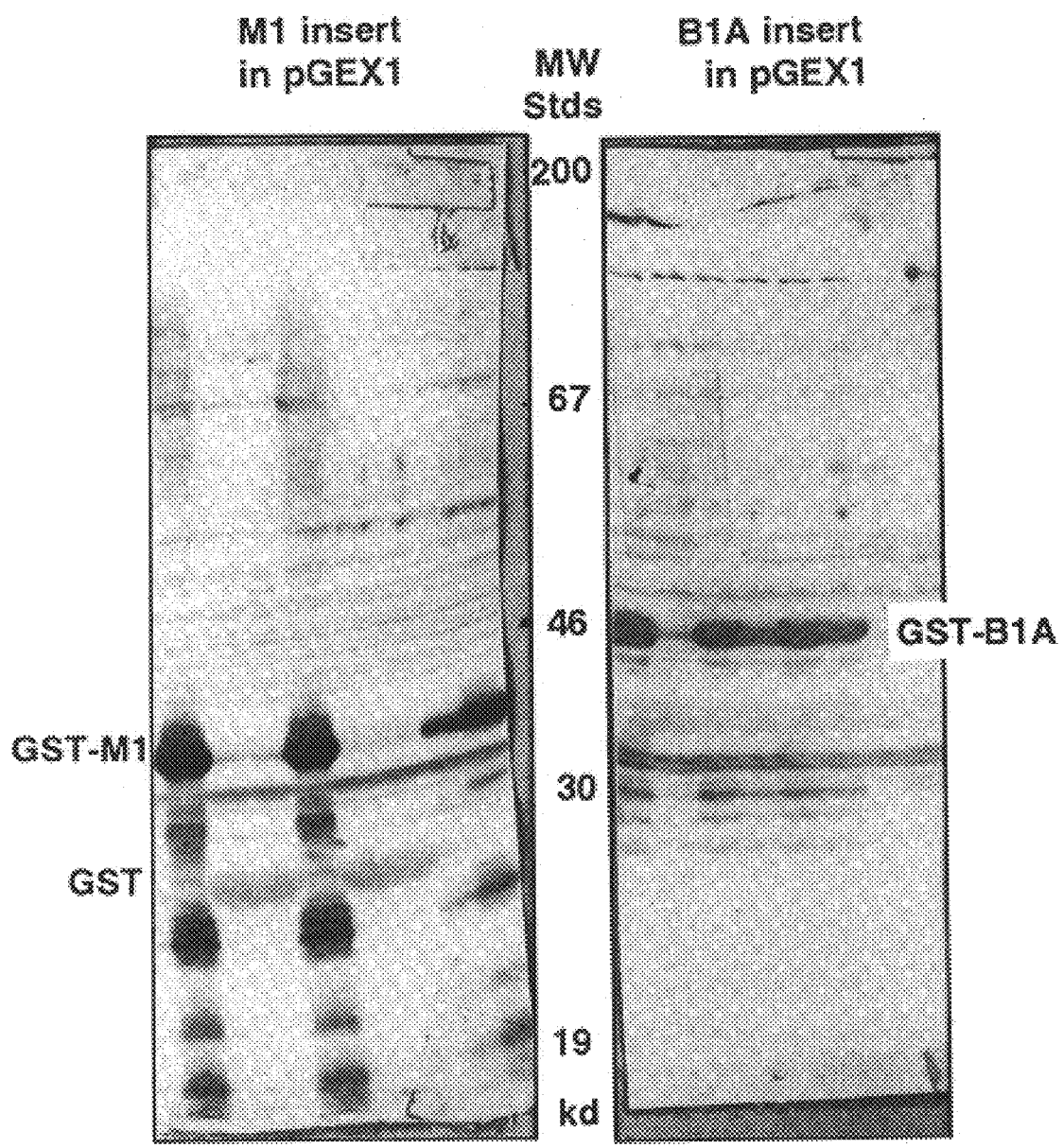

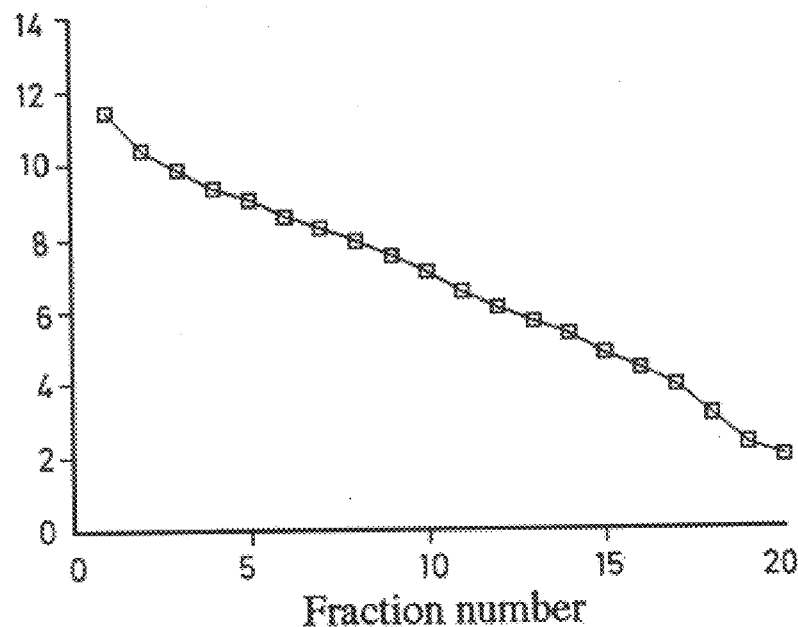
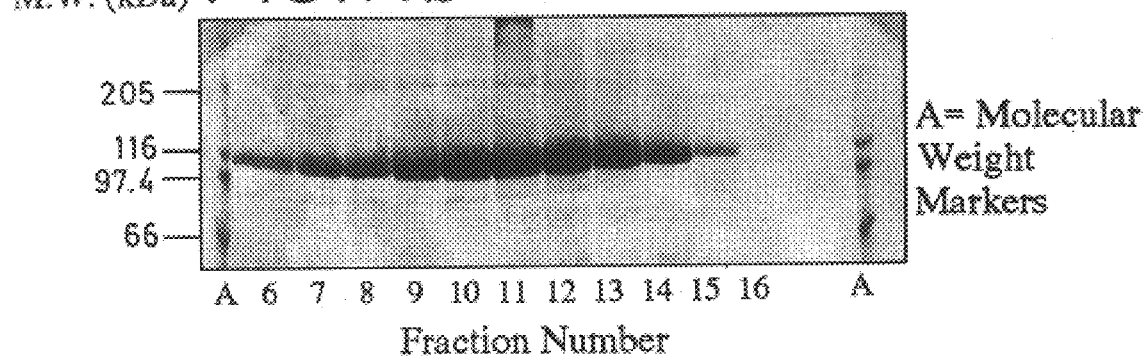
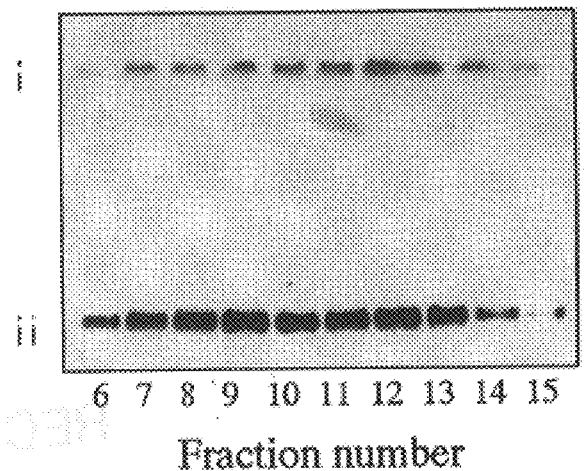

A = Molecular Weight Markers
B = ConA H110D starting material

Mean parasite eggs per gram faeces

D = RF3 Doublet
L = Lower band
U = Upper band
C = Controls

Numbers of male and female worms present at post-mortem

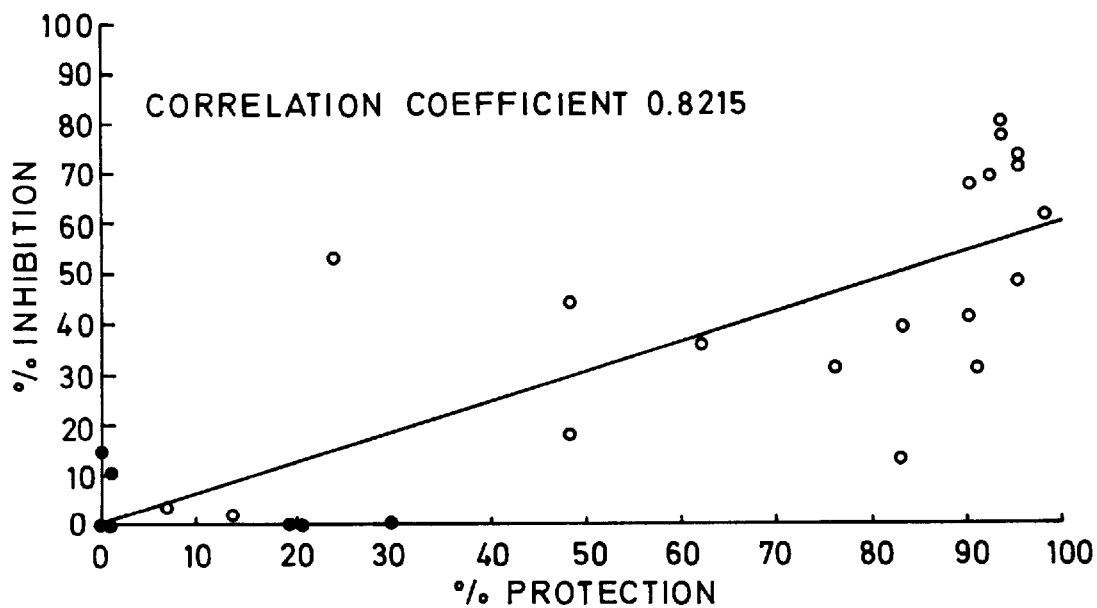
FIG. 18a)i
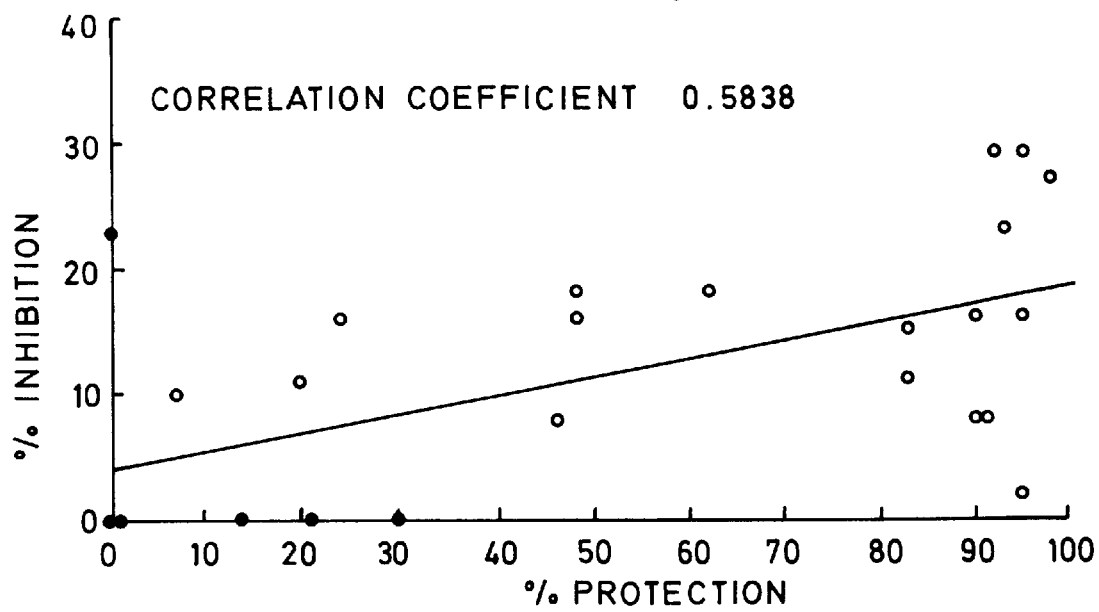
FIG. 18a)ii

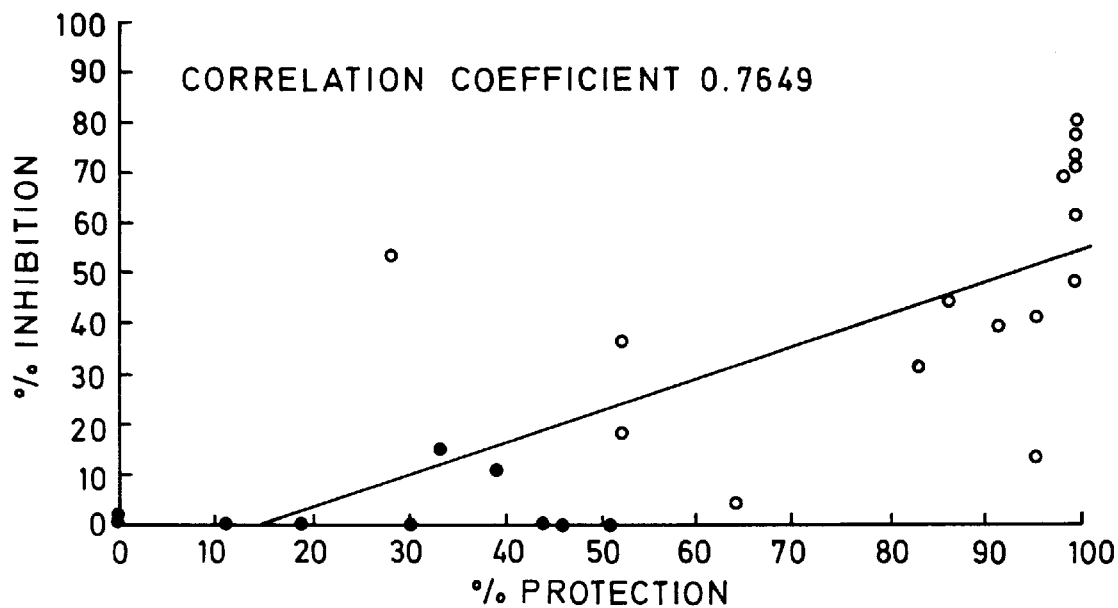
FIG. 18b)i
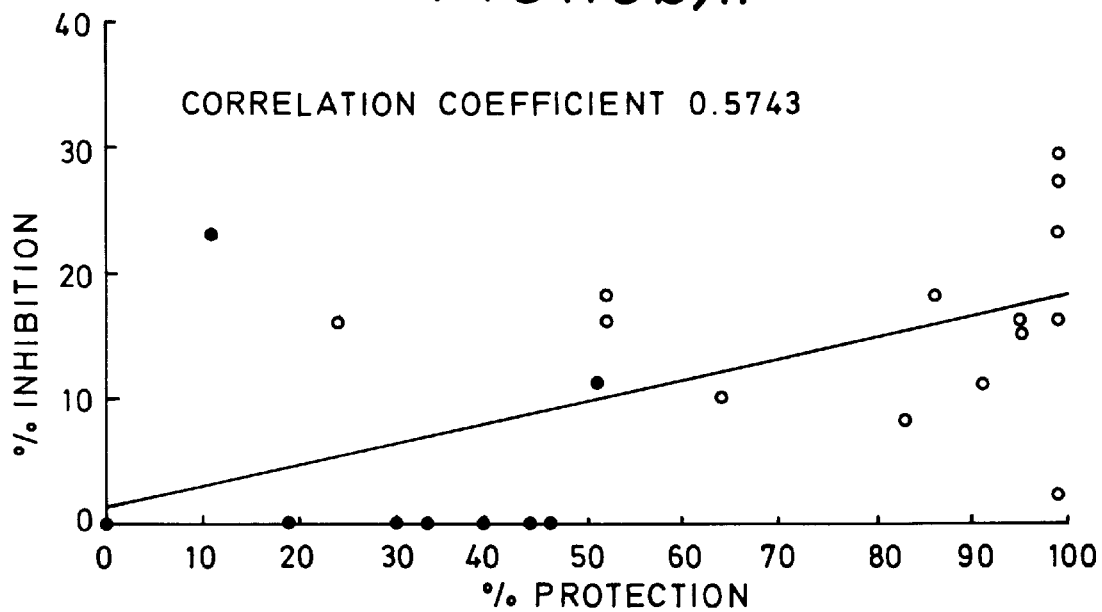
FIG. 18b)ii

SEQUENCE LISTING (1) GENERAL INFORMATION:

(iii) NUMBER OF SEQUENCES: 73

(2) INFORMATION FOR SEQ ID NO:1:

(i) SEQUENCE CHARACTERISTICS:
      (A) LENGTH: 295 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
CGCGGACATT GCTGAATCTA ACTCCAATCC GTCTTATTGT CGCATTATTT CTAGTAGCTG      60

CTGCAGTCGG CCTCTCTATT GGTCTCACCT ATTACTTTAC TCGCAAAGCG TTCGATACCT     120

CAGAAAAGCC AGGGAAGGAT GATACTGGTG GCAAGGACAA AGACAATTCT CCCTCTGCGG     180

CGGAACTACT TCTTCCAAGT AATATAAAAC CATTGTCTTA CGACTTGACG ATCAAAACAT     240

ATCTACCTGG TTATGTGGAC TTCCCACCGG AGAAAAACCT CACATTCGAC GGGCG          295
```

(2) INFORMATION FOR SEQ ID NO:2:

(i) SEQUENCE CHARACTERISTICS:
      (A) LENGTH: 484 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (xi) SEQUENCE DESCRIPTION: SEQ ID NO:2:

```
GCAATATCAG GATTCAATAC AATTTTGGAC TTTTTCGGCA GCGAACCCGA ATCTCAATGG      60

GCTTCGGAAT ACATGCGAAA ACTGATGAAG CCAATTTATG ACAAGAGTAG CATCAAGTTT     120

ATAGCGGAGA ACTACAAAAA AGATTCGCTT TTCTTCAAAA ATAATCTCCA AATAGCTGTT     180
```

```
ATTGACACAT ACTGTGGTCT TGGAGGCAAA GAATGTCTTG AAGAAATGAA AAAGCTTTTT      240

GACAAGGAGG TCATGAAATG TCAACCTGGT CAGCAAGCGA CCGACTGCGT AAAGGTAACT      300

GCTCCTCTCC GAAAAACTGT TTACTGCTAT GGGGTCCAGG AAGGCGGTGA TGAGGCATTC      360

GACAAGGTGA TGGAACTATA TAATGCGGAA CAAGTGCAGT TGGAGAAAGA CAGTCTACGT      420

GAAGCATTGG GATGCCATAA AGACGTTACA GCTCTAAAGG GACTTCTTAT GCTGGCTTTG      480

GATC                                                                   484

(2) INFORMATION FOR SEQ ID NO:3:

(i) SEQUENCE CHARACTERISTICS:
        (A) LENGTH: 216 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

ACCTGGTCAG CAAGCGACCG ACTGCGTAAA GGTAACTGCT CCTCTCAAAA CTGTTTACTG       60

CTATGGGGTC CAGGAAGGCG GTGATGAGGC ATTCGACAAG GTGATGGAAC TATATAATGC      120

GGAACAAGTG CAGTTGGAGA AAGACAGTCT ACGTGAAGCA TTGGGATGCC ATAAAGACGT      180

TACAGCTCTA AAGGGACTTC TTATGCTGGC TTTGGA                                216

(2) INFORMATION FOR SEQ ID NO:4:

(i) SEQUENCE CHARACTERISTICS:
        (A) LENGTH: 581 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

GGGAGGAAAT CACTGCGAGC TTGGAAACAG AACACAGAGC AGTTGATAAA GTGGTCGGCG       60

CTTGTTGCAC AGGAATTCGC TCCCAACAAC AAATAGATCA GCTGAAGAAG AATCTACAGA      120

AGAACAATGC GCAGGCTAAG AAGTTCCATA AAATTGCCTG GATCAAGAAA CATTTTCACA      180

GATTATCGGA ATTCTTCAAG AGAGCAAGAT CATAGCTTTT CACACTGAGC TCCAATTTTA      240

ACGTCTTCAA ACTAGGAGAC AGTTTTGCTG AAAAGTCAGT TTCACATTTT CCGTTTGAAT      300

GCCATCCATT CGAATACAAC CAACCCCATT TTAAGTACCT TTCATTCACA GTGATTACTA      360

AATTTCGAAT ATATTATGAA GCTTGTATCT TGAACGTTAT GATCGGTGAC TTTCAATTTA      420

TAGAGCTCAC TCTCCATTTT GTAGCTGTGA TGACTTGCAT TTAAGACCCA CCATTTACCA      480

GCCTATAATC TTTCCCCAAT ACATTCCAAA CTCCGATCAC CTCCACCGCT GACAATGCCC      540

AGATTTGTTT CTTTGTCTGC TATCCATCTA ACTGTTTCGA T                          581

(2) INFORMATION FOR SEQ ID NO:5:

(i) SEQUENCE CHARACTERISTICS:
        (A) LENGTH: 948 base pairs
```

(B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

```
ATGACGTCGC AGGGGAGAAC GCGGACATTG CTGAATCTAA CTCCAATCCG TCTTATTGTC    60

GCATTATTTC TAGTAGCTGC TGCAGTCGGC CTCTCTATTG GTCTCACCTA TTACTTTACT   120

CGCAAAGCGT TCGATACCTC AGAAAAGCCA GGGAAGGATG ATACTGGTGG CAAGGACAAA   180

GACAATTCTC CCTCTGCGGC GGAACTACTC CTTCCAAGTA ATATAAAACC ATTGTCTTAC   240

GACTTGACGA TCAAAACATA TCTACCTGGT TATGTGGACT TCCCACCGGA GAAAAACCTC   300

ACATTCGATG GGCGTGTGGA AATATCAATG GTTGTAATTG AGCCAACAAA GAGTATCGTA   360

CTCAATTCAA AGAAGATCTC TGTAATACCC AAGAATGTG AACTGGTATC GGGCGATAAA    420

AAATTCGAAA TTGAAAGTGT AAAGGAGCAC CCAAGACTGG AAAAGGTTGA GTTTCTTATC   480

AAAAGCCAAC TGGAAAAAGA TTCACAAATC TTGCTCAAGT CGGCTTACAT CGGTCTCATC   540

AGCAACAGCC TTGGTGGAAT CTACCAGACC ACTTATACCA CCCCGGATGG CACCCCTAAG   600

ATCGCTGCAG TTTCACAAAA TGAGCCCATA GATGCTCGTC GAATGGTACC ATGCATGGAT   660

GAACCGAAAT ACAAAGCAAA CTGGACCGTT ACTGTCATTA TCCAAAAGG CACCAAAGCC    720

GTCTCGAATG GAATCGAAGT GAACGGAGAT GGAGAGATCA GTGGTGATTG GATCACATCG   780

AAGTTCTTGA CTACTCCACG GATGTCATCC TACTTGTTGG CAGTTATGGT TTCAGAATTT   840

GAATACATCG AAGGTGAAAC AAAGACGGGT GTTCGGTTCC GTATATGGTC ACGCCCAGAG   900

GCAAAGAAGA TGACACAATA TGCTCTGCAA TCTGGTATCA AGTGCATA              948
```

(2) INFORMATION FOR SEQ ID NO:6:

(i) SEQUENCE CHARACTERISTICS:
        (A) LENGTH: 1689 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:6:

```
AATTCCGGCT CGTCCGGAAG CTATGAAGAT GACAGAATAT GCCATGATAG CTGGAATCAA    60

ATGTTTGGAT TACTATGAGG ACTTCTTCGG GATCAAATTC CCACTTCCAA AACAAGATAT   120

GGTTGCTCTT CCTGACTTCT CATCTGGTGC TATGGAGAAC TGGGGTCTCA TCACATACAG   180

GGAGGGTTCC GTGCTCTACG ATGAAAACCT CTACGGACCA ATGAATAAGG AGCGGGTTGC   240

AGAAGTGATC GCGCACGAAC TTGCACATCA GTGGTTCGGT AATTTGGTCA CGATGAAGTG   300

GTGGGATAAC CTATGGCTGA ACGAAGGATT CGCGTCATTC GTGGAATACA TCGGAGCCGA   360

CTTCATCAGC GATGGTCTAT GGGAAATGAA AGATTTCTTC CTGCTGGCAC CGTACACAAG   420

TGGTATTACG GCTGATGCAG TAGCTTCAAG CCATCCGCTT TCCTTCAGAA TAGATAAGGC   480

TGCAGATGTA TCAGAAGCGT TCGATGATAT CACATACCGT AAAGGAGCAT CCGTTCTTCA   540
```

```
AATGCTATTG AATTTAGTTG GGGACGAAAA TTTCAAGCAG TCTGTTTCGC GTTACCTCAA    600

GAAGTTTTCA TATGATAATG CGGCTGCTGA AGATTTATGG GCAGCATTCG ACGAAACCGT    660

CCAAGGTATA ACCGGACCTA ATGGTGGACC ATTGAAAATG TCCGAGTTTG CGCCACAATG    720

GACAACTCAG ATGGGGTTCC CTGTTCTTAC TGTCGAGTCG GTTAACGCAA CGACTTTGAA    780

AGTCACCCAA AAACGATACA GGCAGAACAA GGATGCAAAG GAACCAGAGA AGTACCGTCA    840

TCCAACTTAT GGGTTCAAAT GGGATGTTCC TCTGTGGTAT CAGGAAGATG AACAGCAAGT    900

GAAAAGAACT TGGTTAAAAA GAGAGGAACC GCTCTATTTC CATGTAAGCA ATTCTGATTC    960

GTCAGTTGTG GTGAATGCCG AACGTCGTGC TTTTTGCCGA TCAAACTATG ACGCTAACGG   1020

TTGGAGGAAC ATTATGAGAA GACTCAAGCA GAATCATAAG GTCTATGGTC CACGAACAAG   1080

AAACGCTCTC ATAAGTGATG CGTTTGCAGC AGCTGCAGTT GAGGAAATGA ATTACGAGAC   1140

CGTATTTGAA ATGCTCAAAT ACACCGTGAA AGAAGAGGAT TACTTACCAT GGAAGGAGGC   1200

AATATCAGGA TTCAATACAA TTTTGGACTT TTTCGGCAGC GAACCCGAAT CTCAATGGGC   1260

TTCGGAATAC ATGCGAAAAC TGATGAAGCC AATTTATGAC AAGAGTAGCA TCAAGTTTAT   1320

AGCGGAGAAC TACAAAAAAG ATTCGCTTTT CTTCAAAAAT AATCTCCAAA TAGCTGTTAT   1380

TGACACATAC TGTGGTCTTG GAGGCAAAGA ATGTCTTGAA GAAATGAAAA AGCTTTTTGA   1440

CAAGGAGGTC ATGAAATGTC AACCTGGTCA GCAAGCGACC GACTGCGTAA AGGTAACTGC   1500

TCCTCTCCGA AAAACTGTTT ACTGCTATGG GGTCCAGGAA GGCGGTGATG AGGCATTCGA   1560

CAAGGTGATG GAACTATATA ATGCGGAACA AGTGCAGTTG GAGAAAGACA GTCTACGTGA   1620

AGCATTGGGA TGCCATAAAG ACGTTACAGC TCTAAAGGGA CTTCTTATGC TGGCTTTGGA   1680

TCGGAATTC                                                          1689

(2) INFORMATION FOR SEQ ID NO:7:

(i) SEQUENCE CHARACTERISTICS:
        (A) LENGTH: 2472 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

ACGGGTGTTC GGTTCCGTAT ATGGTCTCGA CCAGAGGCGA AACGAATGAC GGCATACGCT     60

TTGGATGCTG GCATCAGATG CCTGGAGTTC TATGAGAAGT TCTTTGACAT AAAATTCCCT    120

CTGGAAAAAC AAGATATGAT TGCTCTTCCT GATTTCACCG CTGGTGCCAT GGAAAACTGG    180

GGCCTTATCA CTTATAGAGA GGATTCTCTC CTATACGATG AAAAAATTTA TGCACCGATG    240

AATAAACAGC GGGTTGCTCT CGTAGTTGCT CACGAGCTTG CTCATCAGTG GTTCGGCAAT    300

CTGGTCACAC TGAAGTGGTG GGATGATACG TGGTTGAACA AAGGTTTTGC AACATTTGTT    360

GAGTATCTTG GAATGGACGA AATTAGCCAC AACAATTTCA GAACGCAAGA TTTCTTCTTG    420

CTCGATGGAA TGGATCGCGG AATGAGAGCT GACTCGGCAG CATCGAGCCA TCCGCTTTCG    480

TTTAGGATTG ACAAAGCGGC AGAAGTTGCC GAAGCCTTTG ACGATATTTC ATACGCCAAG    540

GGAGCGTCAG TTCTCACTAT GCTACGGGCT TTGATTGGAG AGGACAATTA CAGGAATGCT    600

GTTGTGCAAT ACCTCAAGAA GTTCTCCTAC AGCAATGCAC AAGCAGCCGA TCTGTGGAAC    660
```

```
GTCTTCAATG AAGTTGTCAA AGGTGTTAAG GGTCCTGACG GCAACGTCAT GAAAATCGAC        720

CAATTTACCG ATCAGTGGAC GTATCAGATG GGTTATCCTG TGGTTAAAGT AGAAGAATTT        780

AATGCGACCG CCCTAAAGGT TACGCAGAGC CGGTACAAGA CAAATAAAGA CGCCTTGGAA        840

CCAGAGAAAT ATCGTAATCC AAAATACGGG TTCAAGTGGG ATGTTCCCCT ATGGTATCAG        900

GAAGGCAATA GCAAAGAGGT GAAGCGAACA TGGCTAAAAA GAGATGAACC GCTGTACTTG        960

AACGTCAACA ATCGGGATAC ATCCCTTGTG GTGAACGCTG ATCGACATGG ATTTTATCGA       1020

CAAAACTATG ATGCCAACGG TTGGAAAAAG ATAATCAAGC AGCTCAAGAA AGATCACAAG       1080

GTCTTCGGTC CAAGGACAAG GAACGCTATC ATAAGCGATG CATTTGCTGC AGCTACGATT       1140

GACGCAATCG ACTATGAAAC TGTATTCGAA CTACTTGAAT ATGCCAAAAA TGAAGAGGAA       1200

TTCTTGCCTT GGAAGGAAGC TCTGTCCGGC ATGTTCGCAG TTTTAAAGTT CTTCGGTAAT       1260

GAGCCGGAGA CAAAACCAGC TAGAGCTTAC ATGATGAGCA TATTAGAACC GATGTATAAT       1320

AAGAGCAGCA TTGATTACAT CGTCAAGAAT TATTTGGATG ATACGTTATT CACAAAAATT       1380

AATACTCAAA AGGATATCAT TGATGCATAT TGTTCCCTTG GATCAAAGGA CTGTATAAAG       1440

CAATATAAGG ATATCTTCTA CGATGAGGTT ATGCTCAAGT GTAAGGCCGG GGAAGCAGCA       1500

ACCAAATGCG TTAAGGTTTC CGCTCCTCTT CGAGCCAATG TTTACTGTTA TGGTGTACAG       1560

GAAGGTGGTG AAGAAGCTTT TGAAAAGGTG ATGGGGCTGT ATCTAGCAGA AGATGTTCAA       1620

CTGGAGAAGG GTATCCTGTT CAAAGCCTTG GCATGCCACA AAGATGTTAC AGCTCTAAAA       1680

GAACTTCTTT TGCGAGCCCT GGACCGTAAA TCGTCGTTTG TGCGTCTTCA GGATGTCCCT       1740

ACCGCTTTCC GTGCTGTATC TGAAAACCCT GTGGGCGAAG AATTCATGTT CAATTTCCTA       1800

ATGGAGAGAT GGGAGGAAAT CACTGCGAGC TTGGAAACAG AACACAGAGC AGTTGATAAA       1860

GTGGTCGGCG CTTGTTGCAC AGGAATTCGC TCCCAACAAC AAATAGATCA GCTGAAGAAT       1920

CTACAGAAGA ACAATGCGCA GGCTAAGAAG TTCGGCTCAT TCACCCAGGA AATCGAAAAA       1980

GGAGAACATA AAATTGCCTG GATCAAGAAA CATTTTCACA GATTATCGGA ATTCTTCAAG       2040

AGAGCAAGAT CATAGCTTTT CACACTGAGC TCCAATTTTA ACGTCTTCAA ACTAGGAGAC       2100

AGTTTTGCTG AAAAGTCAGT TTCACATTTT CCGTTTGAAT GCCATCCATT CGAATACAAC       2160

CAATAATACC ATTTTAAGTA CCTTTCATTC ACAGTGATTA CTGAATTTCG AATATATCAT       2220

GAAGCTTGTA TCTTGAACGT TATGATCGGT GACTTTCAAT TTATAGAGCT CACTCTCCAT       2280

TTTGTAGCTG TGATGACTTG CATTTAAGAC CCACCATTTA CCAGCCTAGA ATCTTTCCCC       2340

AATACATTCC AAACTCCGAT CACCTCCACC GCTGACAATG CCCAGATTTG TTTTTTTGTC       2400

TGCTATCCAT CTAACTGTTT CGATCGCCGG TTGTTTGTCA ATTGCTTATC TGATAAATAT       2460

TGACGTTGGT GT                                                           2472
```

(2) INFORMATION FOR SEQ ID NO:8:

(i) SEQUENCE CHARACTERISTICS:
        (A) LENGTH: 3305 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

-continued

```
GCTGAATCTA ACTCCAATCC GTCTTATTGT CGCATTATTT CTAGTAGCTG CTGCAGTCGG      60

CCTCTCTATT GGTCTCACCT ATTACTTTAC TCGCAAAGCG TTCGATACCT CAGAAAAGCC     120

AGGGAAGGAT GATACTGGTG GCAAGGACAA AGACAATTCT CCCTCTGCGG CGGAACTACT     180

CCTTCCAAGT AATATAAAAC CATTGTCTTA CGACTTGACG ATCAAAACAT ATCTACCTGG     240

TTATGTGGAC TTCCCACCGG AGAAAAACCT CACATTCGAT GGGCGTGTGG AAATATCAAT     300

GGTTGTAATT GAGCCAACAA AGAGTATCGT ACTCAATTCA AGAAGATCT CTGTAATACC      360

CCAAGAATGT GAACTGGTAT CGGGCGATAA AAAACTCGAA ATTGAAAGTG TAAAGGAGCA     420

CCCAAGACTG GAAAAGGTTG AGTTTCTTAT CAAAAGCCAA CTGGAAAAAG ATCAACAAAT     480

CTTGCTCAAG GTCGGCTACA TCGGTCTCAT CAGCAACAGC TTTGGTGGAA TCTACCAGAC     540

CACTTATACC ACCCCGGATG GCACCCCTAA GATCGCTGCA GTTTCACAAA ATGAGCCCAT     600

AGATGCTCGT CGAATGGTAC CATGCATGGA TGAACCGAAA TACAAAGCAA ACTGGACCGT     660

TACTGTCATT CATCCAAAAG GCACCAAAGC CGTCTCGAAT GGAATCGAAG TGAACGGAGA     720

TGGAGAGATC AGTGGTGATT GGATCACATC GAAGTTCTTG ACTACTCCAC GGATGTCATC     780

CTACTTGTTG GCAGTTATGG TTTCAGAATT TGAATACATC GAAGGTGAAA CAAAGACGGG     840

TGTTCGGTTC CGTATATGGT CACGCCCAGA GGCAAAGAAG ATGACACAAT ATGCTCTGCA     900

ATCTGGTATC AAGTGCATAG AATTCTACGA AGATTTCTTT GATATCAGAT TCCCTCTGAA     960

GAAACAAGAT ATGATTGCCC TTCCTGATTT CTCTGCCGGT GCCATGGAGA ATTGGGGCCT    1020

CATCACTTAC AGGGAAAACT CTTTGTTGTA CGATGACAGA TTCTATGCAC CGATGAATAA    1080

ACAGCGAATT GCTCGCATTG TTGCTCATGA GCTTGCTCAT CAGTGGTTCG GCGACTTGGT    1140

TACGATGAAG TGGTGGGATA ATTTGTGGTT GAATGAAGGT TTTGCAAGAT TCACAGAATT    1200

TATTGGAGCT GGTCAGATAA CTCAAGATGA CGCCAGAATG AGGAACTACT TCCTGATTGA    1260

TGTACTTGAA CGCGCTTTGA AAGCTGATTC GGTAGCGTCA AGCCATCCAC TTTCCTTCAG    1320

AATCGACAAA GCTGCAGAAG TTGAAGAAGC CTTTGATGAT ATCACATACG CCAAAGGAGC    1380

TTCTGTTCTT ACTATGCTGA GAGCCTTGAT TGGAGAAGAA AAACATAAGC ATGCAGTATC    1440

GCAGTACCTC AAGAAGTTCT CGTATAGCAA TGCAGAAGCG ACTGATCTAT GGGCAGTTTT    1500

TGATGAAGTT GTCACTGACG TCGAAGGTCC AGACGGCAAA CCTATGAAAA CCACAGAGTT    1560

TGCAAGTCAG TGGACGACTC AGATGGGCTT CCCAGTTATT TCCGTAGCAG AGTTTAACTC    1620

GACTACTTTG AAATTAACGC AAAGTCGATA TGAGGCGAAT AAAGACGCTG TGGAGAAAGA    1680

GAAGTACCGT CACCCGAAAT ACGGATTTAA ATGGGATATT CCACTGTGGT ATCAGGAAGG    1740

CGATAAGAAG GAGATAAAGC GAACATGGTT GAGAAGAGAT GAACCGCTTT ACTTGCATGT    1800

TAGTGATGCT GGCGCTCCCT TTGTGGTGAA CGCAGACCGC TATGGATTTT ATCGACAAAA    1860

TCATGACGCT AATGGTTGGA AAAGATAAT CAAGCAGCTC AAGGATAATC ATGAGGTTTA     1920

CAGTCCCCGG ACAAGGAATG TCATCATTAG CGATGCGTTT GCTGCGGCTG CAACTGACGC    1980

AATTGAGTAT GAGACTGTAT TTGAACTTCT GAATTATGCC GAAAAAGAAA CGGAATATCT    2040

ACCATTAGAA ATCGCAATGT CCGGGATCTC TTCGATTTTG AAATACTTCC CTACCGAGCC    2100

AGAGGCAAAG CCAGCTCAAA CATACATGAT GAACATATTG AAACCGATGT ATGAAAAAAG    2160

CAGTATCGAC TTCATTGCCA ATAACTACAG AAATGACAAG CTGTTTTTCC AAATCAACCT    2220

CCAAAAAGAT GTCATTGATA TGTTCTGCGC CCTCGGATCG CAAGACTGCA GGAAGAAATA    2280

TAAAAAACTT TTCGATGACG AAGTCATGAA CAAATGCAGG GATGGTCAAG CAGCAACCGA    2340

ATGCGTAAGA ATCGCCGCTC CTCTCCGATC AAGTGTTTAT TGTTATGGTG TGAAGGAAGG    2400
```

```
CGGTGATTAT GCTTCCGACA AGGTGATGGA GCTTTATACG GCCGAAACAC TCGCCCTAGA      2460

AAAAGACTTC CTACGCCTAG CATTGGGATG TCATAAAGAT GTTACTGCTT TGAAAGGACT      2520

TCTCTTGCGG GCTCTGGACA GGAATTCGTC GTTCGTACGT ATGCAGGATA TCCCAAGTGC      2580

TTTCAACGAT GTAGCAGCAA ATCCTATTGG CGAAGAATTC ATTTTCAATT TCCTTATTGA      2640

GAGATGGCCA GATATCATTG AAAGTATAGG AACGAAGCAC ACATATGTTG AGAAAGTGAT      2700

ACCAGCCTGC ACTTCAGGAA TCCGCTCACA ACAGCAGATT GACCAGCTGA AGAATCTGCA      2760

GAAAAATGGC ATGAACGCTC GTCAATTCGG TGCATTCGAT AAAGCAATCG AACGAGCACA      2820

AAATAGGGTG GATTGGATTA AAAAACATTT CCAAAAATTA GCGGCTTTCT TCAAGAAAGC      2880

CACCTTGTAA TTCGAATTAC ATTGCCAGTA ATCCAGATCT TAAAGTTCAT GAAGGAATAT      2940

GACAGGGAAC TGACTGTCTG TTGGTCACTG TTCCACTGAA TGGAAGTTTT TACCTACAAA      3000

AATTTTTATC GTTATATTTG CCTTCCGTGA GGGGTCATTG TTGTCACTTG AATAGTAAAC      3060

AAAGCTCAGT ATTGGCAACC GTAGAACAAT ATTACTTTCG CTTCATCAAA TTGTTATCTT      3120

CCCTATACCC TCTTCCTAAC TGAATTCGGA AATTTGTTCA TATTCGTTTG TAGTCTGTTG      3180

CTCAGAACAC TTTCTCCTCA ATAGCTTCTT GTTTGTTTTT TTTTTGATTG TATTGATCGT      3240

TTTACAATTG TATAGATTAG TTATCTTATA AATATTGATG GTTAAAAAAA AAAAAAAAA      3300

AAAAA                                                                 3305

(2) INFORMATION FOR SEQ ID NO:9:

(i) SEQUENCE CHARACTERISTICS:
        (A) LENGTH: 1301 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

GGTTTAATTA CCCAAGTTTG AGATGACAGC AGAGGAGAGT CAGGAGCAGG AGACGCAGCA       60

ACCACGAAAA AATACAGTGC TACGGCTCAC CCCAATCAAG TCTCTCTTTG CTTTGTTAGT      120

GGTAGCTGCT GCCGTCGGCC TCTCAATCGG TCTCACCTAT TACTTTACAA GGAAAGCTTT      180

TGATACTACT GGCGGAAATG GAAAAGGGGA TCAACCTATT GTCGATGATA ATTCCCCATC      240

AGCTGAAGAA TTACGTCTCC CAACAACCAT AAAACCTTTG ACATACGACT TAGTAATCAA      300

AACGTATCTG CCAAACTATG TAAACTATCC ACCTCAGAAA GATTTCGCTA TTGATGGGAC      360

TGTGGTGATT GCTATGGAAG TTGTGGAGCC AACAAAGTCT ATTGTGCTCA ACTCGAAAAA      420

TATTCCTGTA ATTGCAGACC AGTGCGAACT GTTTTCTAAC AACCAAAAAC TCGACATCGA      480

AAAGGTTGTG GATCAGCCAA GGCTGGAGAA AGTCGAATTC GTTTTGAAGA AAAAGCTGGA      540

GAAGAATCAG AAAATCACGC TCAAGATTGT ATACATTGGC CTTATCAACG ACATGCTTGG      600

AGGACTTTAT CGAACAACCT ACACGGATAA AGATGGTACA ACCAAGATTG CTGCATGCAC      660

TCATATGGAA CCGACGGACG CCCGTCTTAT GGTCCCCTGT TTCGACGAGC CGACGTTTAA      720

GGCAAACTGG ACTGTGACTG TGATTCATCC GAAGGGCACC AGTGCCGTGT CGAATGGAAT      780

AGAAAAGGGA GAAGGAGAAG TCTCTGGCGA TTGGGTCACA ACCAGATTCG ATCCAACCCC      840

GCGAATGCCT TCGTATTTGA TTGCTCTTGT GATTTCCGAA TTTAAGTACA TTGAAAATTA      900
```

```
TACGAAAAGC GGTGTTCGAT TCCGAATATG GGCTCGTCCG GAAGCTATGA AGATGACAGA    960

ATATGCCATG GTAGCTGGAA TCAAATGCTT GGATTACTAT GAGGACTTCT TCGGGATCAA   1020

ATTCCCTCTT CCAAAACAAG ATATGGTTGC TCTTCCTGAC TTCTCATCTG GTGCTATGGA   1080

GAACTGGGGT CTCATCACAT ACAGGGAGGG TTCCGTACTA TACGATGAAA ACCTCTATGG   1140

ACCAATGAAT AAGGAGCGGG TTGCAGAAGT GATTGCACAC GAGCTTGCAC ATCAGTGGTT   1200

CGGTAATTTG GTCACGATGA AGTGGTGGGA TAACCTATGG CTAAACGAAG GATTCGCGTC   1260

ATTCGTAGAA TACATTGGAG CCGACTTCAT CAGCGATGGT C                      1301
```

(2) INFORMATION FOR SEQ ID NO:10:

(i) SEQUENCE CHARACTERISTICS:
        (A) LENGTH: 1280 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

```
GGTTTAATTA CCCAAGTTTG AGATGACGGC GGAGTGGCAG AAGCGTCGAA TCTTGGGCTT     60

CTCACCTATC AGCCTACTTT GTACATTATT TGTATTAGCT GCTGCCGTTG GACTCTCCAT    120

TGGTCTTACC TATTACTTCA CTCGTAAAGC ATTCGATACC ACACAAAAAG AACAGAAGGA    180

TGACAGTGGT GGTAAAGAAA AGGATAATTC TCCTTCTGCA GAAGAACTAC TTCTTCCAAC    240

GAACATAAAA CCAGTCTCGT ACGACTTGAA CATCAAAACA TATCTACCGG GTTACGTGAA    300

CTTTCCACCA GAAAAGAATC TCACATTTGA TGCCCATGTG GAGATTGCTA TGGTTGTGGT    360

TGAGCCTACA AATAGTATTG TGCTGAACTC GAAGAAAATC ACTTTGGCAC AAGGAGGATG    420

CGAACTGTTC TCAGGTAATC AGAAACTTGA CATCGAAAGT GTAAAGATGC AGGAAAGACT    480

TGACAAGCTT GAGATTACCC TCAAAAATCA GCTGCAAAAA GATCTGAAAA TCCTGCTCAA    540

GATCACTTAC ACCGGCCTTA TTAGCGACAC TCTCGGTGGG CTCTACCAGT CCATCTACAC    600

TGATAAGGAC GGAAAAACTA AGATCGTTGC TGTTTCACAA AATGAACCAT CAGACGCTCG    660

TCGTATAGCG CCATGCTTTG ACGAACCGAA GTACAAGGCA ACATGGACTG TCACCGTCGT    720

TCATCCCAAA GGTACAAAGG CTGCATCGAA CGGCATTGAA GCAAATGGAA AAGGGGAGCT    780

CAAGGGTGAT TGGATAACGT CTAAATTTAA AACTACCCCA CCGATGTCGT CCTATTTATT    840

GGCTATTATT GTTTGTGAAT TGAATACAT  TGAAGGATTT ACAAAAACAG GTGTACGGTT    900

CCGTATATGG TCTCGACCAG AGGCGATGGC AATGACGGGA TATGCCCTGG ATGCTGGCAT    960

CAGATGTCTG GAGTTCTATG AGAGATTCTT TGACATCAAA TTCCCTCTGG AAAAACAAGA   1020

TATGATTGCT CTACCTGATT TCACCGCTGG TGCTATGGAA AACTGGGGTC TTATCACTTA   1080

CAGAGAGGAT TCTCTTCTAT ACGATGAGAA AATTTATGCG CCGATGAATA AGCAGCGGGT   1140

TGCTCTCGTA GTTGCACACG AGCTTGCTCA TCAGTGGTTC GGCAATCTGG TCACATTGAA   1200

GTGGTGGGAT GATACGTGGT TGAACGAAGG TTTTGCGACA TTTGTTGAAT ATCTTGGAAT   1260

GGACGAAATT AGCCACAACA                                              1280
```

(2) INFORMATION FOR SEQ ID NO:11:

(i) SEQUENCE CHARACTERISTICS:
    (A) LENGTH: 1293 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

```
GGTTTAATTA CCCAAGTTTG AGGGTCTCCA TCTAGATGAC GTCGCAGGGG AGAACGCGGA      60

CATTGCTGAA TCTAACTCCA ATCCGTCTTA TTGTCGCATT ATTTCTAGTA GCTGCTGCAG     120

TCGGCCTCTC TATTGGTCTC ACCTATTACT TTACTCGCAA AGCGTTCGAT ACCTCAGAAA     180

AGCCAGGGAA GGATGATACT GGTGGCAAGG ACAAAGACAA TTCTCCCTCT GCGGCGGAAC     240

TACTCCTTCC AAGTAATATA AAACCATTGT CTTACGACTT GACGATCAAA ACATATCTAC     300

CTGGTTATGT GGACTTCCCA CCGGAGAAAA ACCTCACATT CGATGGGCGT GTGGAAATAT     360

CAATGGTTGT AATTGAGCCA ACAAAGAGTA TCGTACTCAA TTCAAAGAAG ATCTCTGTAA     420

TACCCCAAGA ATGTGAACTG GTATCGGGCG ATAAAAAACT CGAAATTGAA AGTGTAAAGG     480

AGCACCCAAG ACTGGAAAAG GTTGAGTTTC TTATCAAAAG CCAACTGGAA AAAGATCAAC     540

AAATCTTGCT CAAGGTCGGC TACATCGGTC TCATCAGCAA CAGCCTTGGT GGAATCTACC     600

AGACCACTTA TACCACCCCG GATGGCACCC CTAAGATCGC TGCAGTTTCA CAAAATGAGC     660

CCATAGATGC TCGTCGAATG GTACCATGCA TGGATGAACC GAAATACAAA GCAAACTGGA     720

CCGTTACTGT CATTCATCCA AAAGGCACCA AGCCGTCTC GAATGGAATC GAAGTGAACG     780

GAGATGGAGA GATCAGTGGT GATTGGATCA CATCGAAGTT CTTGACTACT CCACGGATGT     840

CATCCTACTT GTTGGCAGTT ATGGTTTCAG AATTTGAATA CATCGAAGGT GAAACAAAGA     900

CGGGTGTTCG GTTCCGTATA TGGTCACGCC CAGAGGCAAA GAAGATGACA CAATATGCTC     960

TGCAATCTGG TATCAAGTGC ATAGAATTCT ACGAAGATTT CTTTGATATC AGATTCCCTC    1020

TGAAGAAACA AGATATGATT GCCCTTCCTG ATTTCTCTGC CGGTGCCATG GAGAATTGGG    1080

GCCTCATCAC TTACAGGGAA AACTCTTTGT TGTACGATGA CAGATTCTAT GCACCGATGA    1140

ATAAACAGCG AATTGCTCGC ATTGTTGCTC ATGAGCTTGC TCATCAGTGG TTCGGCGACT    1200

TGGTTACGAT GAAGTGGTGG GATAAATTTGT GGTTGAATGA AGGTTTTGCA AGATTCACAG    1260

AATTCACTGG AGCTGGTCAG ATAACTCAAG ATG                                 1293
```

(2) INFORMATION FOR SEQ ID NO:12:

(i) SEQUENCE CHARACTERISTICS:
        (A) LENGTH: 746 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

```
CTTGAAGAAA TGAAAAGCT TTTTGACAAG GAGGTCATGA AATGTCAACC TGGTCAGCAA      60

GCGACCGACT GCGCGAAGGT AACTGCTCCT CTCCGAAAAA CTGTTTACTG CTATGGGGTC    120
```

| CAGGAAGGCG GTGATGAGGC ATTCGACAAG GTGATGGAAC TATATAATGC GGAACAAGTC | 180 |
| CAGTTGGAGA AAGACAGTCT ACGTGAAGCA TTGGGATGTC ATAAAGACGT TACTGCTCTA | 240 |
| AAGGGACTTC TTATGCTGGC GTTGGATCGG AATTCGTCAT TTGTGCGTCT TCAAGATGCT | 300 |
| CATGATGTGT TTAACATTGT ATCCAGAAAT CCTGTTGGAA ACGAACTGCT GTTCAATTTC | 360 |
| CTCACAGAGC GATGGGAAGA GATACTTGAA AGTTTGTCAA TACGACACAG ATCAGTTGAT | 420 |
| CGAGTGATCA AAGCCTGTAC TCGAGGACTA CGATCCAGGG AACAAGTACA ACAGTTGAAG | 480 |
| AATCTATACA AAAATGACAA GCGTGCTCGC GAATACGGTG CATTTGGTGG GGCAATAGAA | 540 |
| AGATCGGAAC ACAGAGTCAA ATGGATTGAG AAACATTTCC GAAAACTAGC AGCTTTCTTC | 600 |
| AAAAAATCTA ATTCATAATT CTGAAATGGC TATAACTAGC ACACTGGATA GTTGTCTCGA | 660 |
| ATCATCCAAA AAGATTAATG ATGTTTTTTT ACTAGATAAT ATGGAGATAT TCTGTAAATT | 720 |
| TGTCATCGAT TCAAGTGTCT GTATTG | 746 |

(2) INFORMATION FOR SEQ ID NO:13:

(i) SEQUENCE CHARACTERISTICS:
        (A) LENGTH: 1274 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:13:

| TCTTGAAGAA ATGAAAAAGC TTTTCGACGA AGAGGTCATG AAAAAATGTA GACCTGGTCA | 60 |
| GCAAGCGACC GACTGCGTAA AGGTAACTGC TCCTCTCCGA AAAACTGTTT ACTGCTATGG | 120 |
| GGTCCAGGAA GGCGGTGATG AGGCATTCGA CAAGGTGATG AACTATATA ATGCGGAACA | 180 |
| AGTCCAATTG GAGAAAGACA GTCTACGTGA AGCATTGGGA TGTCATAAAG ACGTTACTGC | 240 |
| TCTAAAGGGA CTTCTTATGC TGGCTTTGGA TCGGAATTCG TCATTTGTGC GTCTTCAAGA | 300 |
| TGCTCATGAT GTGTTTAACA TTGTATCCAG AAATCCTGTT GGAAACGAAC TGCTGTTCAA | 360 |
| TTTCCTCACA GAGCGATGGG AAGAGATACT TGAAAGTTTG TCAATACGAC ACAGATCAGT | 420 |
| TGATCGAGTG ATCAAAGCCT GTACTCGAGG ACTACGATCC AGGGAACAAG TACAACAGTT | 480 |
| GAAGAATCTA TACAAAAATG ACAAGCGTGC TCGCGAATAC GGTGCATTTG GTGGGCAAT | 540 |
| AGAAAGATCG GAACACAGAG TCAAATGGAT TGAGAAACAT TTCCGAAAAC TAGCAGCTTT | 600 |
| CTTCAAAAAA TCTAATTCAT AATTCTGAAA TGGCTATAAC TAGCACACTG GATAGTTGTC | 660 |
| TCGAATCATC CAAAAAGATT AATGATGTTT TTTTACTAGA TAATATGGAG ATATTCTGTA | 720 |
| AATTTGTCAT CGATTCAAGT GTCTGTATTG CAGCCACATT ACATATCTCG ATGGTTCTGT | 780 |
| GAATTTTTGA TGGAATTATT TTCTCCTCAA AATAGACACT ATGCGCTAAC TCCCATTATT | 840 |
| ACCAATCTTT GAGAGAAATC TTTTGCAATA TACCCTAAAT AGCCCTTGGG AACTAGCTTT | 900 |
| TTTCATTATT GTAATTTTTG TACTCTTCAA ATGACGTATT CCAACATGA CACATTCTCA | 960 |
| GTGATTTACT CGAGTAATTT TATTCTTCTC AATTGCAGTG CCTTATTGTT ATTCGCTTTG | 1020 |
| AGACTTTGTA GCTCAACTGT TTTCTGCCCT GCTGTCTTCT TCTCTTTATC TACTACTTCA | 1080 |
| GTGATGAACT TACCTGAAGT TGTAGGTTTT AAGAAAGAAA TAACTATTTT CCATAACTCA | 1140 |
| TCTTCATGCC ATTGTTCTTT GGACTTTCTC ATGCTTCACA TTGTAGAGAT ATTTACTAAA | 1200 |

-continued

| AATGGAATTC TAATTTTCGT TTACTTACAT AAAAATCACT TATTGCCTAA AAAAAAAAAA | 1260 |
| AAAAAAAAAA AAAA | 1274 |

(2) INFORMATION FOR SEQ ID NO:14:

(i) SEQUENCE CHARACTERISTICS:
        (A) LENGTH: 3296 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (xi) SEQUENCE DESCRIPTION: SEQ ID NO:14:

| GCTGAATCTA ACTCCAATCC GTCTAATTTT TGCATTATTT CTAGTAGCTG CTGCAGTCGG | 60 |
| CCTCTCTATT GGTCTCACCT ATTACTTTAC TCGCAAAGCG TTCGATACCT CAGAAAAGCC | 120 |
| AGGGAAGGAT GATACTGGTG GCAAGGGCAA AGACAATTCT CCCTCTGCGG CGGAACTACT | 180 |
| TCTTCCAACC AATATAAAAC CATTGTCTTA CGATTTGACG ATCAAAACAT ATCTACCTGG | 240 |
| TTATGTGAAC TTCCCACCGG AGAAGAATCT CACATTCGAT GGGCGTGTGG AAATATCAAT | 300 |
| GGTTGTAATT GAGCCAACAA AGAGTATCGT GCTCAATTCA AAGAAGATCT CTGTGATACC | 360 |
| CCAAGAATGT GAACTGGTAT CGGGCGATAA AAAACACGAA ATTGAAAGTG TAAAGGAGCA | 420 |
| CCCAAGACTG GAAAAGGTCG AGTTTCTTCT TAAGAACCAA CTGGAAAAAG ATCAACAAAT | 480 |
| CTTGCTCAAG GTCGGCTATA TCGGCCTCAT CAGCAACAGT CTTGGAGGAA TCTACCAGAC | 540 |
| CACTTACACC ACCCCGAATG GCACCCCTAA GATCGCTGCA GTTTCACAAA ATGAGCCCAT | 600 |
| AGATGCTCGT CGAATGGTAC CATGCATGGA CGAACCGAAA TACAAAGCAA ACTGGACCGT | 660 |
| TACTGTCATT CATCCAAAAG GCACCAAAGC CGTCTCGAAT GGAATCGAAG TGAACGGAGA | 720 |
| TGGAGAGATC AGTGGTGATT GGATCACATC GAAGTTCTTG ACTACTCCAC GGATGTCATC | 780 |
| CTACTTGTTG GCAGTTATGG TTTCAGAATT TGAATACATT GAAGGTGAAA CAAGGACGGG | 840 |
| TGTCCGGTTC CGCATATGGT CACGCCCAGA GGCCAAGAAG ATGACAAAAC TTGCTTTGGA | 900 |
| TTATGGTATC AAATGCATAG AGTTCTACGA AGATTTCTTT GATATCAAAT TCCCTCTGAA | 960 |
| AAAACAAGAT ATGATCGCCC TTCCTGATTT CTCAGCAGGA GCCATGGAGA ACTGGGGTCT | 1020 |
| TATCACTTAC AGGGAAAACT CTTTGTTGTA CGATGACAGA TTCTATGCAC CGATGAATAA | 1080 |
| ACAGCGAATT GCTCGCATTG TTGCTCATGA GCTTGCCCAT CAGTGGTTTG GGACTTGGT | 1140 |
| TACAATGAAG TGGTGGGATA ATCTGTGGTT GAATGAAGGT TTTGCAAGAT TCACGGAATT | 1200 |
| CATTGGAGCT GGTCAGATAA CTAAAGATGA CGCCAGAATG AGGAACTACT TTCTGATTGA | 1260 |
| TGTACTTGAA CGCGCTTTGA AAGCTGATTC GGTAGCGTCA AGCCATCCAC TTTCCTTCAG | 1320 |
| AATCGACAAA GCTGCAGAAG TTGAAGAAGC CTTTGATGAT ATCACATACG CCAAAGGAGC | 1380 |
| TTCTGTTCTT ACTATGTTGA GAGCCTTGAT TGGAGAAGAA AAACATAAGC ATGCAGTATC | 1440 |
| GCAGTACCTC AAGAAGTTCT CGTATAGCAA TGCAGAAGCG ACTGATCTAT GGGCAGTTTT | 1500 |
| CGATGAAGTT GTCACTGACG TCGAAGGTCC AGACGGCAAA CCTATGAAAA CCACGGAATT | 1560 |
| TGCAAGTCAG TGGACGACTC AGATGGGCTT CCCAGTTATT TCCGTAGCAG AGTTTAACTC | 1620 |
| GACTACTTTG AAATTAACGC AAAGTCGATA TAAGGCGAAT AAAGACGCTG TGGAGAAAGA | 1680 |

```
GAAGTACCGT CATCCGAAAT ACGGATTTAA ATGGGATATT CCATTGTGGT ATCAGGAAGG        1740

CGATAAGAAG GAGATAAAGC GAACATGGCT GAGAAGAGAT GAACCGCTTT ACTTGCATGT        1800

TAGTAATCCT GGTGCTCCAT TTGTGGTGAA CGCAGACCGC TATGGATTTT ATCGACAAAA        1860

TCATGACGCT AATGGTTGGA AAAAGATAAT CAAGCAGCTC AAGGACAATC ATGAGGTTTA        1920

TAGTCCTCGG ACAAGGAATG TCATCATTAG CGATGCGTTT GCTGCAGCCG CAACTGACGC        1980

AATTGAGTAT GAGACTGTTT TTGAACTTCT GAAATATGCC GAAAAGAAA CGGAATACCT         2040

ACCGTTGGAA ATAGCAATGT CCGGGATCTC TTCGATTTTG AAGTACTTCG GTACCGAGCC        2100

GGAAGCAAAG CCAGCTCAAG TGTACATGAT GAACATATTG AAGCCGATGT ATGAAAAAAG       2160

CAGTATCGAG TTCATTACCA ATAACTACAG AAACGACACG CTGTTTTTCC AAATCAACCT       2220

CCAAAAGGAT GTCGTTGATA TGTTCTGCGC CCTTGGATCG CAAGACTGCA GGCAGAAATA      2280

TAAAAAACTT TTCGATGACG AAGTCATGGC GAAATGCAGG GATGGTCAAG CAGCAACCGA      2340

ATGCGTGAGA ATCGCCGCTC CTCTCCGATC AAGTGTTTAT TGTTATGGTG TGAAGGAAGG       2400

CGGTGATTAT GCTTTCGACA AGGTGATGGA GCTTTATACG GCCGAAACAC TTGCCCTAGA      2460

AAAAGACTTC CTACGCCTAG CATTAGGATG TCACAAAGAT GTTACTGCTT TGAAAGGACT      2520

TCTCTTGCGG GCTCTGGACA GGAATTCGTC ATTCGTACGT ATGCAGGATA TCCCAAGTGC      2580

TTTCAACGAT GTAGCAGCAA ATCCTATTGG CGAAGAATTC ATTTTCAATT TCCTCATTGA      2640

GAGATGGCCA GATATCATTG AAAGTATAGG AACGAAGCAC ACATATGTTG AGAAAGTGAT      2700

ACCAGCCTGC ACTTCAGGAA TCCGCTCACA ACAGCAGATT GACCAGCTGA AGAATCTGCA     2760

GAAAAATGGC ATAAATGCTC GTCAATTTGG TGCATTCGAT AAAGCAATCG AACGAGCACA      2820

AAATAGGGTG GATTGGATTA AAAAACATTT CCAAAAATTA GCGGCTTTCT TCAAGAAAGC     2880

CACCTTGTAG TTTGAATTAC GTCGCCATTA ATCCAGATCT TAAAGCTCGC TAAGGAATAT      2940

GTGGGAACTG ACTGTGTGTT GGTTACTGTT CCACTGAATG GAAGTTTTTA CCCACAAAAA      3000

TTTTTACCAT TTGCCTTCCA TGAGGGGTCA TTGTTGTCAC TTGAATAGTA AACAAAGCTC      3060

AGTATTAGGA CCCAGTGATC AATATTACTT TTGCTTCATC AAATTGTTAC CTTCTCTATA     3120

CCCTCTTCCT ACCTGAATTC AGAAATTTGT TCATATTCGT TTGTAGTCTG TTGCTCAGAA    3180

CACTTTCTCC TCGATAGCTT TTTGTTTGTT TTTCTTTTGA TTGTATTGAT CGTTTTACAA    3240

TTGTATAGAT TAGTTATCTG ATAAATATTG ATGGCTAAAA AAAAAAAAAA AAAAAA        3296
```

(2) INFORMATION FOR SEQ ID NO:15:

(i) SEQUENCE CHARACTERISTICS:
        (A) LENGTH: 3319 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

```
GCTGAATCTA ACTCCAATCC GTCTAATTTT TGCATTATTT CTAGTAGCCG CTGCAGTCGG        60

CCTCTCTATT GGTCTCACCT ATTACTTTAC TCGCAAAGCG TTCGATACCT CAGAAAAGCC       120

AGGGAAAGAT GATACTGGTG GTAAAGACAA AGATAATTCT CCCTCTGCGG CGGAACTACT      180

TCTTCCAACC AACATAAAAC CATTGTCTTA CGATTTGACA ATCAAAACAT ATCTACCTGG      240
```

-continued

```
TTATGTGAAC TTCCCACCGG AGAAGAATCT CACATTTGAT GGGCGTGTCG AAATTTCAAC      300

GGTTGTCATT GAGCCAACAA AGAGTATCGT GCTCAATTCA AAGAAGATCT CAGTAATACC      360

CCCTGAATGT GAACTGGTAT CGGGCGGTAA AAAACTCGAA ATCGAAAATG TAAAGGATCA      420

CCCAAGACTG GAAAAGGTTG AGTTTCTTCT TAAGAACCAA CTGGAAAAAG ATCAACAAAT      480

CTTGCTCAAG GTTGCCTACA TCGGCCTCAT CAGCAACAGC CTTGGCGGAA TCTACCAGAC      540

CACTTACACA ACCCCGGATG GCACCCCCAA GATCGCTACA GTGTCACAAA TGAGCCCAT       600

AGATGCTCGT CGGATGGTGC CATGCATGGA TGAACCGAAA TACAAAGCGA ATTGGACCGT      660

TACTGTCATT CATCCAAAAG GTACAAAAGC CGTCTCGAAT GGCATCGAAA CGAACGGAGA      720

TGGAGAGATC AGTGGTGATT GGATTACGTC GAAGTTCTTG ACTACTCCGA GGATGTCATC      780

CTACTTGTTG GCAGTTATGG TATCAGAATT TGAATTTATC GAGGGTAAAA CAAAGACAGA      840

TGTTCGGTTC CGTATATGGT CACGCCCAGA GGCCAAGAAG ATGACAAAAC TTGCTTTGGA      900

TTATGGTATC AAATGCATAG AGTTCTACGA AGATTTCTTT GATATCAGAT TCCCCTTAAA      960

GAAACAAGAT ATGATCGCCC TTCCTGATTT CTCAGCAGGA GCCATGGAGA ACTGGGGTCT     1020

TATCACTTAC AGGGAAAACC CTTTGTTGTA CGATGACAGA TTCTATGCAC CGATGAATAA     1080

ACAGCGAATT GCTCGCATTG TTGCTCATGA GCTTGCCCAT CAGTGGTTTG GCGACTTGGT     1140

TACGATGAAG TGGTGGGATA ATCTGTGGTT GAATGAAGGT TTTGCAAGAT TCACAGAATT     1200

CATTGGAGCT GGTAAGATAA CTGAAGATGA CGCCAGAATG AGGAACTACT TCCTGATTGA     1260

TGTACTTGAA CGCGCGTTGA AAGCTGATTC CGTAGCGTCA AGCCATCCAC TTTCCTTCAG     1320

AATCGACAAA GCTGCAGAAG TTGAAGAAGC GTTTGATGAT ATCACATACG CCAAAGGAGC     1380

TTCTGTTCTT ACGATGCTGA GAGCGTTGAT CGGAGAAGAA AAACATAAGC ATGCGGTATC     1440

GCAGTATCTC AAGAAGTTCT CGTATAGCAA TGCAGAAGCG ACTGATCTAT GGGCAGTTTT     1500

CGATGAAGTT GTCACTGATG TCGAGGGTCC AGACGGCAAA CCTATGAAAA CCACGGAATT     1560

CGCAAGTCAG TGGACAACTC AGATGGGCTT TCCAGTAATT TCTGTGGCAG AGTTTAACTC     1620

GACTACTCTG AAACTAACGC AAAGTCGATA TAAGGCGAAT AAGGACGCTG TTGAGAAAGA     1680

GAAATACCGT CATCCGAAAT ACGGATTCAA GTGGGATATT CCATTGTGGT ATCAGGAAGG     1740

CGATAAGAAG GAGGTAAAGC GAGCATGGTT AAGAAGAGGT GAACCGCTTT ACTTGCATGT     1800

GAGTGATCCT GGCGCTCCAT TTGTGGTGAA TGCGGACCGC TATGGATTTT ACCGACAAAA     1860

CCACGACACT AATGGTTGGA AAAGATAAT CAAGCAGCTC AAGGATAATC ATGAGGTTTA      1920

CAGTCCCCGG ACAAGGAATG CCATCATTAG CGATGCGTTT GCTGCGGCTG CAACTGACGC     1980

GATTGAGTAC GAGACTGTAT TCGAACTTCT GAAATATGCC GAAAAGAAA CGGAATACCT      2040

ACCGTTGGAA ATAGCAATGT CTGGAATCTC TTCGATTTTG AAGTACTTCG GTACCGAGCC     2100

CGAGGCAAAG CCAGCTCAAA CATACATGAT GAACATATTG AAGCCGATGT ATGAGAAAG     2160

CGATATCGAC TTCATTGCCA AAAACTACAA GGACGACAAG CTGTTTTTCC AAATCAACCT     2220

CCAAAAAGAT GTCATTGATA TGTTCTGCGC CCTTGGATCG CAAGACTGCA GGAAGAAATA     2280

TAAAAAACTT TTCGATGACA AAGTCATGGC GAAATGCAGG GATGGCCAAG CAGCAACCGA     2340

ATGCGTGAAA ATCGCCGCTC CTCTCCGATC AAGTGTTTAT TGTTATGGTG TGAAGGAAGG     2400

CGGTGATTAT GCTTTCGACA AGGTGATGGA GCTTTATACG GCCGAAACAC TCGCCCTAGA     2460

AAAAGACTTC CTACGCCTAG CATTAGGATG TCACAAAGAT GTTACCGCTT TGAAAGGACT     2520

TCTCCTGCGG GCTCTGGACA GGAATTCGTC GTTCGTACGA ATGCAGGATA TCCCAAGTGC     2580

TTTCAACGAT GTAGCAGCAA ATCCTATTGG CGAAGAATTC ATTTTCAATT TCCTTATTGA     2640
```

```
GAGATGGCCA GATATCGTTG AAAGTATAGG AACGAAACAC ACATATGTTG AAAAAGTGAT    2700

ACCAGCTTGC ACTTCAGGAA TCCGCTCACA CAACAGATT GACCAGCTGA AGAATCTGCA    2760

GAAAAATGGC ATAAACGCTC GTCAATTTGG TGCATTCGAT AAAGCGATCG AACGAGCACA    2820

AAATAGGGTG GATTGGATTA AAAAACATTT CCAAAAATTA GCGGCTTTCT TCAAGAAAGC    2880

CACCTTGTAA TTCGTATTAC ATCACCATGA ATCCAGATCT TAAAACTCAC TAAGGAATGT    2940

GTGGGAACTG ACTGTCTGTT GCTTACTGTT CCACTGAATG GAAGTTTTTA CCCATAAAAA    3000

TTTTTACCAT TTGCCTTCCG TGAGGGGTCA TTGTTGTCAC TTGAATAGTA AACAAAGCTC    3060

AGTATTGGAC CCAGTGATCA ATATTACTTT CGCTTCATCG AATTGTTACC TTCTCTATAC    3120

CCTCGTCCTA CCTGAATTCA CACATTTGTT CATATTTGTT TGTAGTCTGT TGCTCAGAAC    3180

ACTTTCTCTT CGATAGCTTT TTGTTTGTTT TTCTTTTGAT TGTATTGATC GTTTTACAAT    3240

TGTATAGATT AGTTATCTGA TAAATATTGA TGGCTAAGGA AAAAAAAAAA AAAAAAAAA    3300

AAAAAAAAAA AAAAAAAA                                                  3319

(2) INFORMATION FOR SEQ ID NO:16:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:16:

Asp Asn Ser Pro Ser Ala Glu Glu Leu Leu Leu Pro Thr Asn Ile Lys
1               5                   10                  15

Pro Val Ser Tyr Asp Leu Lys Ile Ala Thr Tyr Leu Pro Gly
            20                  25                  30

(2) INFORMATION FOR SEQ ID NO:17:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (xi) SEQUENCE DESCRIPTION: SEQ ID NO:17:

Leu Tyr Leu Ala Glu Asp Val Gln Leu Xaa Lys Gly Ile Leu Phe
1               5                   10                  15

(2) INFORMATION FOR SEQ ID NO:18:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant
```

(ii) MOLECULE TYPE: peptide (iii) HYPOTHETICAL: NO (iv) ANTI-SENSE: NO (xi) SEQUENCE DESCRIPTION: SEQ ID NO:18:

```
Leu Ala Tyr Asp Glu Lys Ser Tyr Ala Pro Asp Asn Lys Gln Tyr
1               5                  10                  15
```

(2) INFORMATION FOR SEQ ID NO:19:

(i) SEQUENCE CHARACTERISTICS:
        (A) LENGTH: 3084 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

```
GGTTTAATTA CCCAAGTTTG AGATGACAGC AGAGGAGAGT CAGGAGCAGG AGACGCAGCA      60
ACCACGAAAA AATACAGTGC TACGGCTCAC CCCAATCAAG TCTCTCTTTG CTTTGTTAGT     120
GGTAGCTGCT GCCGTCGGCC TCTCAATCGG TCTCACCTAT TACTTTACAA GGAAAGCTTT     180
TGATACTACT GGCGGAAATG GAAAAGGGGA TCAACCTATT GTCGATGATA ATTCCCCATC     240
AGCTGAAGAA TTACGTCTCC CAACAACCAT AAAACCTTTG ACATACGACT TAGTAATCAA     300
AACGTATCTG CCAAACTATG TAAACTATCC ACCTGAGAAA GATTTCGCTA TTGATGGGAC     360
TGTGGTGATT GCTATGGAAG TTGTGGAGCC AACAAAGTCT ATTGTGCTCA ACTCGAAAAA     420
TATTCCTGTA ATTGCAGACC AGTGCGAACT GTTTTCTAAC AACCAAAAAC TCGACATCGA     480
AAAGGTTGTG GATCAGCCAA GGCTGGAGAA AGTCGAATTC GTTTTGAAGA AAAAGCTGGA     540
GAAGAATCAG AAAATCACGC TCAAGATTGT ATACATTGGC CTTATCAACG ACATGCTTGG     600
AGGACTTTAT CGAACAACCT ACACGGATAA AGATGGTACA ACCAAGATTG CTGCATGCAC     660
TCATATGGAA CCGACGGACG CCCGTCTTAT GGTCCCCTGT TTCGACGAGC CGACGTTTAA     720
GGCAAACTGG ACTGTGACTG TGATTCATCC GAAGGGCACC AGTGCCGTGT CGAATGGAAT     780
AGAAAAGGGA GAAGGAGAAG TCTCTGGCGA TTGGGTCACA ACCAGATTCG ATCCAACCCC     840
GCGAATGCCT TCGTATTTGA TTGCTCTTGT GATTTCCGAA TTTAAGTACA TTGAAAATTA     900
TACGAAAAGC GGTGTTCGAT TCCGAATTCC GGCTCGTCCG GAAGCTATGA AGATGACAGA     960
ATATGCCATG ATAGCTGGAA TCAAATGTTT GGATTACTAT GAGGACTTCT TCGGGATCAA    1020
ATTCCCACTT CCAAAACAAG ATATGGTTGC TCTTCCTGAC TTCTCATCTG GTGCTATGGA    1080
GAACTGGGGT CTCATCACAT ACAGGGAGGG TTCCGTGCTC TACGATGAAA ACCTCTACGG    1140
ACCAATGAAT AAGGAGCGGG TTGCAGAAGT GATCGCGCAC GAACTTGCAC ATCAGTGGTT    1200
CGGTAATTTG GTCACGATGA AGTGGTGGGA TAACCTATGG CTGAACGAAG GATTCGCGTC    1260
ATTCGTGGAA TACATCGGAG CCGACTTCAT CAGCGATGGT CTATGGGAAA TGAAAGATTT    1320
CTTCCTGCTG GCACCGTACA CAAGTGGTAT TACGGCTGAT GCAGTAGCTT CAAGCCATCC    1380
GCTTTCCTTC AGAATAGATA AGGCTGCAGA TGTATCAGAA GCGTTCGATG ATATCACATA    1440
CCGTAAAGGA GCATCCGTTC TTCAAATGCT ATTGAATTTA GTTGGGGACG AAAATTTCAA    1500
GCAGTCTGTT TCGCGTTACC TCAAGAAGTT TTCATATGAT AATGCGGCTG CTGAAGATTT    1560
```

```
ATGGGCAGCA TTCGACGAAA CCGTCCAAGG TATAACCGGA CCTAATGGTG GACCATTGAA   1620

AATGTCCGAG TTTGCGCCAC AATGGACAAC TCAGATGGGG TTCCCTGTTC TTACTGTCGA   1680

GTCGGTTAAC GCAACGACTT TGAAAGTCAC CCAAAAACGA TACAGGCAGA ACAAGGATGC   1740

AAAGGAACCA GAGAAGTACC GTCATCCAAC TTATGGGTTC AAATGGGATG TTCCTCTGTG   1800

GTATCAGGAA GATGAACAGC AAGTGAAAAG AACTTGGTTA AAAAGAGAGG AACCGCTCTA   1860

TTTCCATGTA AGCAATTCTG ATTCGTCAGT TGTGGTGAAT GCCGAACGTC GTGCTTTTTG   1920

CCGATCAAAC TATGACGCTA ACGGTTGGAG GAACATTATG AGAAGACTCA AGCAGAATCA   1980

TAAGGTCTAT GGTCCACGAA CAAGAAACGC TCTCATAAGT GATGCGTTTG CAGCAGCTGC   2040

AGTTGAGGAA ATGAATTACG AGACCGTATT TGAAATGCTC AAATACACCG TGAAAGAAGA   2100

GGATTACTTA CCATGGAAGG AGGCAATATC AGGATTCAAT ACAATTTTGG ACTTTTTCGG   2160

CAGCGAACCC GAATCTCAAT GGGCTTCGGA ATACATGCGA AAACTGATGA AGCCAATTTA   2220

TGACAAGAGT AGCATCAAGT TTATAGCGGA GAACTACAAA AAAGATTCGC TTTTCTTCAA   2280

AAATAATCTC CAAATAGCTG TTATTGACAC ATACTGTGGT CTTGGAGGCA AGAATGTCT   2340

TGAAGAAATG AAAAAGCTTT TTGACAAGGA GGTCATGAAA TGTCAACCTG GTCAGCAAGC   2400

GACCGACTGC GTAAAGGTAA CTGCTCCTCT CCGAAAAACT GTTTACTGCT ATGGGGTCCA   2460

GGAAGGCGGT GATGAGGCAT TCGACAAGGT GATGGAACTA TATAATGCGG AACAAGTGCA   2520

GTTGGAGAAA GACAGTCTAC GTGAAGCATT GGGATGCCAT AAAGACGTTA CAGCTCTAAA   2580

GGGACTTCTT ATGCTGGCTT TGGATCGGAA TTCGTCATTT GTGCGTCTTC AAGATGCTCA   2640

TGATGTGTTT AACATTGTAT CCAGAAATCC TGTTGGAAAC GAACTGCTGT TCAATTTCCT   2700

CACAGAGCGA TGGGAAGAGA TACTTGAAAG TTTGTCAATA CGACACAGAT CAGTTGATCG   2760

AGTGATCAAA GCCTGTACTC GAGGACTACG ATCCAGGGAA CAAGTACAAC AGTTGAAGAA   2820

TCTATACAAA AATGACAAGC GTGCTCGCGA ATACGGTGCA TTTGGTGGGG CAATAGAAAG   2880

ATCGGAACAC AGAGTCAAAT GGATTGAGAA ACATTTCCGA AAACTAGCAG CTTTCTTCAA   2940

AAAATCTAAT TCATAATTCT GAAATGGCTA TAACTAGCAC ACTGGATAGT TGTCTCGAAT   3000

CATCCAAAAA GATTAATGAT GTTTTTTTAC TAGATAATAT GGAGATATTC TGTAAATTTG   3060

TCATCGATTC AAGTGTCTGT ATTG                                          3084
```

(2) INFORMATION FOR SEQ ID NO:20:

(i) SEQUENCE CHARACTERISTICS:
        (A) LENGTH: 3358 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

```
GGTTTAATTA CCCAAGTTTG AGATGACGGC GGAGTGGCAG AAGCGTCGAA TCTTGGGCTT     60

CTCACCTATC AGCCTACTTT GTACATTATT TGTATTAGCT GCTGCCGTTG GACTCTCCAT    120

TGGTCTTACC TATTACTTCA CTCGTAAAGC ATTCGATACC ACACAAAAAG AACAGAAGGA    180

TGACAGTGGT GGTAAAGAAA AGGATAATTC TCCTTCTGCA GAAGAACTAC TTCTTCCAAC    240

GAACATAAAA CCAGTCTCGT ACGACTTGAA CATCAAAACA TATCTACCGG GTTACGTGAA    300
```

```
CTTTCCACCA GAAAAGAATC TCACATTTGA TGCCCATGTG GAGATTGCTA TGGTTGTGGT      360

TGAGCCTACA AATAGTATTG TGCTGAACTC GAAGAAAATC ACTTTGGCAC AAGGAGGATG      420

CGAACTGTTC TCAGGTAATC AGAAACTTGA CATCGAAAGT GTAAAGATGC AGGAAAGACT      480

TGACAAGCTT GAGATTACCC TCAAAAATCA GCTGCAAAAA GATCTGAAAA TCCTGCTCAA      540

GATCACTTAC ACCGGCCTTA TTAGCGACAC TCTCGGTGGG CTCTACCAGT CCATCTACAC      600

TGATAAGGAC GGAAAAACTA AGATCGTTGC TGTTTCACAA AATGAACCAT CAGACGCTCG      660

TCGTATAGCG CCATGCTTTG ACGAACCGAA GTACAAGGCA ACATGGACTG TCACCGTCGT      720

TCATCCCAAA GGTACAAAGG CTGCATCGAA CGGCATTGAA GCAAATGGAA AAGGGGAGCT      780

CAAGGGTGAT TGGATAACGT CTAAATTTAA AACTACCCCA CCGATGTCGT CCTATTTATT      840

GGCTATTATT GTTTGTGAAT TTGAATACAT TGAAGGATTT ACAAAAACGG GTGTTCGGTT      900

CCGTATATGG TCTCGACCAG AGGCGAAACG AATGACGGCA TACGCTTTGG ATGCTGGCAT      960

CAGATGCCTG GAGTTCTATG AGAAGTTCTT TGACATAAAA TTCCCTCTGG AAAAACAAGA     1020

TATGATTGCT CTTCCTGATT TCACCGCTGG TGCCATGGAA AACTGGGGCC TTATCACTTA     1080

TAGAGAGGAT TCTCTCCTAT ACGATGAAAA AATTTATGCA CCGATGAATA AACAGCGGGT     1140

TGCTCTCGTA GTTGCTCACG AGCTTGCTCA TCAGTGGTTC GGCAATCTGG TCACACTGAA     1200

GTGGTGGGAT GATACGTGGT TGAACGAAGG TTTTGCAACA TTTGTTGAGT ATCTTGGAAT     1260

GGACGAAATT AGCCACAACA ATTTCAGAAC GCAAGATTTC TTCTTGCTCG ATGGAATGGA     1320

TCGCGGAATG AGAGCTGACT CGGCAGCATC GAGCCATCCG CTTTCGTTTA GGATTGACAA     1380

AGCGGCAGAA GTTGCCGAAG CCTTTGACGA TATTTCATAC GCCAAGGGAG CGTCAGTTCT     1440

CACTATGCTA CGGGCTTTGA TTGGAGAGGA CAATTACAGG AATGCTGTTG TGCAATACCT     1500

CAAGAAGTTC TCCTACAGCA ATGCACAAGC AGCCGATCTG TGGAACGTCT TCAATGAAGT     1560

TGTCAAAGGT GTTAAGGGTC CTGACGGCAA CGTCATGAAA ATCGACCAAT TTACCGATCA     1620

GTGGACGTAT CAGATGGGTT ATCCTGTGGT TAAAGTAGAA GAATTTAATG CGACCGCCCT     1680

AAAGGTTACG CAGAGCCGGT ACAAGACAAA TAAAGACGCC TTGGAACCAG AGAAATATCG     1740

TAATCCAAAA TACGGGTTCA AGTGGGATGT TCCCCTATGG TATCAGGAAG CAATAGCAA      1800

AGAGGTGAAG CGAACATGGC TAAAAAGAGA TGAACCGCTG TACTTGAACG TCAACAATCG     1860

GGATACATCC CTTGTGGTGA ACGCTGATCG ACATGGATTT TATCGACAAA ACTATGATGC     1920

CAACGGTTGG AAAAAGATAA TCAAGCAGCT CAAGAAAGAT CACAAGGTCT TCGGTCCAAG     1980

GACAAGGAAC GCTATCATAA GCGATGCATT TGCTGCAGCT ACGATGACG CAATCGACTA      2040

TGAAACTGTA TTCGAACTAC TTGAATATGC CAAAAATGAA GAGGAATTCT TGCCTTGGAA     2100

GGAAGCTCTG TCCGGCATGT TCGCAGTTTT AAAGTTCTTC GGTAATGAGC CGGAGACAAA     2160

ACCAGCTAGA GCTTACATGA TGAGCATATT AGAACCGATG TATAATAAGA GCAGCATTGA     2220

TTACATCGTC AAGAATTATT TGGATGATAC GTTATTCACA AAAATTAATA CTCAAAAGGA     2280

TATCATTGAT GCATATTGTT CCCTTGGATC AAAGGACTGT ATAAAGCAAT ATAAGGATAT     2340

CTTCTACGAT GAGGTTATGC CCAAGTGTAA GGCCGGGGAA GCAGCAACCA AATGCGTTAA     2400

GGTTTCCGCT CCTCTTCGAG CCAATGTTTA CTGTTATGGT GTACAGGAAG GTGGTGAAGA     2460

AGCTTTTGAA AAGGTGATGG GGCTGTATCT AGCAGAAGAT GTTCAACTGG AGAAGGGTAT     2520

CCTGTTCAAA GCCTTGGCAT GCCACAAAGA TGTTACAGCT CTAAAAGAAC TTCTTTTGCG     2580

AGCCCTGGAC CGTAAATCGT CGTTTGTGCG TCTTCAGGAT GTCCCTACCG CTTTCCGTGC     2640
```

-continued

| | |
|---|---|
| TGTATCTGAA AACCCTGTGG GCGAAGAATT CATGTTCAAT TTCCTAATGG AGAGATGGGA | 2700 |
| GGAAATCACT GCGAGCTTGG AAACAGAACA CAGAGCAGTT GATAAAGTGG TCGGCGCTTG | 2760 |
| TTGCACAGGA ATTCGCTCCC AACAACAAAT AGATCAGCTG AAGAATCTAC AGAAGAACAA | 2820 |
| TGCGCAGGCT AAGAAGTTCG GCTCATTCAC CCAGGAAATC GAAAAAGGAG AACATAAAAT | 2880 |
| TGCCTGGATC AAGAAACATT TTCACAGATT ATCGGAATTC TTCAAGAGAG CAAGATCATA | 2940 |
| GCTTTTCACA CTGAGCTCCA ATTTTAACGT CTTCAAACTA GGAGACAGTT TTGCTGAAAA | 3000 |
| GTCAGTTTCA CATTTTCCGT TTGAATGCCA TCCATTCGAA TACAACCAAT AATACCATTT | 3060 |
| TAAGTACCTT TCATTCACAG TGATTACTGA ATTTCGAATA TATCATGAAG CTTGTATCTT | 3120 |
| GAACGTTATG ATCGGTGACT TTCAATTTAT AGAGCTCACT CTCCATTTTG TAGCTGTGAT | 3180 |
| GACTTGCATT TAAGACCCAC CATTTACCAG CCTAGAATCT TTCCCCAATA CATTCCAAAC | 3240 |
| TCCGATCACC TCCACCGCTG ACAATGCCCA GATTTGTTTT TTTGTCTGCT ATCCATCTAA | 3300 |
| CTGTTTCGAT CGCCGGTTGT TTGTCAATTG CTTATCTGAT AAATATTGAC GTTGGTGT | 3358 |

(2) INFORMATION FOR SEQ ID NO:21:

(i) SEQUENCE CHARACTERISTICS:
        (A) LENGTH: 3369 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:21:

| | |
|---|---|
| GGTTTAATTA CCCAAGTTTG AGGGTCTCCA TCTAGATGAC GTCGCAGGGG AGAACGCGGA | 60 |
| CATTGCTGAA TCTAACTCCA ATCCGTCTTA TTGTCGCATT ATTTCTAGTA GCTGCTGCAG | 120 |
| TCGGCCTCTC TATTGGTCTC ACCTATTACT TTACTCGCAA AGCGTTCGAT ACCTCAGAAA | 180 |
| AGCCAGGGAA GGATGATACT GGTGGCAAGG ACAAAGACAA TTCTCCCTCT GCGGCGGAAC | 240 |
| TACTCCTTCC AAGTAATATA AAACCATTGT CTTACGACTT GACGATCAAA ACATATCTAC | 300 |
| CTGGTTATGT GGACTTCCCA CCGGAGAAAA ACCTCACATT CGATGGGCGT GTGGAAATAT | 360 |
| CAATGGTTGT AATTGAGCCA ACAAAGAGTA TCGTACTCAA TTCAAAGAAG ATCTCTGTAA | 420 |
| TACCCCAAGA ATGTGAACTG GTATCGGGCG ATAAAAAACT CGAAATTGAA AGTGTAAAGG | 480 |
| AGCACCCAAG ACTGGAAAAG GTTGAGTTTC TTATCAAAAG CCAACTGGAA AAAGATCAAC | 540 |
| AAATCTTGCT CAAGGTCGGC TACATCGGTC TCATCAGCAA CAGCTTTGGT GGAATCTACC | 600 |
| AGACCACTTA TACCACCCCG GATGGCACCC CTAAGATCGC TGCAGTTTCA CAAAATGAGC | 660 |
| CCATAGATGC TCGTCGAATG GTACCATGCA TGGATGAACC GAAATACAAA GCAAACTGGA | 720 |
| CCGTTACTGT CATTCATCCA AAAGGCACCA AGCCGTCTC GAATGGAATC GAAGTGAACG | 780 |
| GAGATGGAGA GATCAGTGGT GATTGGATCA CATCGAAGTT CTTGACTACT CCACGGATGT | 840 |
| CATCCTACTT GTTGGCAGTT ATGGTTTCAG AATTTGAATA CATCGAAGGT GAAACAAAGA | 900 |
| CGGGTGTTCG GTTCCGTATA TGGTCACGCC CAGAGGCAAA GAAGATGACA CAATATGCTC | 960 |
| TGCAATCTGG TATCAAGTGC ATAGAATTCT ACGAAGATTT CTTTGATATC AGATTCCCTC | 1020 |
| TGAAGAAACA AGATATGATT GCCCTTCCTG ATTTCTCTGC CGGTGCCATG GAGAATTGGG | 1080 |
| GCCTCATCAC TTACAGGGAA AACTCTTTGT TGTACGATGA CAGATTCTAT GCACCGATGA | 1140 |

-continued

| | |
|---|---|
| ATAAACAGCG AATTGCTCGC ATTGTTGCTC ATGAGCTTGC TCATCAGTGG TTCGGCGACT | 1200 |
| TGGTTACGAT GAAGTGGTGG GATAATTTGT GGTTGAATGA AGGTTTTGCA AGATTCACAG | 1260 |
| AATTTATTGG AGCTGGTCAG ATAACTCAAG ATGACGCCAG AATGAGGAAC TACTTCCTGA | 1320 |
| TTGATGTACT TGAACGCGCT TTGAAAGCTG ATTCGGTAGC GTCAAGCCAT CCACTTTCCT | 1380 |
| TCAGAATCGA CAAAGCTGCA GAAGTTGAAG AAGCCTTTGA TGATATCACA TACGCCAAAG | 1440 |
| GAGCTTCTGT TCTTACTATG CTGAGAGCCT TGATTGGAGA AGAAAAACAT AAGCATGCAG | 1500 |
| TATCGCAGTA CCTCAAGAAG TTCTCGTATA GCAATGCAGA AGCGACTGAT CTATGGGCAG | 1560 |
| TTTTTGATGA AGTTGTCACT GACGTCGAAG GTCCAGACGG CAAACCTATG AAAACCACAG | 1620 |
| AGTTTGCAAG TCAGTGGACG ACTCAGATGG GCTTCCCAGT TATTTCCGTA GCAGAGTTTA | 1680 |
| ACTCGACTAC TTTGAAATTA ACGCAAAGTC GATATGAGGC GAATAAAGAC GCTGTGGAGA | 1740 |
| AAGAGAAGTA CCGTCACCCG AAATACGGAT TTAAATGGGA TATTCCACTG TGGTATCAGG | 1800 |
| AAGGCGATAA GAAGGAGATA AAGCGAACAT GGTTGAGAAG AGATGAACCG CTTTACTTGC | 1860 |
| ATGTTAGTGA TGCTGGCGCT CCCTTTGTGG TGAACGCAGA CCGCTATGGA TTTTATCGAC | 1920 |
| AAAATCATGA CGCTAATGGT TGGAAAAAGA TAATCAAGCA GCTCAAGGAT AATCATGAGG | 1980 |
| TTTACAGTCC CCGGACAAGG AATGTCATCA TTAGCGATGC GTTTGCTGCG GCTGCAACTG | 2040 |
| ACGCAATTGA GTATGAGACT GTATTTGAAC TTCTGAATTA TGCCGAAAAA GAAACGGAAT | 2100 |
| ATCTACCATT AGAAATCGCA ATGTCCGGGA TCTCTTCGAT TTTGAAATAC TTCCCTACCG | 2160 |
| AGCCAGAGGC AAAGCCAGCT CAAACATACA TGATGAACAT ATTGAAACCG ATGTATGAAA | 2220 |
| AAAGCAGTAT CGACTTCATT GCCAATAACT ACAGAAATGA CAAGCTGTTT TTCCAAATCA | 2280 |
| ACCTCCAAAA AGATGTCATT GATATGTTCT GCGCCCTCGG ATCGCAAGAC TGCAGGAAGA | 2340 |
| AATATAAAAA ACTTTTCGAT GACGAAGTCA TGAACAAATG CAGGGATGGT CAAGCAGCAA | 2400 |
| CCGAATGCGT AAGAATCGCC GCTCCTCTCC GATCAAGTGT TTATTGTTAT GGTGTGAAGG | 2460 |
| AAGGCGGTGA TTATGCTTCC GACAAGGTGA TGGAGCTTTA TACGGCCGAA ACACTCGCCC | 2520 |
| TAGAAAAAGA CTTCCTACGC CTAGCATTGG GATGTCATAA AGATGTTACT GCTTTGAAAG | 2580 |
| GACTTCTCTT GCGGGCTCTG GACAGGAATT CGTCGTTCGT ACGTATGCAG GATATCCCAA | 2640 |
| GTGCTTTCAA CGATGTAGCA GCAAATCCTA TTGGCGAAGA ATTCATTTTC AATTTCCTTA | 2700 |
| TTGAGAGATG GCCAGATATC ATTGAAAGTA TAGGAACGAA GCACACATAT GTTGAGAAAG | 2760 |
| TGATACCAGC CTGCACTTCA GGAATCCGCT CACAACAGCA GATTGACCAG CTGAAGAATC | 2820 |
| TGCAGAAAAA TGGCATGAAC GCTCGTCAAT TCGGTGCATT CGATAAAGCA ATCGAACGAG | 2880 |
| CACAAAATAG GGTGGATTGG ATTAAAAAAC ATTTCCAAAA ATTAGCGGCT TTCTTCAAGA | 2940 |
| AAGCCACCTT GTAATTCGAA TTACATTGCC AGTAATCCAG ATCTTAAAGT TCATGAAGGA | 3000 |
| ATATGACAGG GAACTGACTG TCTGTTGGTC ACTGTTCCAC TGAATGGAAG TTTTTACCTA | 3060 |
| CAAAAATTTT TATCGTTATA TTTGCCTTCC GTGAGGGGTC ATTGTTGTCA CTTGAATAGT | 3120 |
| AAACAAAGCT CAGTATTGGC AACCGTAGAA CAATATTACT TTCGCTTCAT CAAATTGTTA | 3180 |
| TCTTCCCTAT ACCCTCTTCC TAACTGAATT CGGAAATTTG TTCATATTCG TTTGTAGTCT | 3240 |
| GTTGCTCAGA ACACTTTCTC CTCAATAGCT TCTTGTTTGT TTTTTTTTG ATTGTATTGA | 3300 |
| TCGTTTTACA ATTGTATAGA TTAGTTATCT TATAAATATT GATGGTTAAA AAAAAAAAA | 3360 |
| AAAAAAAAA | 3369 |

(2) INFORMATION FOR SEQ ID NO:22:

(i) SEQUENCE CHARACTERISTICS:
    (A) LENGTH: 977 amino acids
    (B) TYPE: amino acid
    (D) TOPOLOGY: linear (ii) MOLECULE TYPE: protein (xi) SEQUENCE DESCRIPTION: SEQ ID NO:22:

```
Met Thr Ala Glu Glu Ser Gln Glu Gln Glu Thr Gln Gln Pro Arg Lys
 1               5                  10                  15

Asn Thr Val Leu Arg Leu Thr Pro Ile Lys Ser Leu Phe Ala Leu Leu
             20                  25                  30

Val Val Ala Ala Ala Val Gly Leu Ser Ile Gly Leu Thr Tyr Tyr Phe
         35                  40                  45

Thr Arg Lys Ala Phe Asp Thr Thr Gly Gly Asn Gly Lys Gly Asp Gln
     50                  55                  60

Pro Ile Val Asp Asp Asn Ser Pro Ser Ala Glu Glu Leu Arg Leu Pro
 65                  70                  75                  80

Thr Thr Ile Lys Pro Leu Thr Tyr Asp Leu Val Ile Lys Thr Tyr Leu
                 85                  90                  95

Pro Asn Tyr Val Asn Tyr Pro Pro Glu Lys Asp Phe Ala Ile Asp Gly
            100                 105                 110

Thr Val Val Ile Ala Met Glu Val Val Glu Pro Thr Lys Ser Ile Val
        115                 120                 125

Leu Asn Ser Lys Asn Ile Pro Val Ile Ala Asp Gln Cys Glu Leu Phe
    130                 135                 140

Ser Asn Asn Gln Lys Leu Asp Ile Glu Lys Val Val Asp Gln Pro Arg
145                 150                 155                 160

Leu Glu Lys Val Glu Phe Val Leu Lys Lys Leu Glu Lys Asn Gln
                165                 170                 175

Lys Ile Thr Leu Lys Ile Val Tyr Ile Gly Leu Ile Asn Asp Met Leu
            180                 185                 190

Gly Gly Leu Tyr Arg Thr Thr Tyr Thr Asp Lys Asp Gly Thr Thr Lys
        195                 200                 205

Ile Ala Ala Cys Thr His Met Glu Pro Thr Asp Ala Arg Leu Met Val
    210                 215                 220

Pro Cys Phe Asp Glu Pro Thr Phe Lys Ala Asn Trp Thr Val Thr Val
225                 230                 235                 240

Ile His Pro Lys Gly Thr Ser Ala Val Ser Asn Gly Ile Glu Lys Gly
                245                 250                 255

Glu Gly Glu Val Ser Gly Asp Trp Val Thr Thr Arg Phe Asp Pro Thr
            260                 265                 270

Pro Arg Met Pro Ser Tyr Leu Ile Ala Leu Val Ile Ser Glu Phe Lys
        275                 280                 285

Tyr Ile Glu Asn Tyr Thr Lys Ser Gly Val Arg Phe Arg Ile Pro Ala
    290                 295                 300

Arg Pro Glu Ala Met Lys Met Thr Glu Tyr Ala Met Ile Ala Gly Ile
305                 310                 315                 320

Lys Cys Leu Asp Tyr Tyr Glu Asp Phe Phe Gly Ile Lys Phe Pro Leu
                325                 330                 335

Pro Lys Gln Asp Met Val Ala Leu Pro Asp Phe Ser Ser Gly Ala Met
            340                 345                 350

Glu Asn Trp Gly Leu Ile Thr Tyr Arg Glu Gly Ser Val Leu Tyr Asp
        355                 360                 365

Glu Asn Leu Tyr Gly Pro Met Asn Lys Glu Arg Val Ala Glu Val Ile
```

-continued

```
        370                 375                 380
Ala His Glu Leu Ala His Gln Trp Phe Gly Asn Leu Val Thr Met Lys
385                 390                 395                 400
Trp Trp Asp Asn Leu Trp Leu Asn Glu Gly Phe Ala Ser Phe Val Glu
                405                 410                 415
Tyr Ile Gly Ala Asp Phe Ile Ser Asp Gly Leu Trp Glu Met Lys Asp
                420                 425                 430
Phe Phe Leu Leu Ala Pro Tyr Thr Ser Gly Ile Thr Ala Asp Ala Val
                435                 440                 445
Ala Ser Ser His Pro Leu Ser Phe Arg Ile Asp Lys Ala Ala Asp Val
                450                 455                 460
Ser Glu Ala Phe Asp Asp Ile Thr Tyr Arg Lys Gly Ala Ser Val Leu
465                 470                 475                 480
Gln Met Leu Leu Asn Leu Val Gly Asp Glu Asn Phe Lys Gln Ser Val
                485                 490                 495
Ser Arg Tyr Leu Lys Lys Phe Ser Tyr Asp Asn Ala Ala Ala Glu Asp
                500                 505                 510
Leu Trp Ala Ala Phe Asp Glu Thr Val Gln Gly Ile Thr Gly Pro Asn
                515                 520                 525
Gly Gly Pro Leu Lys Met Ser Glu Phe Ala Pro Gln Trp Thr Thr Gln
                530                 535                 540
Met Gly Phe Pro Val Leu Thr Val Glu Ser Val Asn Ala Thr Thr Leu
545                 550                 555                 560
Lys Val Thr Gln Lys Arg Tyr Arg Gln Asn Lys Asp Ala Lys Glu Pro
                565                 570                 575
Glu Lys Tyr Arg His Pro Thr Tyr Gly Phe Lys Trp Asp Val Pro Leu
                580                 585                 590
Trp Tyr Gln Glu Asp Glu Gln Gln Val Lys Arg Thr Trp Leu Lys Arg
                595                 600                 605
Glu Glu Pro Leu Tyr Phe His Val Ser Asn Ser Asp Ser Ser Val Val
                610                 615                 620
Val Asn Ala Glu Arg Arg Ala Phe Cys Arg Ser Asn Tyr Asp Ala Asn
625                 630                 635                 640
Gly Trp Arg Asn Ile Met Arg Arg Leu Lys Gln Asn His Lys Val Tyr
                645                 650                 655
Gly Pro Arg Thr Arg Asn Ala Leu Ile Ser Asp Ala Phe Ala Ala Ala
                660                 665                 670
Ala Val Glu Glu Met Asn Tyr Glu Thr Val Phe Glu Met Leu Lys Tyr
                675                 680                 685
Thr Val Lys Glu Glu Asp Tyr Leu Pro Trp Lys Glu Ala Ile Ser Gly
                690                 695                 700
Phe Asn Thr Ile Leu Asp Phe Phe Gly Ser Glu Pro Glu Ser Gln Trp
705                 710                 715                 720
Ala Ser Glu Tyr Met Arg Lys Leu Met Lys Pro Ile Tyr Asp Lys Ser
                725                 730                 735
Ser Ile Lys Phe Ile Ala Glu Asn Tyr Lys Lys Asp Ser Leu Phe Phe
                740                 745                 750
Lys Asn Asn Leu Gln Ile Ala Val Ile Asp Thr Tyr Cys Gly Leu Gly
                755                 760                 765
Gly Lys Glu Cys Leu Glu Glu Met Lys Lys Leu Phe Asp Lys Glu Val
                770                 775                 780
Met Lys Cys Gln Pro Gly Gln Gln Ala Thr Asp Cys Val Lys Val Thr
785                 790                 795                 800
```

```
Ala Pro Leu Arg Lys Thr Val Tyr Cys Tyr Gly Val Gln Glu Gly Gly
                805                 810                 815

Asp Glu Ala Phe Asp Lys Val Met Glu Leu Tyr Asn Ala Glu Gln Val
            820                 825                 830

Gln Leu Glu Lys Asp Ser Leu Arg Glu Ala Leu Gly Cys His Lys Asp
            835                 840                 845

Val Thr Ala Leu Lys Gly Leu Leu Met Leu Ala Leu Asp Arg Asn Ser
        850                 855                 860

Ser Phe Val Arg Leu Gln Asp Ala His Asp Val Phe Asn Ile Val Ser
865                 870                 875                 880

Arg Asn Pro Val Gly Asn Glu Leu Leu Phe Asn Phe Leu Thr Glu Arg
                885                 890                 895

Trp Glu Glu Ile Leu Glu Ser Leu Ser Ile Arg His Arg Ser Val Asp
                900                 905                 910

Arg Val Ile Lys Ala Cys Thr Arg Gly Leu Arg Ser Arg Glu Gln Val
            915                 920                 925

Gln Gln Leu Lys Asn Leu Tyr Lys Asn Asp Lys Arg Ala Arg Glu Tyr
        930                 935                 940

Gly Ala Phe Gly Gly Ala Ile Glu Arg Ser Glu His Arg Val Lys Trp
945                 950                 955                 960

Ile Glu Lys His Phe Arg Lys Leu Ala Ala Phe Phe Lys Lys Ser Asn
                965                 970                 975

Ser (2) INFORMATION FOR SEQ ID NO:23:

(i) SEQUENCE CHARACTERISTICS:
        (A) LENGTH: 972 amino acids
        (B) TYPE: amino acid
        (D) TOPOLOGY: linear (ii) MOLECULE TYPE: protein (xi) SEQUENCE DESCRIPTION: SEQ ID NO:23:

Met Thr Ala Glu Trp Gln Lys Arg Arg Ile Leu Gly Phe Ser Pro Ile
  1               5                  10                  15

Ser Leu Leu Cys Thr Leu Phe Val Leu Ala Ala Val Gly Leu Ser
                20                  25                  30

Ile Gly Leu Thr Tyr Tyr Phe Thr Arg Lys Ala Phe Asp Thr Thr Gln
            35                  40                  45

Lys Glu Gln Lys Asp Asp Ser Gly Gly Lys Glu Lys Asp Asn Ser Pro
 50                  55                  60

Ser Ala Glu Glu Leu Leu Pro Thr Asn Ile Lys Pro Val Ser Tyr
 65                  70                  75                  80

Asp Leu Asn Ile Lys Thr Tyr Leu Pro Gly Tyr Val Asn Phe Pro Pro
                85                  90                  95

Glu Lys Asn Leu Thr Phe Asp Ala His Val Glu Ile Ala Met Val Val
            100                 105                 110

Val Glu Pro Thr Asn Ser Ile Val Leu Asn Ser Lys Lys Ile Thr Leu
        115                 120                 125

Ala Gln Gly Gly Cys Glu Leu Phe Ser Gly Asn Gln Lys Leu Asp Ile
    130                 135                 140

Glu Ser Val Lys Met Gln Glu Arg Leu Asp Lys Leu Glu Ile Thr Leu
145                 150                 155                 160

Lys Asn Gln Leu Gln Lys Asp Leu Lys Ile Leu Leu Lys Ile Thr Tyr
```

-continued

```
            165                 170                 175
Thr Gly Leu Ile Ser Asp Thr Leu Gly Gly Leu Tyr Gln Ser Ile Tyr
            180                 185                 190
Thr Asp Lys Asp Gly Lys Thr Lys Ile Val Ala Val Ser Gln Asn Glu
            195                 200                 205
Pro Ser Asp Ala Arg Arg Ile Ala Pro Cys Phe Asp Glu Pro Lys Tyr
210                 215                 220
Lys Ala Thr Trp Thr Val Thr Val His Pro Lys Gly Thr Lys Ala
225                 230                 235                 240
Ala Ser Asn Gly Ile Glu Ala Asn Gly Lys Gly Leu Lys Gly Asp
            245                 250                 255
Trp Ile Thr Ser Lys Phe Lys Thr Thr Pro Pro Met Ser Ser Tyr Leu
            260                 265                 270
Leu Ala Ile Ile Val Cys Glu Phe Glu Tyr Ile Glu Gly Phe Thr Lys
            275                 280                 285
Thr Gly Val Arg Phe Arg Ile Trp Ser Arg Pro Glu Ala Lys Arg Met
            290                 295                 300
Thr Ala Tyr Ala Leu Asp Ala Gly Ile Arg Cys Leu Glu Phe Tyr Glu
305                 310                 315                 320
Lys Phe Phe Asp Ile Lys Phe Pro Leu Glu Lys Gln Asp Met Ile Ala
            325                 330                 335
Leu Pro Asp Phe Thr Ala Gly Ala Met Glu Asn Trp Gly Leu Ile Thr
            340                 345                 350
Tyr Arg Glu Asp Ser Leu Leu Tyr Asp Glu Lys Ile Tyr Ala Pro Met
            355                 360                 365
Asn Lys Gln Arg Val Ala Leu Val Val Ala His Glu Leu Ala His Gln
            370                 375                 380
Trp Phe Gly Asn Leu Val Thr Leu Lys Trp Trp Asp Asp Thr Trp Leu
385                 390                 395                 400
Asn Glu Gly Phe Ala Thr Phe Val Glu Tyr Leu Gly Met Asp Glu Ile
            405                 410                 415
Ser His Asn Asn Phe Arg Thr Gln Asp Phe Phe Leu Leu Asp Gly Met
            420                 425                 430
Asp Arg Gly Met Arg Ala Asp Ser Ala Ala Ser Ser His Pro Leu Ser
            435                 440                 445
Phe Arg Ile Asp Lys Ala Ala Glu Val Ala Glu Ala Phe Asp Asp Ile
450                 455                 460
Ser Tyr Ala Lys Gly Ala Ser Val Leu Thr Met Leu Arg Ala Leu Ile
465                 470                 475                 480
Gly Glu Asp Asn Tyr Arg Asn Ala Val Val Gln Tyr Leu Lys Lys Phe
            485                 490                 495
Ser Tyr Ser Asn Ala Gln Ala Ala Asp Leu Trp Asn Val Phe Asn Glu
            500                 505                 510
Val Val Lys Gly Val Lys Gly Pro Asp Gly Asn Val Met Lys Ile Asp
            515                 520                 525
Gln Phe Thr Asp Gln Trp Thr Tyr Gln Met Gly Tyr Pro Val Val Lys
            530                 535                 540
Val Glu Glu Phe Asn Ala Thr Ala Leu Lys Val Thr Gln Ser Arg Tyr
545                 550                 555                 560
Lys Thr Asn Lys Asp Ala Leu Glu Pro Glu Lys Tyr Arg Asn Pro Lys
            565                 570                 575
Tyr Gly Phe Lys Trp Asp Val Pro Leu Trp Tyr Gln Glu Gly Asn Ser
            580                 585                 590
```

```
Lys Glu Val Lys Arg Thr Trp Leu Lys Arg Asp Glu Pro Leu Tyr Leu
            595                 600                 605

Asn Val Asn Asn Arg Asp Thr Ser Leu Val Val Asn Ala Asp Arg His
        610                 615                 620

Gly Phe Tyr Arg Gln Asn Tyr Asp Ala Asn Gly Trp Lys Lys Ile Ile
625                 630                 635                 640

Lys Gln Leu Lys Lys Asp His Lys Val Phe Gly Pro Arg Thr Arg Asn
                645                 650                 655

Ala Ile Ile Ser Asp Ala Phe Ala Ala Thr Ile Asp Ala Ile Asp
            660                 665                 670

Tyr Glu Thr Val Phe Glu Leu Leu Glu Tyr Ala Lys Asn Glu Glu Glu
            675                 680                 685

Phe Leu Pro Trp Lys Glu Ala Leu Ser Gly Met Phe Ala Val Leu Lys
        690                 695                 700

Phe Phe Gly Asn Glu Pro Glu Thr Lys Pro Ala Arg Ala Tyr Met Met
705                 710                 715                 720

Ser Ile Leu Glu Pro Met Tyr Asn Lys Ser Ile Asp Tyr Ile Val
                725                 730                 735

Lys Asn Tyr Leu Asp Asp Thr Leu Phe Thr Lys Ile Asn Thr Gln Lys
            740                 745                 750

Asp Ile Ile Asp Ala Tyr Cys Ser Leu Gly Ser Lys Asp Cys Ile Lys
        755                 760                 765

Gln Tyr Lys Asp Ile Phe Tyr Asp Glu Val Met Pro Lys Cys Lys Ala
        770                 775                 780

Gly Glu Ala Ala Thr Lys Cys Val Lys Val Ser Ala Pro Leu Arg Ala
785                 790                 795                 800

Asn Val Tyr Cys Tyr Gly Val Gln Glu Gly Gly Glu Ala Phe Glu
            805                 810                 815

Lys Val Met Gly Leu Tyr Leu Ala Glu Asp Val Gln Leu Glu Lys Gly
                820                 825                 830

Ile Leu Phe Lys Ala Leu Ala Cys His Lys Asp Val Thr Ala Leu Lys
            835                 840                 845

Glu Leu Leu Leu Arg Ala Leu Asp Arg Lys Ser Ser Phe Val Arg Leu
        850                 855                 860

Gln Asp Val Pro Thr Ala Phe Arg Ala Val Ser Glu Asn Pro Val Gly
865                 870                 875                 880

Glu Glu Phe Met Phe Asn Phe Leu Met Glu Arg Trp Glu Glu Ile Thr
                885                 890                 895

Ala Ser Leu Glu Thr Glu His Arg Ala Val Asp Lys Val Val Gly Ala
            900                 905                 910

Cys Cys Thr Gly Ile Arg Ser Gln Gln Gln Ile Asp Gln Leu Lys Asn
        915                 920                 925

Leu Gln Lys Asn Asn Ala Gln Ala Lys Lys Phe Gly Ser Phe Thr Gln
        930                 935                 940

Glu Ile Glu Lys Gly Glu His Leu Ile Ala Trp Ile Lys Lys His Phe
945                 950                 955                 960

His Arg Leu Ser Glu Phe Phe Lys Arg Ala Arg Ser
                965                 970
```

(2) INFORMATION FOR SEQ ID NO:24:

(i) SEQUENCE CHARACTERISTICS:
        (A) LENGTH: 972 amino acids
        (B) TYPE: amino acid (D) TOPOLOGY: linear (ii) MOLECULE TYPE: protein (xi) SEQUENCE DESCRIPTION: SEQ ID NO:24:

```
Met Thr Ser Gln Gly Arg Thr Arg Thr Leu Leu Asn Leu Thr Pro Ile
 1               5                  10                  15

Arg Leu Ile Val Ala Leu Phe Leu Val Ala Ala Ala Val Gly Leu Ser
            20                  25                  30

Ile Gly Leu Thr Tyr Tyr Phe Thr Arg Lys Ala Phe Asp Thr Ser Glu
        35                  40                  45

Lys Pro Gly Lys Asp Asp Thr Gly Gly Lys Asp Lys Asp Asn Ser Pro
    50                  55                  60

Ser Ala Ala Glu Leu Leu Leu Pro Ser Asn Ile Lys Pro Leu Ser Tyr
65                  70                  75                  80

Asp Leu Thr Ile Lys Thr Tyr Leu Pro Gly Tyr Val Asp Phe Pro Pro
                85                  90                  95

Glu Lys Asn Leu Thr Phe Asp Gly Arg Val Glu Ile Ser Met Val Val
            100                 105                 110

Ile Glu Pro Thr Lys Ser Ile Val Leu Asn Ser Lys Lys Ile Ser Val
        115                 120                 125

Ile Pro Gln Glu Cys Glu Leu Val Ser Gly Asp Lys Lys Leu Glu Ile
    130                 135                 140

Glu Ser Val Lys Glu His Pro Arg Leu Glu Lys Val Glu Phe Leu Ile
145                 150                 155                 160

Lys Ser Gln Leu Glu Lys Asp Gln Gln Ile Leu Leu Lys Val Gly Tyr
                165                 170                 175

Ile Gly Leu Ile Ser Asn Ser Phe Gly Gly Ile Tyr Gln Thr Thr Tyr
            180                 185                 190

Thr Thr Pro Asp Gly Thr Pro Lys Ile Ala Ala Val Ser Gln Asn Glu
        195                 200                 205

Pro Ile Asp Ala Arg Arg Met Val Pro Cys Met Asp Glu Pro Lys Tyr
    210                 215                 220

Lys Ala Asn Trp Thr Val Thr Val Ile His Pro Lys Gly Thr Lys Ala
225                 230                 235                 240

Val Ser Asn Gly Ile Glu Val Asn Gly Asp Gly Glu Ile Ser Gly Asp
                245                 250                 255

Trp Ile Thr Ser Lys Phe Leu Thr Thr Pro Arg Met Ser Ser Tyr Leu
            260                 265                 270

Leu Ala Val Met Val Ser Glu Phe Glu Tyr Ile Glu Gly Glu Thr Lys
        275                 280                 285

Thr Gly Val Arg Phe Arg Ile Trp Ser Arg Pro Glu Ala Lys Lys Met
    290                 295                 300

Thr Gln Tyr Ala Leu Gln Ser Gly Ile Lys Cys Ile Glu Phe Tyr Glu
305                 310                 315                 320

Asp Phe Phe Asp Ile Arg Phe Pro Leu Lys Lys Gln Asp Met Ile Ala
                325                 330                 335

Leu Pro Asp Phe Ser Ala Gly Ala Met Glu Asn Trp Gly Leu Ile Thr
            340                 345                 350

Tyr Arg Glu Asn Ser Leu Leu Tyr Asp Asp Arg Phe Tyr Ala Pro Met
        355                 360                 365

Asn Lys Gln Arg Ile Ala Arg Ile Val Ala His Glu Leu Ala His Gln
    370                 375                 380

Trp Phe Gly Asp Leu Val Thr Met Lys Trp Trp Asp Asn Leu Trp Leu
```

-continued

```
            385                 390                 395                 400
Asn Glu Gly Phe Ala Arg Phe Thr Glu Phe Ile Gly Ala Gly Gln Ile
                    405                 410                 415
Thr Gln Asp Asp Ala Arg Met Arg Asn Tyr Phe Leu Ile Asp Val Leu
                420                 425                 430
Glu Arg Ala Leu Lys Ala Asp Ser Val Ala Ser Ser His Pro Leu Ser
            435                 440                 445
Phe Arg Ile Asp Lys Ala Ala Glu Val Glu Glu Ala Phe Asp Asp Ile
        450                 455                 460
Thr Tyr Ala Lys Gly Ala Ser Val Leu Thr Met Leu Arg Ala Leu Ile
465                 470                 475                 480
Gly Glu Glu Lys His Lys His Ala Val Ser Gln Tyr Leu Lys Lys Phe
                485                 490                 495
Ser Tyr Ser Asn Ala Glu Ala Thr Asp Leu Trp Ala Val Phe Asp Glu
                500                 505                 510
Val Val Thr Asp Val Glu Gly Pro Asp Gly Lys Pro Met Lys Thr Thr
            515                 520                 525
Glu Phe Ala Ser Gln Trp Thr Thr Gln Met Gly Phe Pro Val Ile Ser
        530                 535                 540
Val Ala Glu Phe Asn Ser Thr Thr Leu Lys Leu Thr Gln Ser Arg Tyr
545                 550                 555                 560
Glu Ala Asn Lys Asp Ala Val Glu Lys Glu Lys Tyr Arg His Pro Lys
                565                 570                 575
Tyr Gly Phe Lys Trp Asp Ile Pro Leu Trp Tyr Gln Glu Gly Asp Lys
                580                 585                 590
Lys Glu Ile Lys Arg Thr Trp Leu Arg Arg Asp Glu Pro Leu Tyr Leu
            595                 600                 605
His Val Ser Asp Ala Gly Ala Pro Phe Val Val Asn Ala Asp Arg Tyr
        610                 615                 620
Gly Phe Tyr Arg Gln Asn His Asp Ala Asn Gly Trp Lys Lys Ile Ile
625                 630                 635                 640
Lys Gln Leu Lys Asp Asn His Glu Val Tyr Ser Pro Arg Thr Arg Asn
                645                 650                 655
Val Ile Ile Ser Asp Ala Phe Ala Ala Ala Thr Asp Ala Ile Glu
                660                 665                 670
Tyr Glu Thr Val Phe Glu Leu Leu Asn Tyr Ala Glu Lys Glu Thr Glu
            675                 680                 685
Tyr Leu Pro Leu Glu Ile Ala Met Ser Gly Ile Ser Ser Ile Leu Lys
        690                 695                 700
Tyr Phe Pro Thr Glu Pro Glu Ala Lys Pro Ala Gln Thr Tyr Met Met
705                 710                 715                 720
Asn Ile Leu Lys Pro Met Tyr Glu Lys Ser Ser Ile Asp Phe Ile Ala
                725                 730                 735
Asn Asn Tyr Arg Asn Asp Lys Leu Phe Phe Gln Ile Asn Leu Gln Lys
                740                 745                 750
Asp Val Ile Asp Met Phe Cys Ala Leu Gly Ser Gln Asp Cys Arg Lys
            755                 760                 765
Lys Tyr Lys Lys Leu Phe Asp Asp Glu Val Met Asn Lys Cys Arg Asp
        770                 775                 780
Gly Gln Ala Ala Thr Glu Cys Val Arg Ile Ala Ala Pro Leu Arg Ser
785                 790                 795                 800
Ser Val Tyr Cys Tyr Gly Val Lys Glu Gly Asp Tyr Ala Ser Asp
                805                 810                 815
```

```
Lys Val Met Glu Leu Tyr Thr Ala Glu Thr Leu Ala Leu Glu Lys Asp
            820                 825                 830

Phe Leu Arg Leu Ala Leu Gly Cys His Lys Asp Val Thr Ala Leu Lys
            835                 840                 845

Gly Leu Leu Arg Ala Leu Asp Arg Asn Ser Ser Phe Val Arg Met
            850                 855                 860

Gln Asp Ile Pro Ser Ala Phe Asn Asp Val Ala Ala Asn Pro Ile Gly
865                 870                 875                 880

Glu Glu Phe Ile Phe Asn Phe Leu Ile Glu Arg Trp Pro Asp Ile Ile
                885                 890                 895

Glu Ser Ile Gly Thr Lys His Thr Tyr Val Glu Lys Val Ile Pro Ala
            900                 905                 910

Cys Thr Ser Gly Ile Arg Ser Gln Gln Gln Ile Asp Gln Leu Lys Asn
            915                 920                 925

Leu Gln Lys Asn Gly Met Asn Ala Arg Gln Phe Gly Ala Phe Asp Lys
            930                 935                 940

Ala Ile Glu Arg Ala Gln Asn Arg Val Asp Trp Ile Lys Lys His Phe
945                 950                 955                 960

Gln Lys Leu Ala Ala Phe Phe Lys Lys Ala Thr Leu
                965                 970

(2) INFORMATION FOR SEQ ID NO:25:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:25:

Met Gly Tyr Pro Val Val Lys Val Glu Glu Phe
1               5                   10

(2) INFORMATION FOR SEQ ID NO:26:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (iii) HYPOTHETICAL: NO (xi) SEQUENCE DESCRIPTION: SEQ ID NO:26:

Met Gly Phe Pro Val Leu Thr Val Glu Ser
1               5                   10

(2) INFORMATION FOR SEQ ID NO:27:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:27:

Met Xaa Asn Phe Lys Ile Xaa Xaa Ala Gly
```

```
1               5                  10
```

(2) INFORMATION FOR SEQ ID NO:28:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:28:

```
Met Lys Xaa Xaa Leu Xaa Xaa Leu Xaa Ile Thr
1               5                  10
```

(2) INFORMATION FOR SEQ ID NO:29:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

```
Met Leu Ala Leu Asp Tyr His Ser Xaa Phe Val
1               5                  10
```

(2) INFORMATION FOR SEQ ID NO:30:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:30:

```
Met Leu Ala Xaa Asp Xaa Glu Asp Val
1               5
```

(2) INFORMATION FOR SEQ ID NO:31:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

```
Met Gly Phe Pro Leu Val Thr Val Glu Ala Phe Tyr
1               5                  10
```

(2) INFORMATION FOR SEQ ID NO:32:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

```
Met Lys Thr Pro Glu Phe Ala Xaa Gln Ala Xaa Ala Thr Xaa Phe Pro
1               5                   10                  15
```

(2) INFORMATION FOR SEQ ID NO:33:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:33:

```
Lys Xaa Xaa Ser Pro Ala Ala Glu Xaa Leu Xaa
1               5                   10
```

(2) INFORMATION FOR SEQ ID NO:34:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

```
Lys Xaa Thr Ser Val Ala Glu Ala Phe Asn
1               5                   10
```

(2) INFORMATION FOR SEQ ID NO:35:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:35:

```
Lys Ala Ala Glu Val Ala Glu Ala Phe Asp Xaa Ile Xaa Xaa Xaa Lys
1               5                   10                  15
Gly
```

(2) INFORMATION FOR SEQ ID NO:36:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

```
Lys Ala Val Glu Xaa Ala Glu Ala Phe Asp Asp Ile Thr Tyr Xaa Xaa
1               5                   10                  15
Gly Pro Ser
```

(2) INFORMATION FOR SEQ ID NO:37:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:37:

Lys Xaa Glu Gln Thr Glu Ile Phe Asn Met
1               5                   10

(2) INFORMATION FOR SEQ ID NO:38:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:38:

Lys Xaa Xaa Xaa Pro Phe Xaa Ile Glu Ala Leu
1               5                   10

(2) INFORMATION FOR SEQ ID NO:39:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:39:

Asp Gln Ala Phe Ser Thr Asp Ala Lys
1               5

(2) INFORMATION FOR SEQ ID NO:40:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:40:

Met Gly Tyr Pro Val Val Lys Val Glu Glu Phe Xaa Ala Thr Ala Leu
1               5                   10                  15

(2) INFORMATION FOR SEQ ID NO:41:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:41:

Met Gly Phe Pro Val Leu Thr Val Glu Ser Xaa Tyr Xaa Thr
1               5                   10

(2) INFORMATION FOR SEQ ID NO:42:

(i) SEQUENCE CHARACTERISTICS:
        (A) LENGTH: 13 amino acids
        (B) TYPE: amino acid
        (C) STRANDEDNESS:

(D) TOPOLOGY: linear (ii) MOLECULE TYPE: peptide (xi) SEQUENCE DESCRIPTION: SEQ ID NO:42:

Met Xaa Asn Phe Leu Ile Xaa Xaa Ala Gly Xaa Ile Thr
1               5                   10

(2) INFORMATION FOR SEQ ID NO:43:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide xi) SEQUENCE DESCRIPTION: SEQ ID NO:43:

Met Gly Phe Leu Val Thr Val Glu Ala Phe Tyr Xaa Thr Ser
1               5                   10

(2) INFORMATION FOR SEQ ID NO:44:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:44:

Met Lys Thr Pro Glu Phe Ala Xaa Gln Ala Xaa Ala Thr Xaa Phe Pro
1               5                   10                  15

(2) INFORMATION FOR SEQ ID NO:45:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:45:

Met Lys Xaa Xaa Leu Xaa Xaa Leu Xaa Ile Thr Xaa Gly
1               5                   10

(2) INFORMATION FOR SEQ ID NO:46:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:46:

Met Leu Ala Leu Asp Tyr His Ser Xaa Phe Val Gly
1               5                   10

(2) INFORMATION FOR SEQ ID NO:47:

(i) SEQUENCE CHARACTERISTICS:
        (A) LENGTH: 9 amino acids
        (B) TYPE: amino acid (C) STRANDEDNESS:
          (D) TOPOLOGY: linear (ii) MOLECULE TYPE: peptide (xi) SEQUENCE DESCRIPTION: SEQ ID NO:47:

Met Leu Ala Xaa Asp Xaa Glu Asp Val
1               5

(2) INFORMATION FOR SEQ ID NO:48:

(i) SEQUENCE CHARACTERISTICS:
          (A) LENGTH: 11 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:48:

Lys Xaa Xaa Ser Pro Ala Ala Glu Xaa Leu Xaa
1               5                   10

(2) INFORMATION FOR SEQ ID NO:49:

(i) SEQUENCE CHARACTERISTICS:
          (A) LENGTH: 10 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:49:

Lys Xaa Thr Ser Val Ala Glu Ala Phe Asn
1               5                   10

(2) INFORMATION FOR SEQ ID NO:50:

(i) SEQUENCE CHARACTERISTICS:
          (A) LENGTH: 17 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:50:

Lys Ala Ala Glu Val Ala Glu Ala Phe Asp Xaa Ile Xaa Xaa Xaa Lys
1               5                   10                  15

Gly (2) INFORMATION FOR SEQ ID NO:51:

(i) SEQUENCE CHARACTERISTICS:
          (A) LENGTH: 19 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:51:

Lys Ala Val Glu Xaa Ala Glu Ala Phe Asp Asp Ile Thr Tyr Xaa Xaa
1               5                   10                  15

Gly Pro Ser (2) INFORMATION FOR SEQ ID NO:52:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:52:

```
Lys Xaa Glu Gln Thr Glu Ile Phe Asn Met
1               5                   10
```

(2) INFORMATION FOR SEQ ID NO:53:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:53:

```
Lys Xaa Xaa Xaa Pro Phe Xaa Ile Glu Ala Leu
1               5                   10
```

(2) INFORMATION FOR SEQ ID NO:54:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:54:

```
Asp Gln Ala Phe Ser Thr Asp Ala Lys
1               5
```

(2) INFORMATION FOR SEQ ID NO:55:

(i) SEQUENCE CHARACTERISTICS:
        (A) LENGTH: 8 bases
        (B) TYPE: nucleic acid
        (C) STRANDEDNESS: double
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:55:

```
GGAATTCC                                                              8
```

(2) INFORMATION FOR SEQ ID NO:56:

(i) SEQUENCE CHARACTERISTICS:
        (A) LENGTH: 12
        (B) TYPE: nucleic acid
        (C) STRANDEDNESS: double
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:56:

```
CCGGAATTCC GG                                                        12
```

(2) INFORMATION FOR SEQ ID NO:57:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:57:

GACTCGAGTC GACATCGATT TTTTTTTTTT TTTTT           35

(2) INFORMATION FOR SEQ ID NO:58:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:58:

ACGGGTGTTC GGTTTCCGTA T           21

(2) INFORMATION FOR SEQ ID NO:59:

(i) SEQUENCE CHARACTERISTICS:
        (A) LENGTH: 20 nucleic acids
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:59:

GCTGAATCTA ACTCCAATCC           20

(2) INFORMATION FOR SEQ ID NO:60:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

SEQUENCE DESCRIPTION: SEQ ID NO:60:

AAGCG GATGGCTTGA NGC           23

(2) INFORMATION FOR SEQ ID NO:61:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:61:

TGTTGTGGCT AATTTCGTCC A           21

(2) INFORMATION FOR SEQ ID NO:62:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:62:

CATCTTNAGT TATCTGACCA G                                           21

(2) INFORMATION FOR SEQ ID NO:63:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:63:

GACCATCGCT GATGAAGTCG G                                           21

(2) INFORMATION FOR SEQ ID NO:64:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:64:

CUACUACUAC UAGGCCACGC GTCGACTAGT ACGGGNNGGG NNGGGNNG              48

(2) INFORMATION FOR SEQ ID NO:65:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:65:

TCTTGAAGAA ATGAAAAAGC TT                                          22

(2) INFORMATION FOR SEQ ID NO:66:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 12..30

(xi) SEQUENCE DESCRIPTION: SEQ ID NO:66:

GGATCCGATT G CTG AAT CTA ACT CCA ATC  C                            30

Leu Asn Leu Thr Pro Ile
 1               5

(2) INFORMATION FOR SEQ ID NO:67:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:67:

Leu Asn Leu Thr Pro Ile
 1               5

(2) INFORMATION FOR SEQ ID NO:68:

(i) SEQUENCE CHARACTERISTICS:
        (A) LENGTH: 8 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "linker"

(xi) SEQUENCE DESCRIPTION: SEQ ID NO:68:

CGGATCCG                                                            8

(2) INFORMATION FOR SEQ ID NO:69:

(i) SEQUENCE CHARACTERISTICS:
        (A) LENGTH: 8 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "linker"

(xi) SEQUENCE DESCRIPTION: SEQ ID NO:69:

CCCATGGG                                                            8

(2) INFORMATION FOR SEQ ID NO:70:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 9..41

(xi) SEQUENCE DESCRIPTION: SEQ ID NO:70:

GGATCCCC ATG GGG ATC CGA TTG CTG AAT CTA ACT CCA ATC C              42
         Met Gly Ile Arg Leu Leu Asn Leu Thr Pro Ile
              10                  15

(2) INFORMATION FOR SEQ ID NO:71:

-continued

```
    (i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:71:

Met Gly Ile Arg Leu Leu Asn Leu Thr Pro Ile
 1               5                  10

(2) INFORMATION FOR SEQ ID NO:72:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:72:

His Glu Xaa Xaa His Xaa Trp
 1               5

(2) INFORMATION FOR SEQ ID NO:73:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (xi) SEQUENCE DESCRIPTION: SEQ ID NO:73:

GGTTTAATTA CCCAAGTTTG AG                                              22
```

RECOMBINANT DNA MOLECULES ENCODING AMINOPEPTIDASE ENZYMES AND THEIR USE IN THE PREPARATION OF VACCINES AGAINST HELMINTH INFECTIONS

This application is a 371 of PCT/GB93/00943 filed May 7, 1997 which claims priority of Great Britain application 9209993.6 filed May 8, 1992.

The present invention relates to the preparation of protective antigens by recombinant DNA technology for use as anthelmintic agents and as protective immunogens in the control of diseases caused by helminth parasites.

Helminth parasites are responsible for a wide range of diseases and infestations of domestic animals which, leading as they do to loss of production and even animal mortality, are of considerable economic importance. Thus for example, the blood feeding nematode Haemonchus infects the lining of the gastrointestinal tract of ruminants, causing anaemia and weight loss and if untreated frequently leads to death. Animals infected with the related non-blood feeding nematode Ostertagia similarly fail to thrive and may die if untreated. Other genera of helminths of economic importance include Trichostrongylus and Nematodirus which cause enteritis in various animal, and trematodes.

Problems are also caused by nematodes such as hookworms (eg. Hecator, Ancylostoma, Uncinaria and Bunostomum spp) and flukes (eg. Fasciola, Paramphistomum and Dicrocoelium) and their relatives which in addition to ruminants and domestic pets, also infect humans, frequently with fatal results.

Control of helminth parasites presently relies primarily on the use of anthelmintic drugs combined with pasture management. Such techniques have a number of drawbacks however—frequent administration of drugs and pasture management are often not practical, and drug-resistant helminth strains are becoming increasingly widespread.

There is a therefore a need in this field for an effective anti-helminth vaccine and many efforts have been concentrated in this area in recent years. However, as yet there are no commercially available molecular or sub-unit vaccines for the major helminth species, particularly for the gastrointestinal nematodes of ruminants, such as Haemonchus and Ostertagia.

Most promising results to date have been obtained with novel proteins isolated from Haemonchus, which have potential as protective antigens not only against Haemonchus but also against a range of other helminths. In particular the protein doublet H110D, found at the luminal surface of the intestine of *H. contortus* has been shown to confer protective immunity against haemonchosis in sheep.

H110D from *H. contortus* has an approximate molecular weight of 110 kilodaltons (kd) under reducing and non-reducing conditions, as defined by SDS-PAGE, and is describe din WO 88/00835 and WO 90/11086. The term "H110D" as used herein refers to the protein doublet H110D as defined in WO 88/00835 and WO 90/11086. Corresponding proteins have also recently been shown in other helminth species, eg. *Necator americanus.*

A number of methods for the purification of H110D have ben described in WO 88/00835 which suffice for the characterisation of the protein, and may be scaled up to permit production of the protein in experimentally and commercially useful quantities. There is however a need for an improved and convenient source from which to prepare not only H110D but also related antigenic proteins, especially for a process based on recombinant DNA technology and expression of the proteins in suitably transformed prokaryotic or eukaryotic organisms.

The present invention seeks to provide such an improved procedure. Sequence determination of cDNAs for H110D from *Haemonchus contortus* has been performed and the predicted amino acid sequences have been found to display homology with a family of integral membrane aminopeptidases (systematic name: α-amino acyl peptide hydrolase (microsomal)).

The mammalian integral membrane aminopeptidases are located in several tissues, eg. on the microvillar brush border of intestines, and kidney. Their role in the kidney is unclear, but in the intestine their function is to cleave the small peptides which are the final products of digestion (for reviews, see Kenny & Maroux, 1982; Kenny & Turner, 1987; Noren et al, 1986; Semenza, 1986).

In one aspect the present invention thus provides nucleic acid molecules comprising one or more nucleotide sequences which encode helminth aminopeptidase enzymes or antigenic portions thereof substantially corresponding to all or a portion of the nucleotide sequences as shown in FIGS. 2, 3, 4 or 5 (SEQ ID NOS:1 to 15 and 19 to 21) or sequences coding for helminth aminopeptidase enzymes which are substantially homologous with or which hybridise with any of said sequences.

A nucleic acid according to the invention may thus be single or double stranded DNA, cDNA or RNA.

Variations in the aminopeptidase-encoding nucleotide sequences may occur between different strains of helminth within a species, between different stages of a helminth life cycle (e.g. between larval and adult stages), between similar strains of different geographical origin, and also within the same helminth. Such variations are included within the scope of this invention.

"Substantially homologous" as used herein includes those sequences having a sequence identity of approximately 50% or more, eg. 60% or more, and also functionally-equivalent allelic variants and related sequences modified by single or multiple base substitution, addition and/or deletion. By "functionally equivalent" is meant nucleic acid sequences which encode polypeptides having aminopeptidase activities which are similarly immunoreactive ie. which raise host protective antibodies against helminths.

Nucleic acid molecules which hybridise with the sequences shown in FIGS. 2, 3, 4 or 5 (composed of SEQ ID NOS:1 to 15 and 19 to 21) or any substantially homologous or functionally equivalent sequences as defined above are also included within the scope of the invention. "Hybridisation" is used herein defines those sequences binding under non-stringent conditions (6× SSC/50% formamide at room temperature) and washed under conditions of low stringency (2× SSC, room temperature, more preferably 2× SSC, 42° C.) or conditions of higher stringency eg. 2× SSC, 65° C. (where SSC=0.15M NaCl, 0.015M sodium citrate, pH 7.2).

Methods for producing such derivative related sequences, for example by site-directed mutagenesis, random mutagenesis, or enzymatic cleavage and/or ligation of nucleic acids are well known in the art, as are methods for determining whether the thus-modified nucleic acid has significant homology to the subject sequence, for example by hybridisation.

Provision of a nucleic acid molecule according to the invention thus enables recombinant aminopeptidase enzymes, or immunogenic fragments thereof, to be obtained in quantities heretofore unavailable, thereby permitting the development of anti-helminth vaccines.

In another aspect the present invention thus provides nucleic acid molecules comprising one or more nucleotide sequences encoding one or more polypeptides capable of raising protective antibodies against helminth parasites, which sequences incorporate one or more antigenic determinant-encoding regions from the aminopeptidase-encoding sequences as shown in FIGS. 2, 3, 4 or 5 (composed from SEQ ID NOS:1 to 15 and 19 to 21).

The present invention also extends to synthetic polypeptides comprising one or more amino acid sequences constituting an aminopeptidase enzyme or antigenic portions thereof, substantially corresponding to all or a portion of the nucleotide sequences as shown in FIG. 2, 3, 4 or 5 (SEQ ID NOS:1 to 15), or a functionally-equivalent variant thereof other than a synthetic polypeptide corresponding to the protein doublet H110D, or a synthetic polypeptide corresponding to any of the individual polypeptide sequences disclosed in WO 90/11086.

Alternatively viewed, the invention also provides synthetic polypeptides comprising an amino acid sequence constituting an aminopeptidase enzyme or an antigenic portion thereof, substantially corresponding to all or a portion of the nucleotide sequences as shown in FIG. 2, 3, 4 or 5 (SEQ ID NOS:1 to 15) or a functionally-equivalent variant thereof, substantially free from other *Haemonchus contortus* components.

The invention further extends to vaccine compositions for stimulating immune responses against helminth parasites in a human or non-human animal, comprising at least one synthetic polypeptide as defined above, together with a pharmaceutically acceptable carrier.

WO 90/11086 discloses a number of polypeptide or partial polypeptide sequences (SEQ ID NO:25–54) obtained by proteolytic digestion or chemical cleavage of the protein doublet H110D as follows:

```
(a)    Met Gly Tyr Pro Val Val Lys Val Glu Glu
       Phe
(b)    Met Gly Phe Pro Val Leu Thr Val Glu Ser
(c)    Met Gly/Phe Asn Phe Lys Ile Glu/VAl Thr/Glu
       Ala Gly
(d)    Met Lys Pro/Glu Thr/Val Lys Asp/Ala Thr/Lys
       Leu - Ile Thr
(e)    Met Leu Ala Leu Asp Tyr His Ser - Phe Val
(f)    Met Leu Ala Glu/Tyr Asp Gln/Ala Glu Asp Val
(g)    Met Gly Phe Pro Leu Val Thr Val Glu Ala
       Phe Tyr
(h)    Met Lys Thr Pro Glu Phe Ala Val/Leu Gln
       Ala Phe/Thr Ala Thr Ser/Gly Phe Pro
(i)    Lys His/Tyr Asn/Val Ser Pro Ala Ala Glu
       Asn/Leu Leu Asn/Gly
(j)    Lys - Thr Ser Val Ala Glu Ala Phe Asn
(k)    Lys Ala Ala Glu Val Ala Glu Ala Phe Asp -
       Ile - - - Lys Gly
(l)    Lys Ala Val Glu Val/Pro Ala Glu Ala Phe
       Asp Asp Ile Thr? Tyr - - Gly Pro Ser
(m)    Lys - Glu Glu Thr Glu Ile Phe Asn Met
(n)    Lys - - - Pro Phe Asn/Asp Ile Glu Ala
       Leu
(o)    Asp Gln Ala Phe Ser Thr Asp Ala Lys
(p)    Met Gly Tyr Pro Val Val Lys Val Glu Glu
       Phe -Ala Thr Ala Leu
(q)    Met Gly Phe Pro Val Leu Thr Val Glu Ser -
       Tyr? - Thr
(r)    Met Glu/Phe Asn Phe Leu Ile Glu/Val Thr/Glu
       Ala Gly - Ile Thr
(s)    Met Gly Phe Leu Val Thr Val Glu Ala Phe
       Tyr - Thr Ser
(t)    Met Lys Thr Pro Glu Phe Ala Val/Leu Gln
       Ala Phe/Thr Ala Thr Ser/Gly Phe Pro
(u)    Met Lys Pro/Glu Thr/Val Leu Asp/Ala Thr/Lys
       Leu - Ile Thr - Gly
(v)    Met Leu Ala Leu Asp Tyr His Ser - Phe Val
       Gly?
(w)    Met Leu Ala Glu/Tyr Asp Gln/Ala Glu Asp Val
(x)    Lys His/Tyr Asn/Val Ser Pro Ala Ala Glu
       Asn/Leu Leu Asn/Gly
(y)    Lys - Thr Ser Val Ala Glu Ala Phe Asn
(z)    Lys Ala Ala Glu Val Ala Glu Ala Phe Asp -
       Ile - - - Lys Gly
(aa)   Lys Ala Val Glu Val/Pro Ala Glu Ala Phe
       Asp Asp Ile Thr? Tyr - - Gly Pro Ser
(bb)   Lys - Glu Gln Thr Glu Ile Phe Asn Met
(cc)   Lys - - - Pro Phe Asn/Asp Ile Glu
       Ala Leu
(dd)   Asp Gln Ala Phe Ser Thr Asp Ala Lys
```

Uncertainties are shown either by the form Phe/Gly, where the first three letter code represents the most likely correct amino acid based on the strength of the signal, or by a question mark; a sigh "-" means an unknown residue.

The specific individual polypeptide sequences which are disclosed in WO 09/11086 are disclaimed.

The term "polypeptide" as used herein includes both full length protein, and shorter peptide sequences.

"Functionally equivalent" as used above in relation to the polypeptide amino acid sequences defines polypeptides related to or derived from the above-mentioned polypeptide sequences where the amino acid sequence has been modified by single or multiple amino acid substitution, addition or deletion, and also sequences where the amino acids have been chemically modified, including by glycosylation or deglycosylation, but which nonetheless retain protective antigenic (immunogenic) activity. Such functionally-equivalent variants may occur as natural biological variations or may be prepared using known techniques, for example functionally equivalent recombinant polypeptides may be prepared using the known techniques of site-directed mutagenesis, random mutagenesis, or enzymatic cleavage and/or ligation of amino acids.

Generally, the synthetic polypeptides according to the invention represent protective antigenic sequences. The term "protective antigen" as used herein defines those antigens capable of generating a host-protective (immunogenic) immune response ie. a response by the host which leads to the generation of immune effector molecules, antibodies or cells which sterilise the fecundity of, damage, inhibit or kill the parasite and thereby "protect" the host from clinical or sub-clinical disease and loss of productivity. Such a protective immune response may commonly be manifested by the generation of antibodies which are able to inhibit the metabolic function of the parasite, leading to stunting, lack of egg production and/or death.

The synthetic polypeptides according to this aspect of the invention may be prepared by expression in a host cell containing a recombinant DNA molecule which comprises a nucleotide sequence as broadly described above operatively linked to an expression control sequence, or a recombinant DNA cloning vehicle or vector containing such a recombinant DNA molecule. Alternatively the polypeptides may be expressed by direct injection of a naked DNA molecule according to the invention into a host cell.

The synthetic polypeptide so expressed may be a fusion polypeptide comprising a portion displaying the immunogenicity of all or a portion of an aminopeptidase enzyme and an additional polypeptide coded for by the DNA of the recombinant molecule fused thereto. For example, it may be desirable to produce a fusion protein comprising a synthetic aminopeptidase or other polypeptide according to the invention coupled to a protein such as β-galactosidase, phosphatase, glutathione-S-transferase, urease, hepatitis B core antigen (Francis et al., 1989) and the like. Most fusion proteins are formed by expression of a recombinant gene in which two coding sequences have been joined together with reading frames in phase. Alternatively, polypeptides can be linked in vitro by chemical means. All such fusion or hybrid derivatives of aminopeptidase-encoding nucleic acid molecules and their respective amino acid sequences are encompassed by the present invention. Such suitable recombinant DNA and polypeptide expression techniques are described for example in Sambrook et al., 1989. Alternatively, the synthetic polypeptides may be produced by chemical means, such as the well-known Merrifield solid phase synthesis procedure.

Further aspects of the invention include use of a nucleic acid molecule or a synthetic peptide or polypeptide as defined above, for the preparation of a vaccine composition for stimulating immune responses in a human or non-human, preferably mammalian animal against helminth parasite infections.

Alternatively viewed, the invention also provides a method of stimulating an immune response in a human or non-human, preferably mammalian, animal against a helminth parasite infection comprising administering to said animal a vaccine composition comprising one or more polypeptides encoded by a nucleotide sequence as defined above.

A vaccine composition may be prepared according to the invention by methods well known in the art of vaccine manufacture. Traditional vaccine formulations may comprise one or more synthetic polypeptides according to the invention together, where appropriate, with one or more suitable adjuvants, eg. aluminum hydroxide, saponin, QuilA, or more purified forms thereof, muramyl dipeptide, mineral oils, or Novasomes, in the presence of one or more pharmaceutically acceptable carriers or diluents. Suitable carriers include liquid media such as saline solution appropriate for use as vehicles to introduce the peptides or polypeptides into a patient. Additional components such as preservatives may be included.

An alternative vaccine formulation may comprise a virus or host cell eg. a microorganism (eg. vaccinia virus, adenovirus, Salmonella) having inserted therein a nucleic acid molecule (eg. a DNA molecule) according to this invention for stimulation of an immune response directed against polypeptides encoded by the inserted nucleic acid molecule.

Administration of the vaccine composition may take place by any of the conventional routes, eg. orally or parenterally such as by intramuscular injection, optionally at intervals eg. two injections at a 7–28 day interval.

As mentioned above, the amino acid translation of the nucleotide sequences depicted in FIGS. 2, 3, 4 or 5 show sequence homology with a family of integral membrane aminopeptidase enzymes. This was determined by searching various databases available in the Genetics Computer Group Sequence analysis software package, version 7.01, November 1991 (Devereux et al., (1984)), using transitions of the sequences shown in FIGS. 2, 3, 4 or 5. Two such comparisons are shown in FIG. 6.

Expression of the aminopeptidase-encoding sequences according to the invention can, as mentioned above, be achieved using a range of known techniques and expression systems, including expression in prokaryotic cells such as *E. coli* and in eukaryotic cells such as yeasts of the baculovirus-insect cell system or transformed mammalian cells and in transgenic animals and plants. Particularly advantageously, the nucleotide sequences may be expressed using the transgenic nematode system such as the system for the nematode Caenorhabditis described for example in Fire, (1986); Fire et al., (1989); Spieth et al., (1988); Han et al., (1990).

A further aspect of the invention provides a method for preparing a synthetic polypeptide as defined above which comprises culturing a eukaryotic or prokaryotic cell containing a nucleic acid molecule as defined above, under conditions whereby said polypeptide is expressed, and recovering said polypeptide thus produced.

Further aspects of the invention thus include cloning and expression vectors containing nucleotide sequences according to the invention. Such expression vectors include appropriate control sequences such as for example translational (eg. start and stop codes) and transcriptional control elements (eg. promoter-operator regions, ribosomal binding sites, termination stop sequences) linked in matching reading frame with the nucleic acid molecules of the invention.

Vectors according to the invention may include plasmids and viruses (including both bacteriophage and eukaryotic viruses) according to techniques well known and documented in the art, and may be expressed in a variety of different expression systems, also well known and documented in the art. Suitable viral vectors include, as mentioned above, baculovirus and also adenovirus and vaccinia viruses. Many other viral vectors are described in the art.

A variety of techniques are known and may be used to introduce such vectors into prokaryotic or eukaryotic cells for expression, or into germ line or somatic cells to form transgenic animals. Suitable transformation or transfection techniques are well described in the literature.

Transformed or transfected eukaryotic or prokaryotic host cells or transgenic organisms containing a nucleic acid molecule according to the invention as defined above, form a further aspect of the invention.

Eukaryotic expression systems in general, and the nematode expression system in particular, have the advantage that post-translational processing, and particularly glycosylation can occur—in the case of the transgenic nematode system, a glycosylation corresponding to that found in the native protein may be expected. This represents an important aspect of the invention, since in many cases post-translational processing is required for the recombinant protein to express optimum biological activity.

Mammalian cell expression systems, also have a number of advantages. Mammalian host cells provide good reproduction of the native form and protective epitopes of the antigen since a eukaryotic expression system will give rise to more similar glycosylation patterns, disulphide bonding and other post-translational modifications than E. coli which may produce an insoluble protein requiring refolding and having poor reproduction of the native form. In addition mammalian glycosylation is unlikely to induce an immune response which distracts from a protective anti-protein response. For protection of humans and domestic animals, it is thus preferable to use human or animal fibroblast or myeloma cell lines such as HeLa—a human cell line; BHK—baby hamster kidney cells; VERO, a monkey kidney cell line; FR3T3, Fisher rate fibroblasts; NIH3T3, a mouse fibroblast cell line; C127I, a mouse mammary tumour cell line; CV-1, African green monkey kidney fibroblasts: 3T6, mouse embryo fibroblasts; L cells, a mouse cell line; CHO, a Chinese Hamster Ovary cell line; NSO NSI, SP2 and other mouse myeloma cell lines and rat myeloma cell lines such as YB2/0 and Y3.

Vectors appropriate for different classes of mammalian cell lines are well known in the art. In general, these will comprise a promoter and/or enhancer operably connected to a nucleotide sequence encoding the antigen or fragment thereof. Suitable promoters include SV40 early or late promoter, eg. PSVL vector, cytomegalovirus (CMV) promoter, mouse metallothionein I promoter and mouse mammary tumour virus long terminal repeat. The vector preferably includes a suitable marker such as a gene for dihydrofolate reductase or glutamine synthetase. Vectors of those types are described in WO 86/05807, WO 87/04462, WO 89/01036 and WO 89/10404.

Transfection of the host cells may be effected using standard techniques, for example using calcium phosphate, DEAE dextran, polybrene, protoplast fusion, liposomes, direct microinjection, gene cannon or electroporation. The latter technique is preferred and methods of transfection of mammalian cell lines using electroporation are described by Andreason et al., 1980. In general, linear DNA is introduced more readily than circular DNA.

In the case of the protein H110D, it has been found to have a unique and unusual glycosylation pattern, which is thought to contribute to immunoactivity since many monoclonal antibodies so far obtained to H110D from Haemonchus recognise carbohydrate epitopes which may be of importance in developing useful vaccines.

In particular the following glycosylation pattern for H110D from Haemonchus has been demonstrated:
i. about 65% of oligosaccharides are N-linked, the remainder O-linked;
ii. the major part (eg. about 48%) of the N-linked oligosaccharide is of the complex class;
iii. substantially all (eg. greater than 95%) of the oligosaccharides are uncharged;
iv. the relative molar content of the constituent monosaccharides is N-acetylgalactosamine 1.0, fucose 3.6, galactose 4.1, glucose 4.4, mannose 6.2 and N-acetylglucosamine 5.2;
v. the oligosaccharides, other than the major oligosaccharide (designated oligosaccharide D), are substantially resistant to degradation by a broad range of exoglycosidases (eg. α-D-mannosidase, β-D-mannosidase, β-D-glucosidase, β-D-galactosidase, α-D-galactosidase, α-L-fucosidase, β-D-xylosidase, β-D-N-acetylglucosaminidase).

Such oligosaccharides and glycoproteins containing them form a further aspect of this invention.

Oligosaccharide D of the Haemonchus H110D glycoprotein is of the N-linked type and has a novel structure consisting of two fucose residues attached by an α-1,3 linkage and an α-1,2 linkage to a mannose (N-acetylglucosamine)$_2$ core.

Another aspect of the invention thus provides an oligosaccharide having the structure:

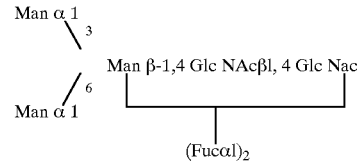

and more particularly the structure:

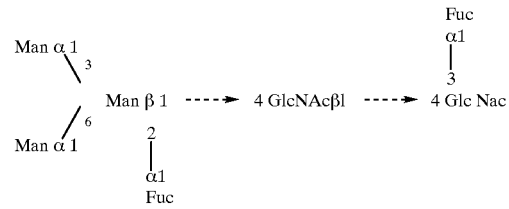

especially when linked to a protein, eg. a recombinant protein such as a helminth aminopeptidase protein or an antigenic fragment thereof, or when used to generate anti-idiotypic antigens for immunisation especially of very young animals.

Animal glycoproteins generally have fucose α-1,6 linkages and the fucose α-1,3 linkage of the oligosaccharide of the present invention is an unusual feature.

This invention will now be described in more detail with particular reference to the protein H110D from *Haemonchus contortus*. However, by a variety of techniques such as a histochemistry and DNA hybridisation, H110D equivalents have been observed in other parasite species. It is believed that the H110D protein is a multigene complex and that in addition, the nucleotide sequences encoding it, may exhibit sequence variations between different strains and different life cycle stages of the helminth. Moreover there may exist multiple enzyme forms (isoenzymes) which may be differentially expressed at different stages, or in different strains. In this study DNA sequences, and thus the predicted amino acid sequences, have been determined from cDNA clones and PCR products obtained from mRNA corresponding to the H110D gene by recombinant DNA technology from different sources, and at different parasitic stages of *H. contortus* life cycle.

Sequencing of cDNA and PCR products has enabled us to identify three closely related H110D sequences which are here designated H11-1 (SEQ ID NO:19), H11-2 (SEQ ID NO:20) and H11-2 (SEQ ID NO:21). H11-1 comprises three contiguous and overlapping sequences, cDNA clone AustB1 (SEQ ID NO:6), PCR product A-648 (SEQ ID NO:9) and at the 3' end PCR product 014-178 (SEQ ID NO:12); H11-2 comprises the PCR products A-650 and 2.5 kb (SEQ ID NOS:10 and 7 respectively); H11-3 comprises the PCR products 3.5 kb and A-649 (SEQ ID NOS:8 and 11 respectively). The specific relationships between the individual sequenced cDNA and PCR product clones and H11-1, -2 and -3 are summarised in FIG. 1 and shown in detail in FIGS. 3, 4 and 5.

Differences and variations in the sequences obtained from the cDNA clones and PCR products have been observed, as can be seen in particular from FIGS. 2, 3, 4 and 5 (composed of SEQ ID NOS:1 to 15 and 19 to 21) and as summarised in Table 1.

TABLE 1

Homologies of the deduced amino acid sequences obtained by translation of the nucleotide sequences shown in FIG. 2.

|  | % Similarity | % Identity |
|---|---|---|
| H11-1:H11-2 | 77 | 63 |
| H11-1:H11-3 | 79 | 65 |
| H11-2:H11-3 | 82 | 69 |

The differences can be attributed to different mRNAs )of the multigene family). In addition, the variations may be due, at least in part, to different variants of the H110D-encoding sequence or mRNA present at different stages of the life cycle or in strains differing in geographical origin.

Table 2 additionally shows levels of identity and similarity between the corresponding predicted amino acid sequences and two published mammalian aminopeptidase sequences.

TABLE 2

Homologies of the H110D amino acid sequences with rat aminopeptidase M (ApM) and mouse aminopeptidase A (ApA).

|  | % Similarity | % Identity |
|---|---|---|
| H11-1:ApM | 55 | 32 |
| H11-1:ApA | 55 | 31 |
| H11-2:ApM | 52 | 31 |
| H11-2:ApA | 54 | 31 |
| H11-3:ApM | 53 | 32 |
| H11-3:ApA | 52 | 30 |

FIG. 1 shows a map of the *H. contortus H*110D cDNA and PCR product clones sequenced and their relationships and relative positions along the H110D mRNA;

FIG. 2 shows the H110D nucleotide sequences designated H11-3, (SEQ ID NO:21, derived from cloned PCR products SEQ ID NOS:8 and 11 and cDNA clone M1AUS, SEQ ID NO:5), H11-2 (SEQ ID NO:20, derived from cloned PCR products SEQ ID NOS:7 and 10) and H11-1 (SEQ ID NO:19, derived from cloned PCR products SEQ ID NOS:9 and 12 and cDNA clone AustB1, SEQ ID NO:6);

FIG. 3 shows the sequence H11-3 (SEQ ID NO:21) (shown in FIG. 2) with alignment of the cDNA clones M1 and M1AUS (SEQ ID NOS:1 and 5);

FIG. 4 shows the sequence H11-2 (SEQ ID NO:20, shown in FIG. 2) and the alignment of the cDNA clone B2 (SEQ ID NO:4);

FIG. 5 shows that the sequence designated H11-1 (SEQ ID NO:19) and alignment of the cDNA B1A and Aust B1 (SEQ ID NOS:2 and 6 respectively);

Figure 6A:
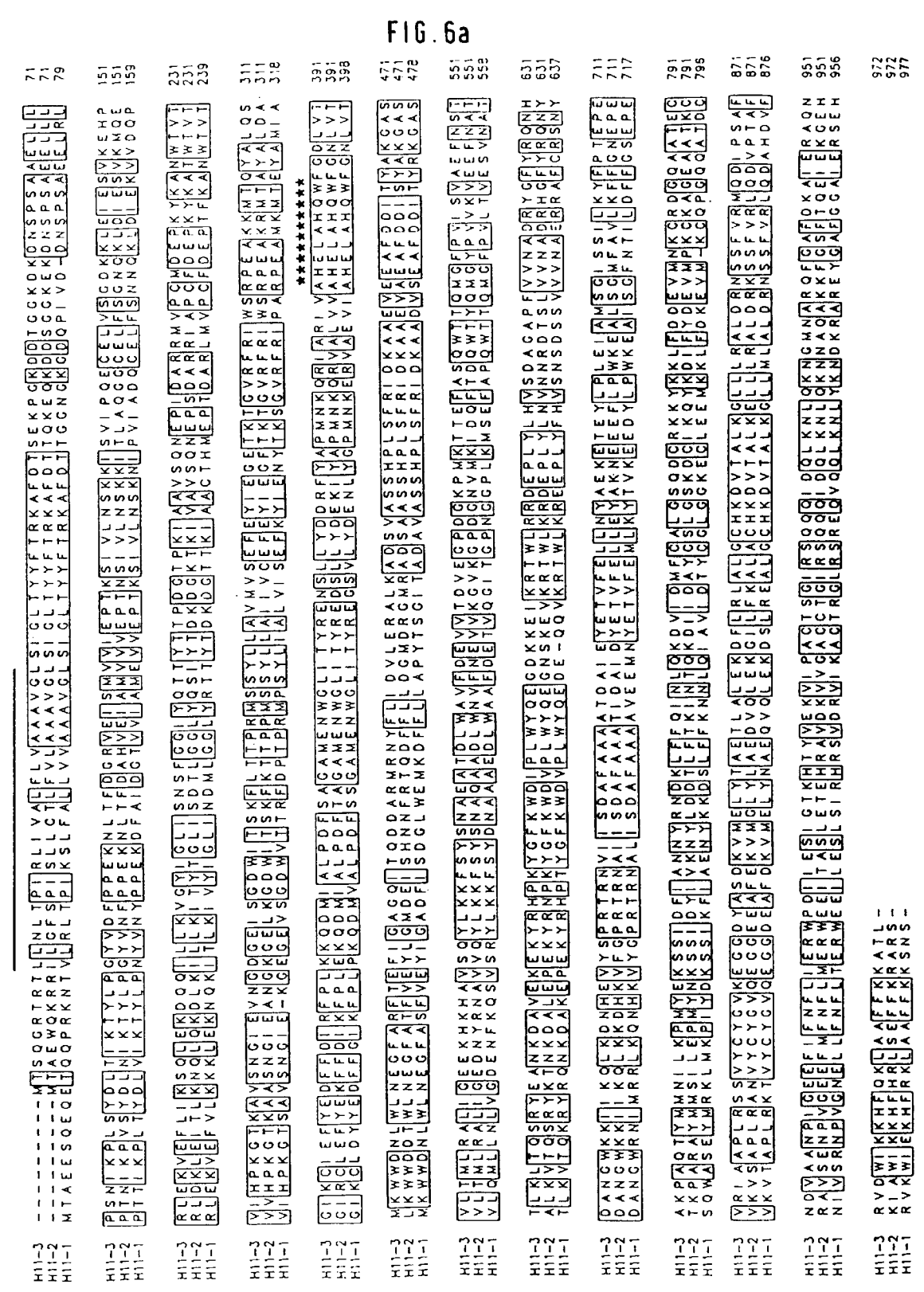
Figure 6B1:
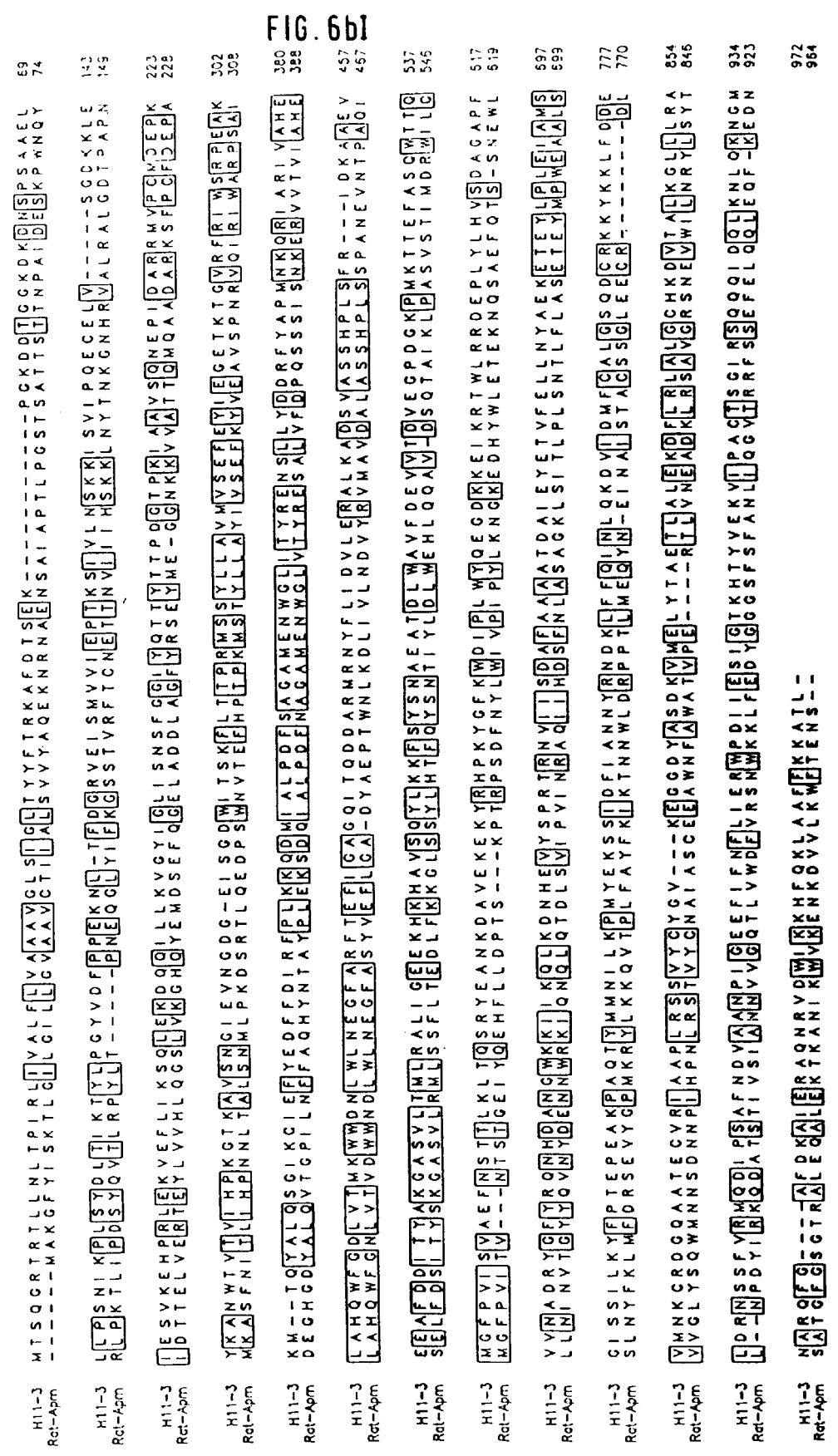
Figure 6:
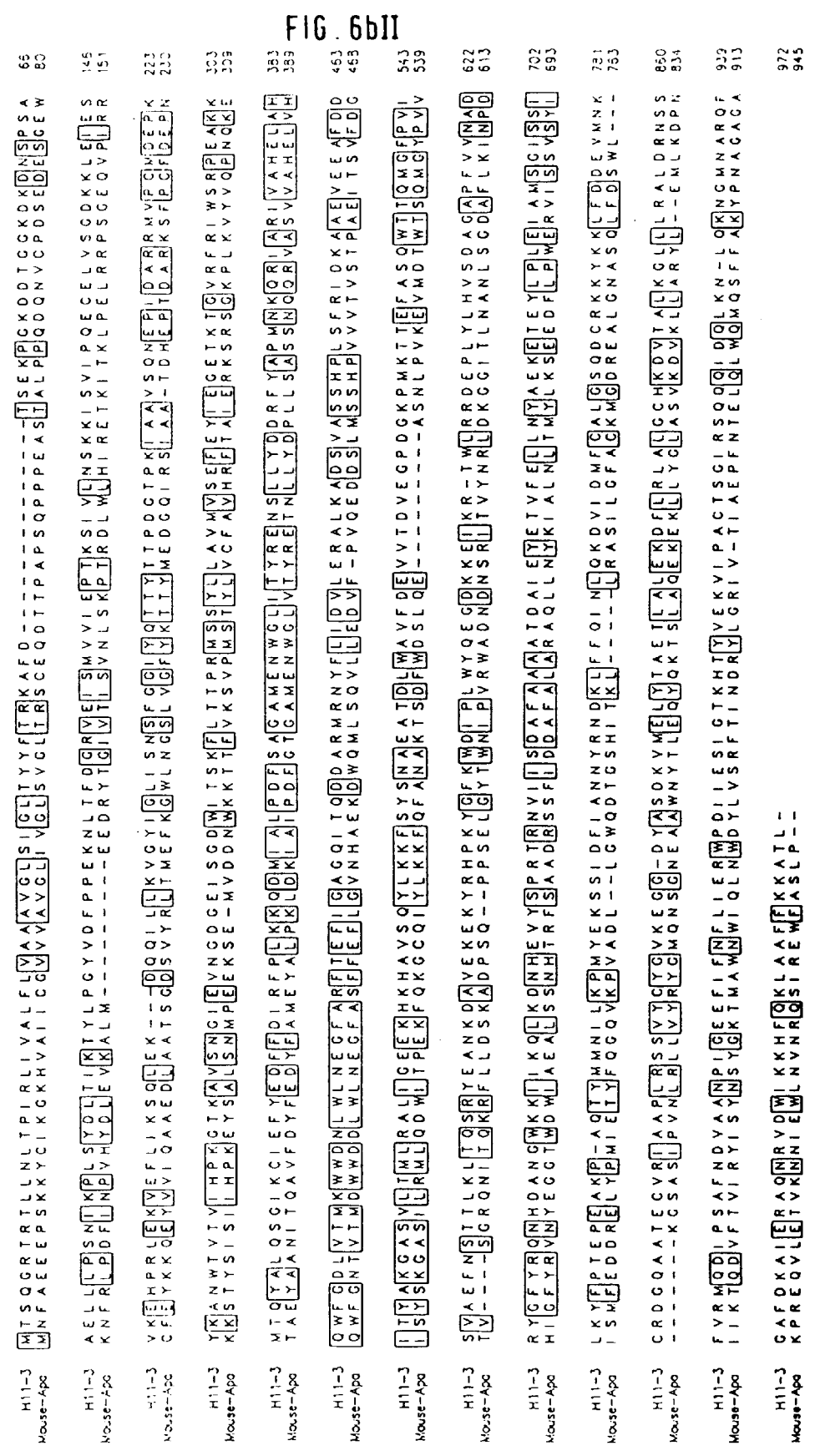
Figure 1:
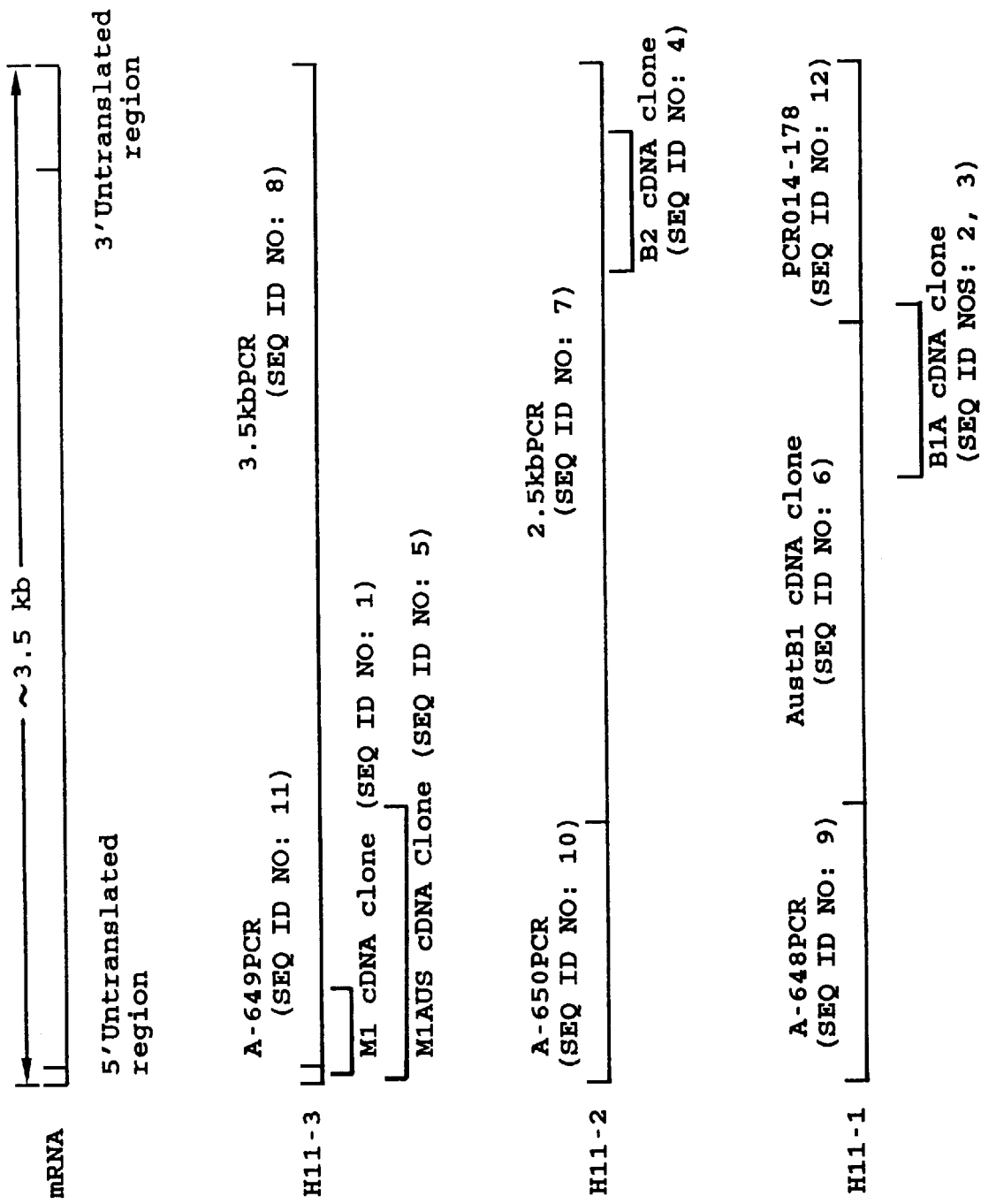

FIG. 6 shows A) the predicted amino acid sequences (SEQ ID NOS:22, 23 and 24) derived from the DNA sequences H11-1, H11-2 and H11-3 shown in FIG. 2; bi) and ii) show the predicted amino acid sequence of H11-3 compared with the published amino acid sequences of rat microsomal aminopeptidase M (Watt et al., 1989) and mouse microsomal aminopeptidase A (Wu et al., 1990) respectively; identities are enclosed in boxes,, dashes indicate spaces introduced to maximise the level of homology between the compared sequences. The conventional single letter code for amino acids is used. The horizontal line above the sequence indicates the position of the transmembrane region and the asterisks show the position of the zinc-binding motif. Levels of similarity are shown in Tables 1 and 2;

FIG. 7 shows the alignments of amino acid sequences (designated Pep A, Pep B, Pep C, Pep D and Pep E) obtained from CNBr and Lys-C fragments of H110D as previously described (International patent application WO 90/11086 and as listed earlier, polypeptide sequences (a), (b), (e), (k) and (aa), respectively) and three new sequences (SEQ ID NOS:16, 17 and 18) obtained from H110D following digestion by elastase or thermolysin with the translations of a) H11-1, b) H11-2 and c) H11-3.

In a further aspect the invention also provides nucleic acid molecules comprising one or more nucleotide sequences which substantially correspond to or which are substantially complementary to one or more sequences selected from the sequences of clones M1, B1A, B1A-3', B2, M1AUS, AustB1, 014-015 (2.5 PCR), 014-872 (3.5 PCR clone 2), A-648 (5' end of B1), A-650 (5' end of 2.5 PCR), A649 (5' end of 3.5 PCR), 014-178 (3' end of AustB1 clone 2), 014-178 (3' end of AustB1 clones 3 & 6), 014-872 (3.5 PCR clone 10) and 014-872 (3.5 PCR clone 19), H11-1, H11-2 and H11-3, SEQ ID NOS:1 to 15 and 19 to 21 respectively as shown in FIGS. 2, 3, 4, and 5 or sequences which are substantially homologous with or which hybridise with any of the said sequences.

As mentioned above, comparison of the sequences of various of the clones mentioned above, against computer databases of known sequences, reveals substantial homology with the family of microsomal aminopeptidase enzymes (EC. 3.4.11.-). Enzymological activity and inhibitor studies performed with the H110D protein and sub-fractions thereof confirm that the protein is in fact microsomal aminopeptidase (α-amino acyl peptide hydrolase (microsomal)). Such studies have further shown that both aminopeptidase A-like and aminopeptidase M-like activities are exhibited, and that each of the components of the H110D doublet individually exhibit enzyme activity.

Studies with proteolytic digestion of H110D have also been carried out. Using the enzyme elastase, it was found that H110D may be partially cleaved, forming two fractions, a detergent-soluble fraction (which remained with the membrane) and a water-soluble fraction (which is designated H11S). H11S occurs in the form of a protein dimer which may be reduced to two components. Interestingly, it was found that only aminopeptidase M-like activity is associated with the water-soluble H11S fraction, whereas aminopeptidase A-like activity is only associated with the detergent-soluble fraction.

Figure 8:
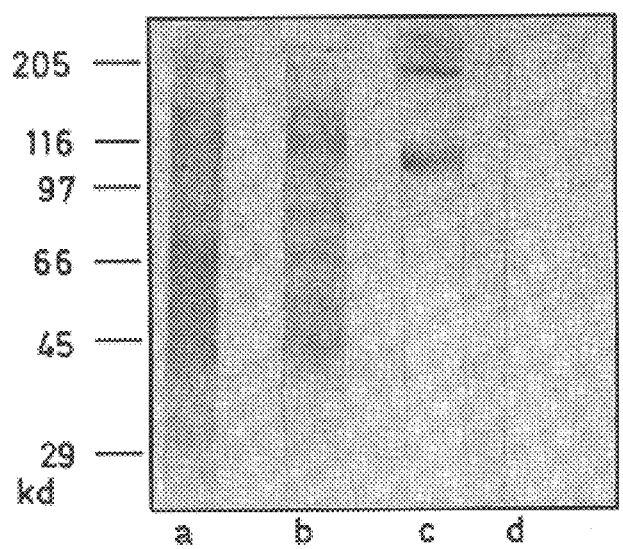
Figure 20:
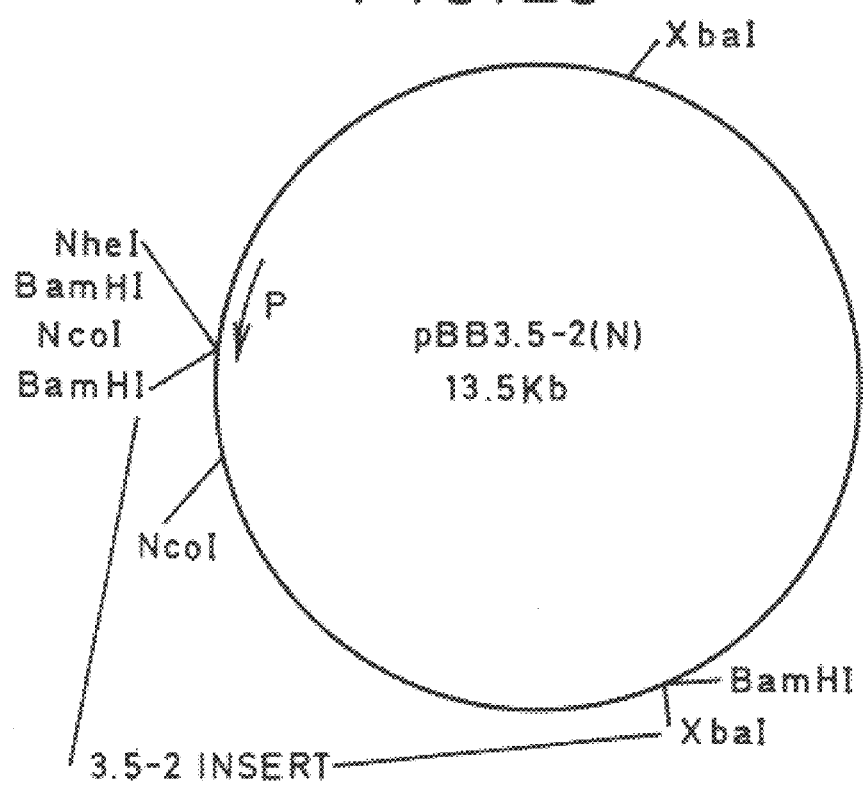
Figure 9:
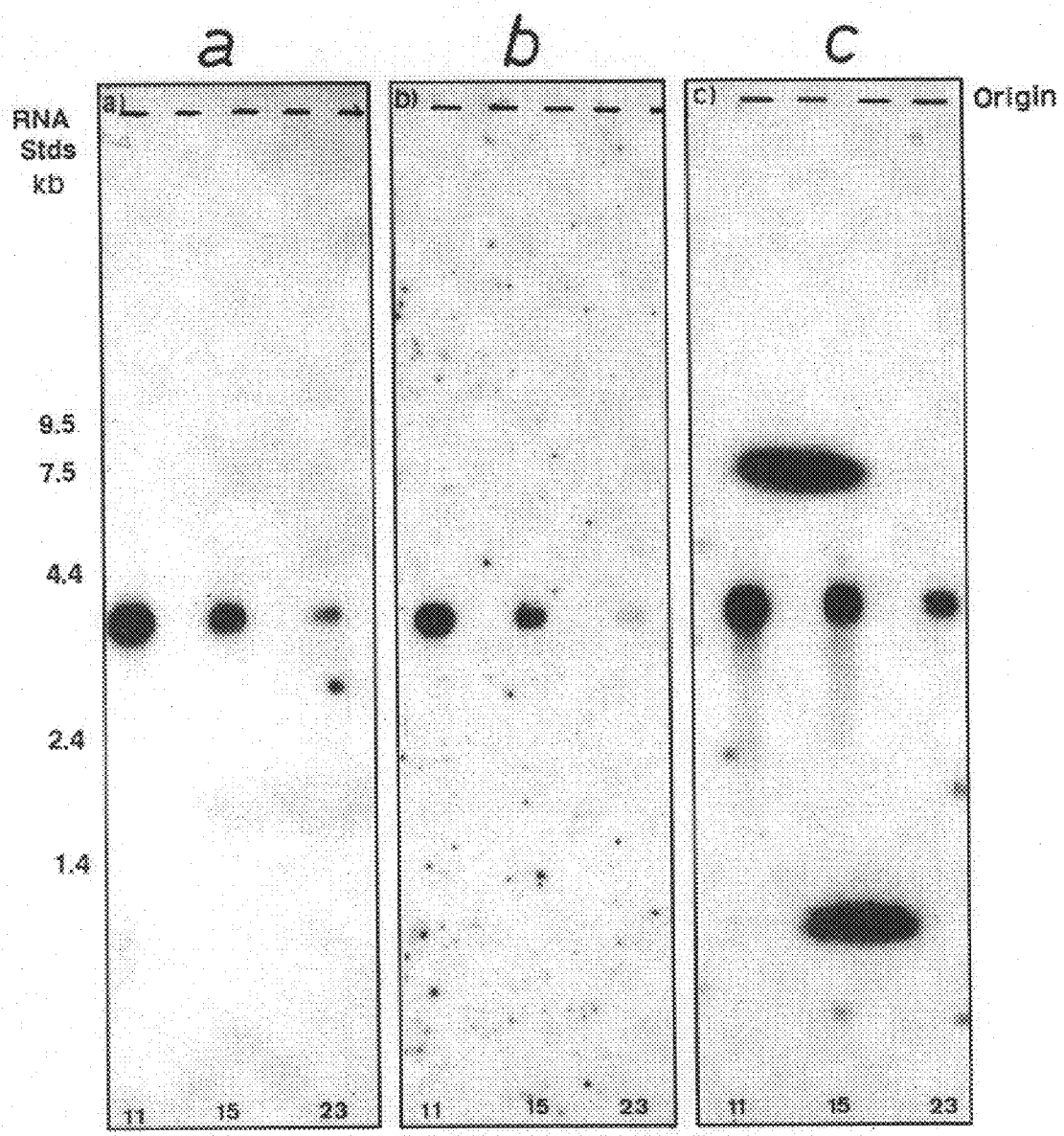
Figure 9:
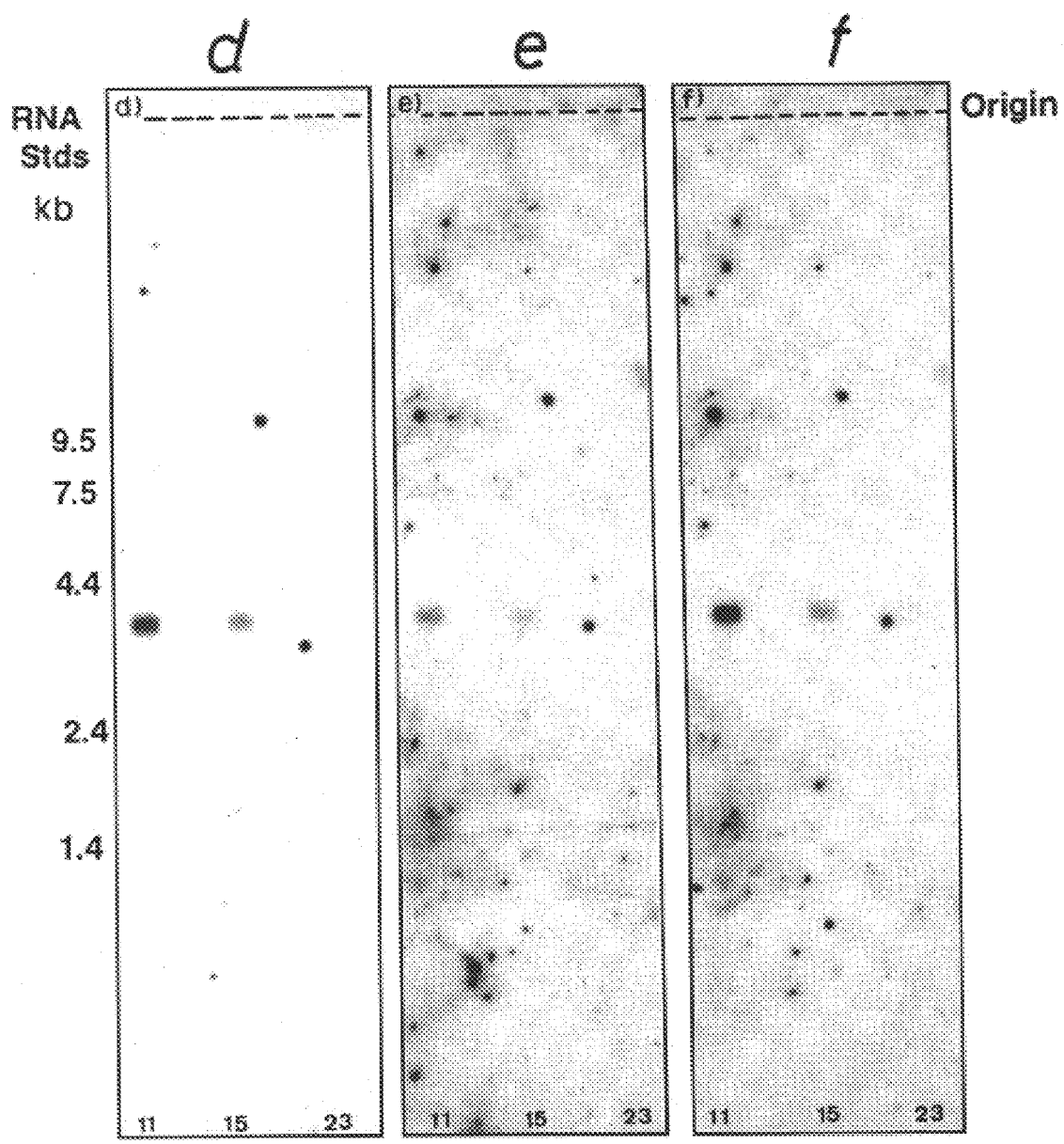
Figure 10A:
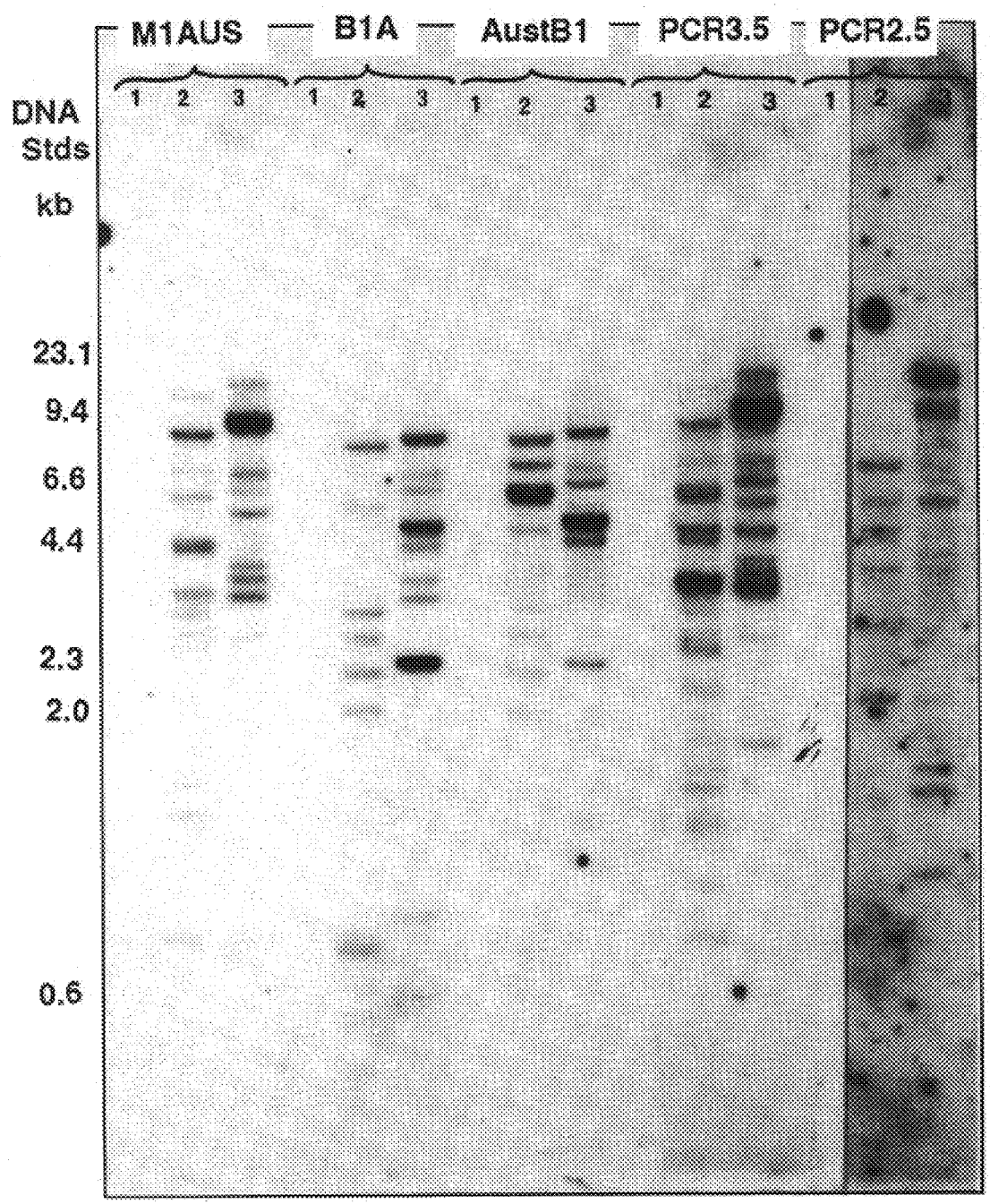
Figure 10B:
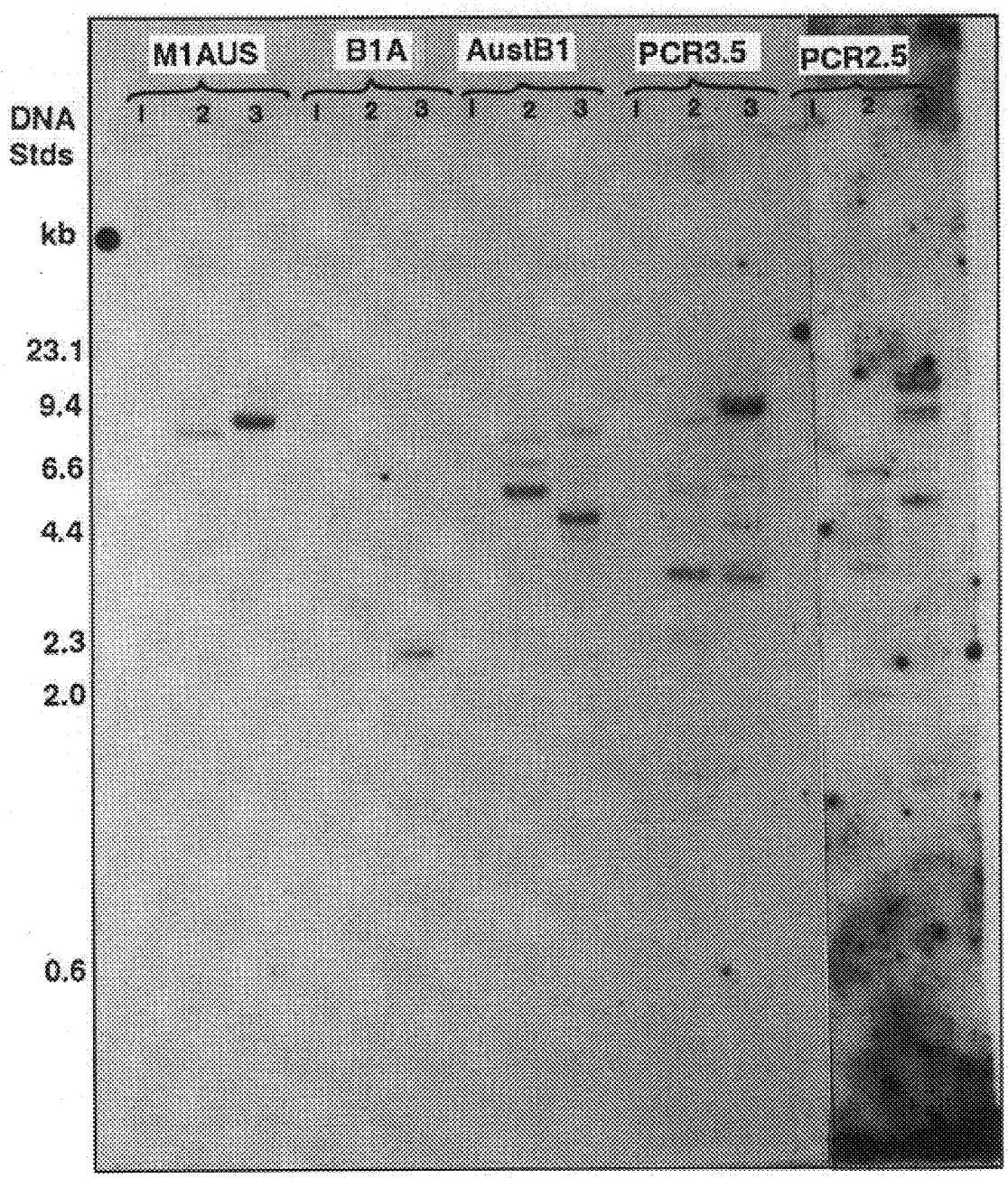
Figure 12:
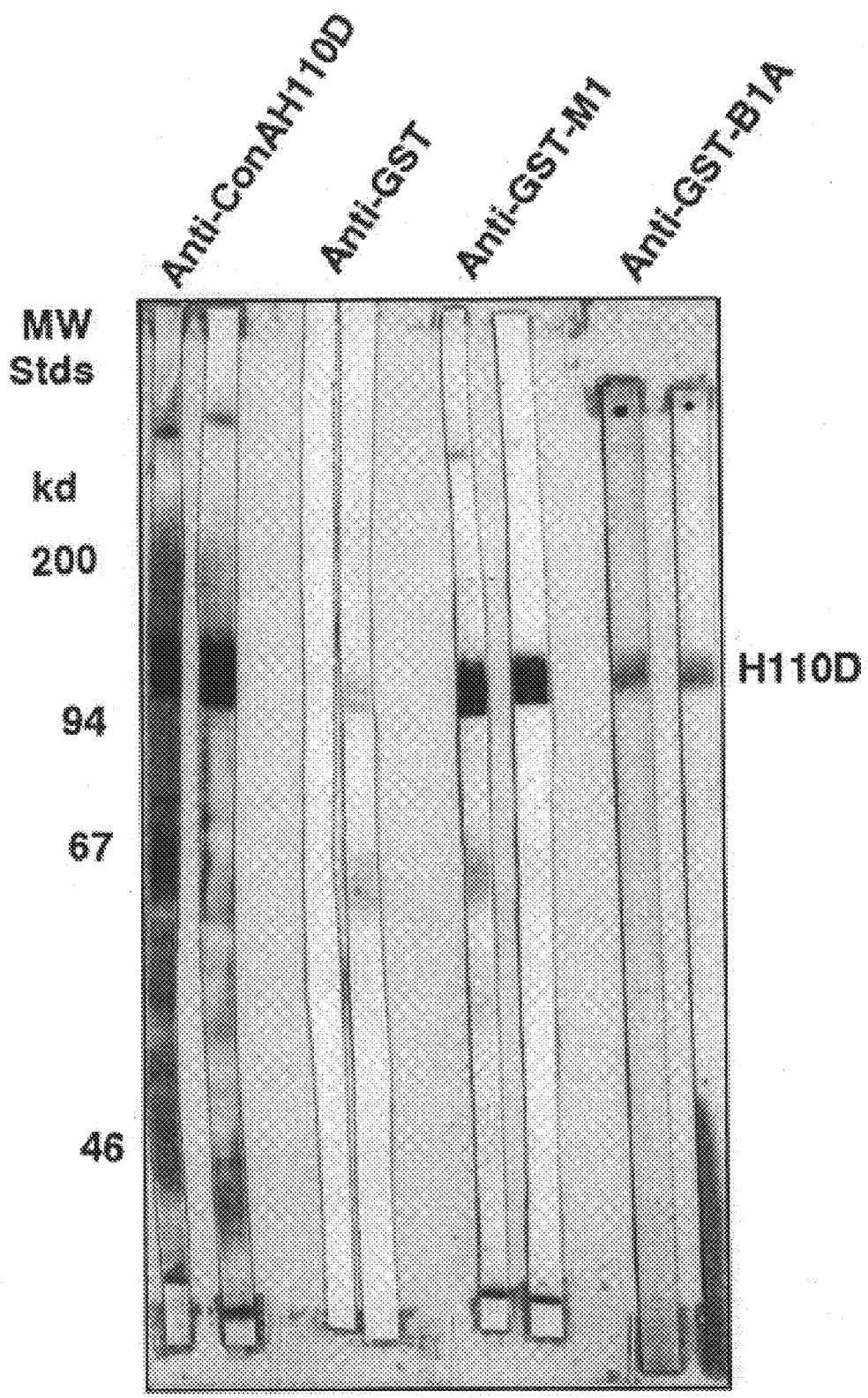
Figure 13A:
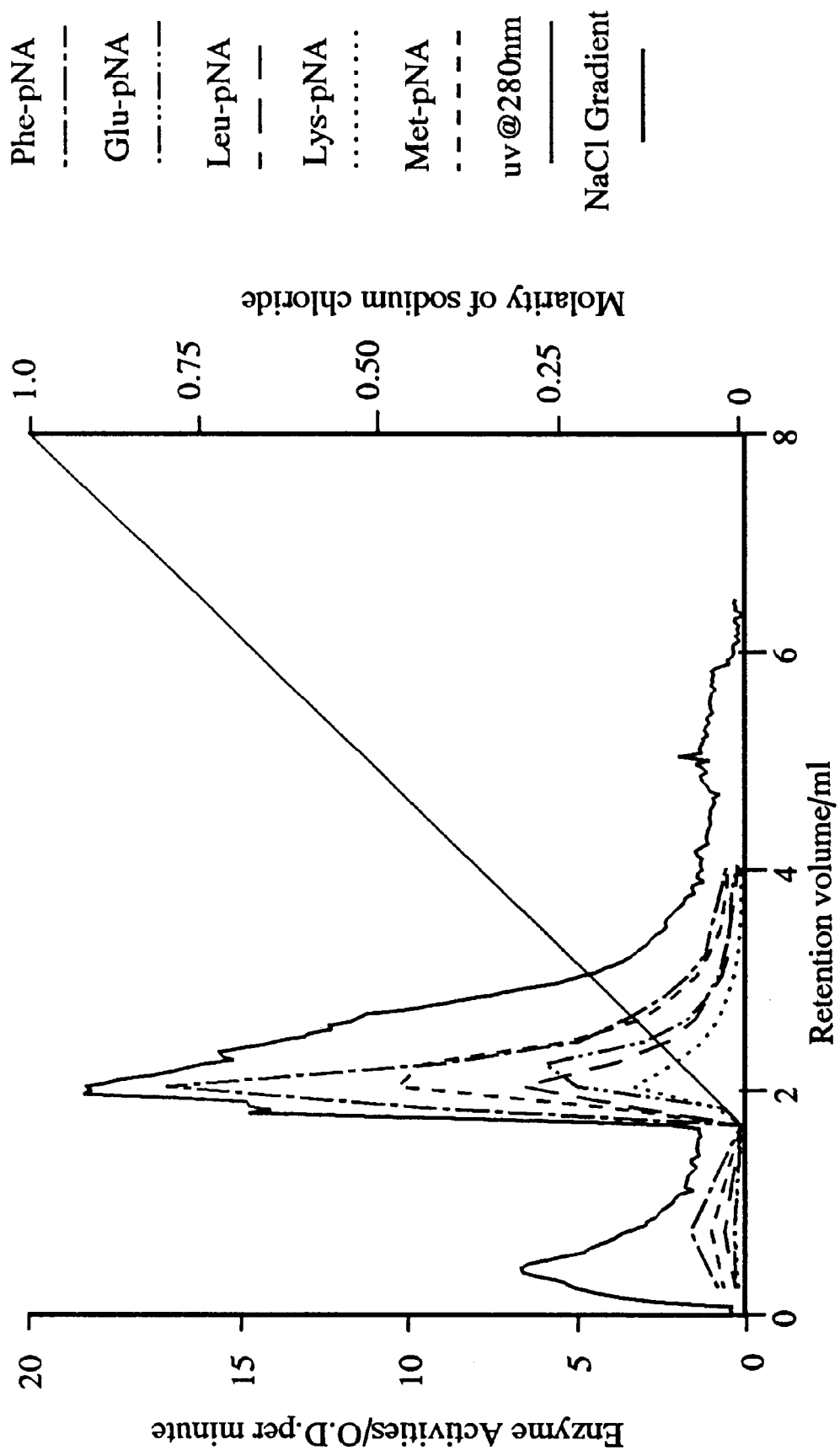
Figure 15A:
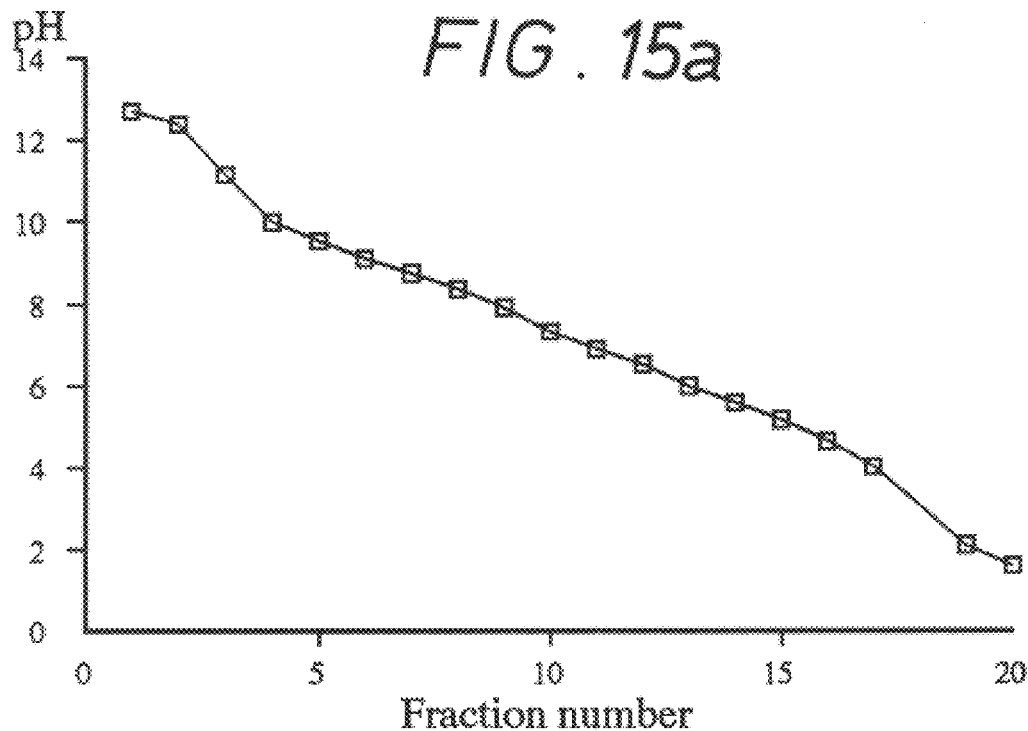
Figure 15B:
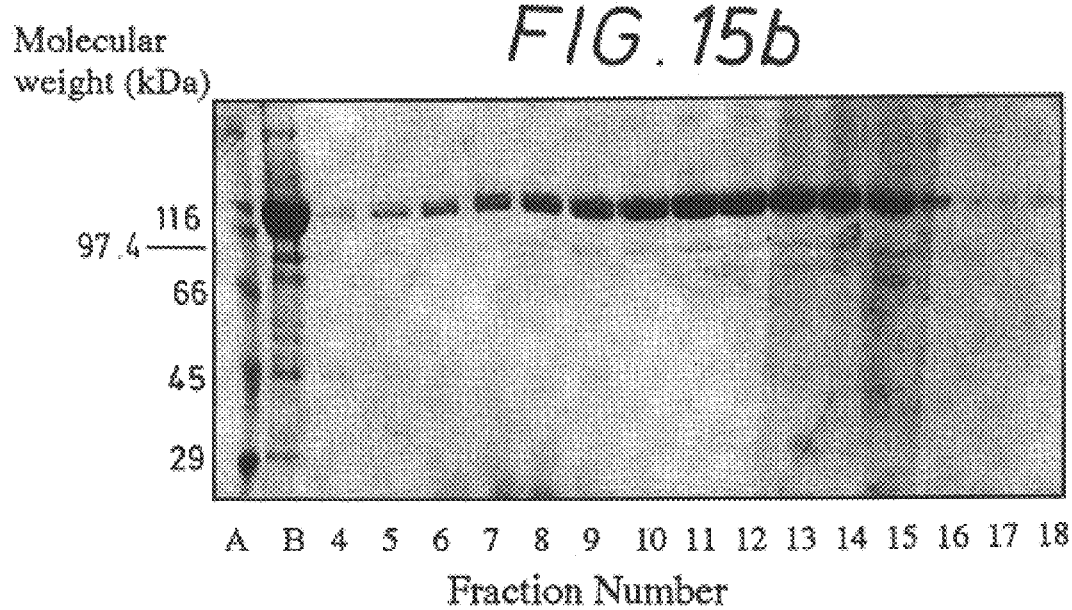
Figure 16A:
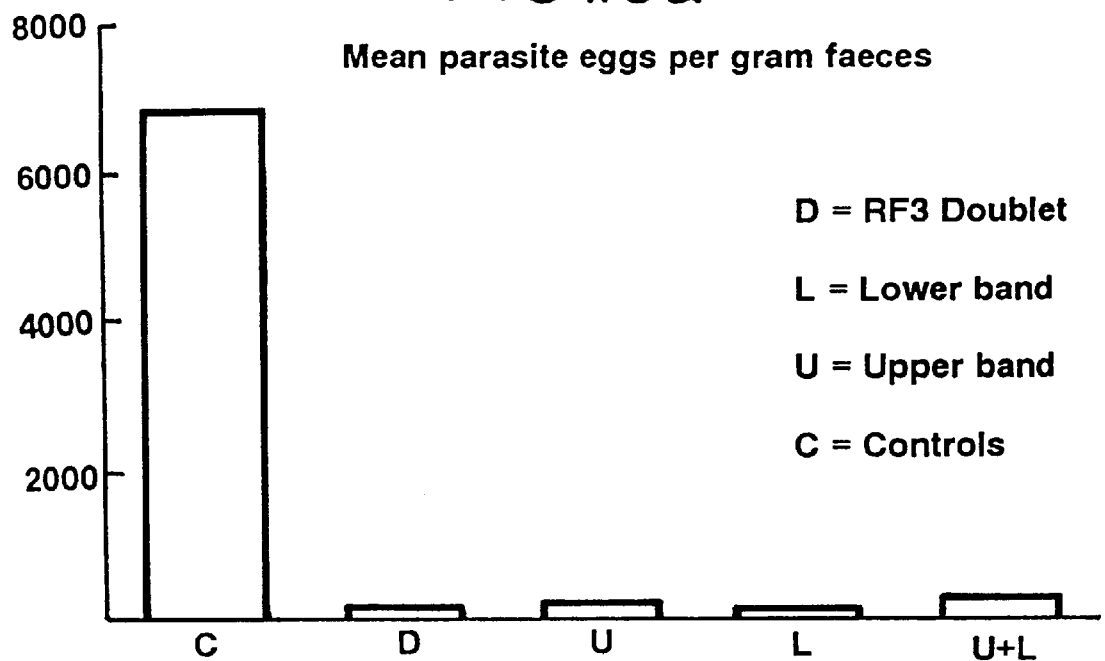
Figure 16B:
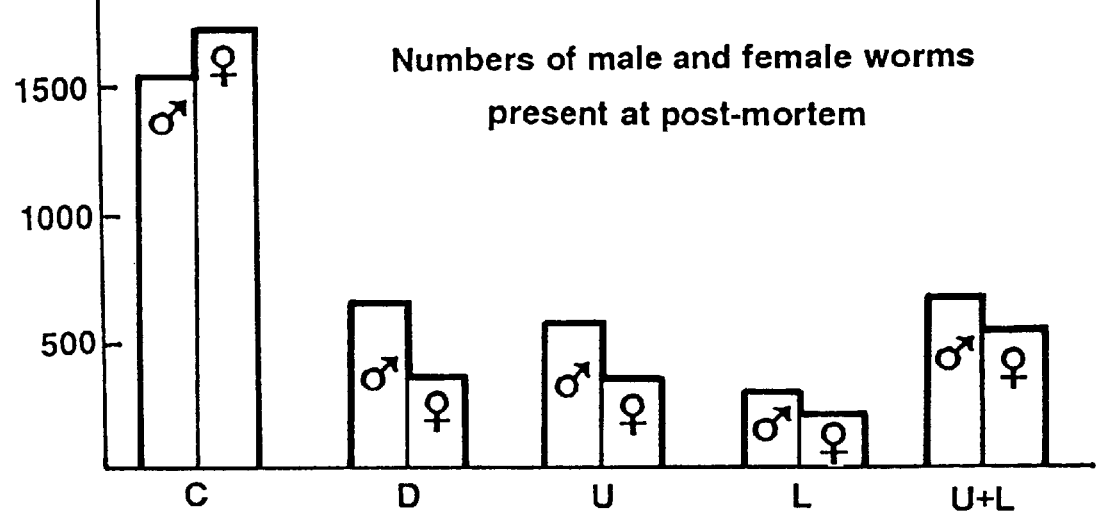
Figure 17A:
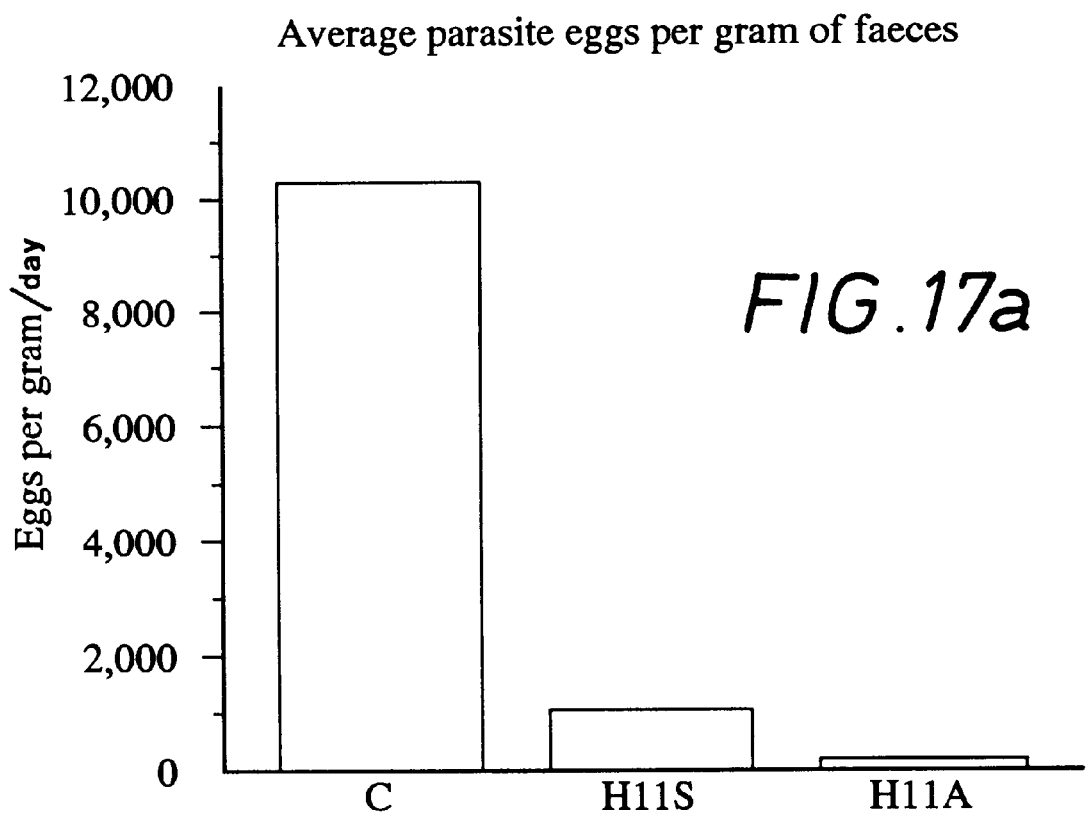
Figure 17B:
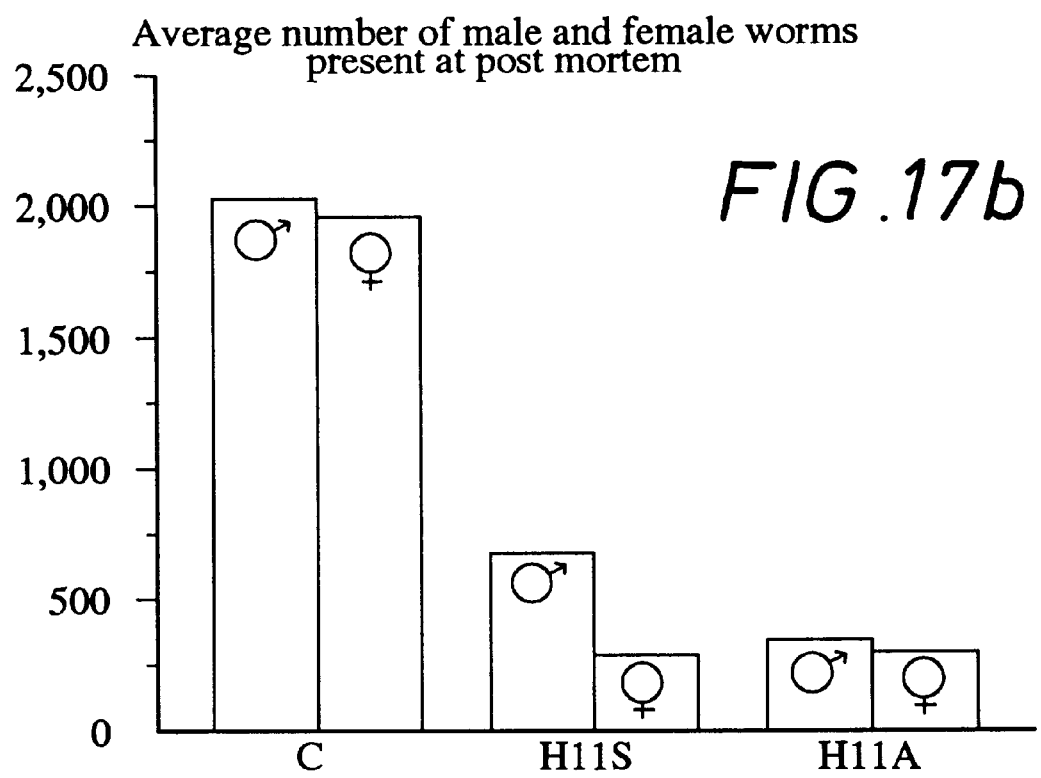
Figure 19A:
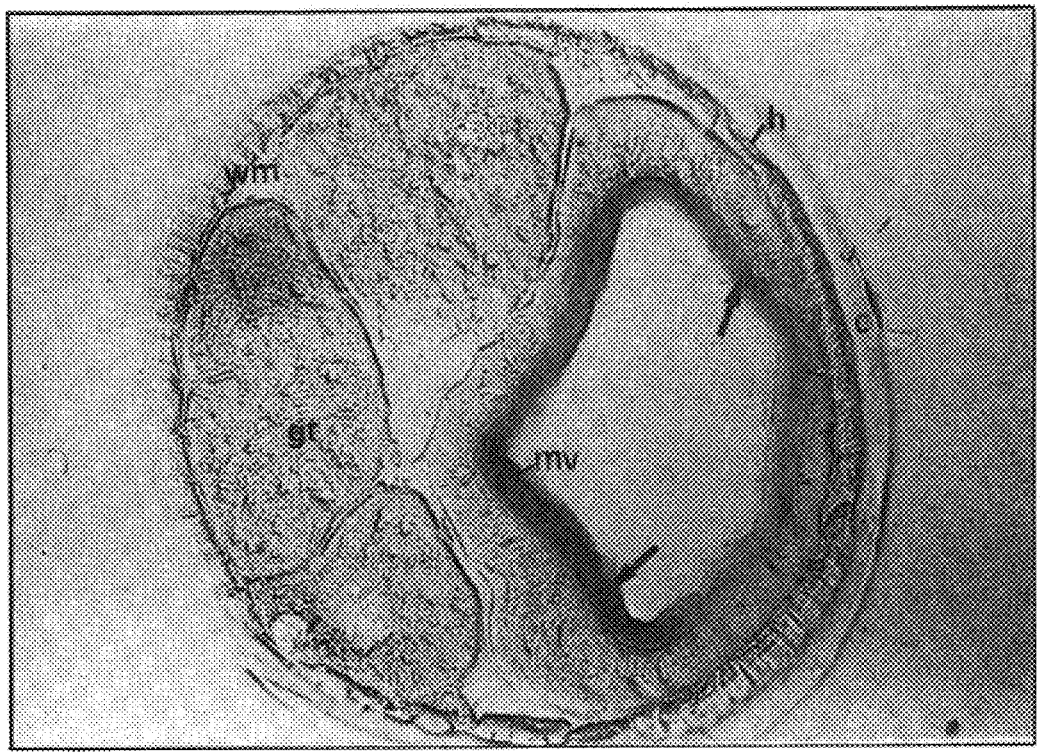
Figure 19B:
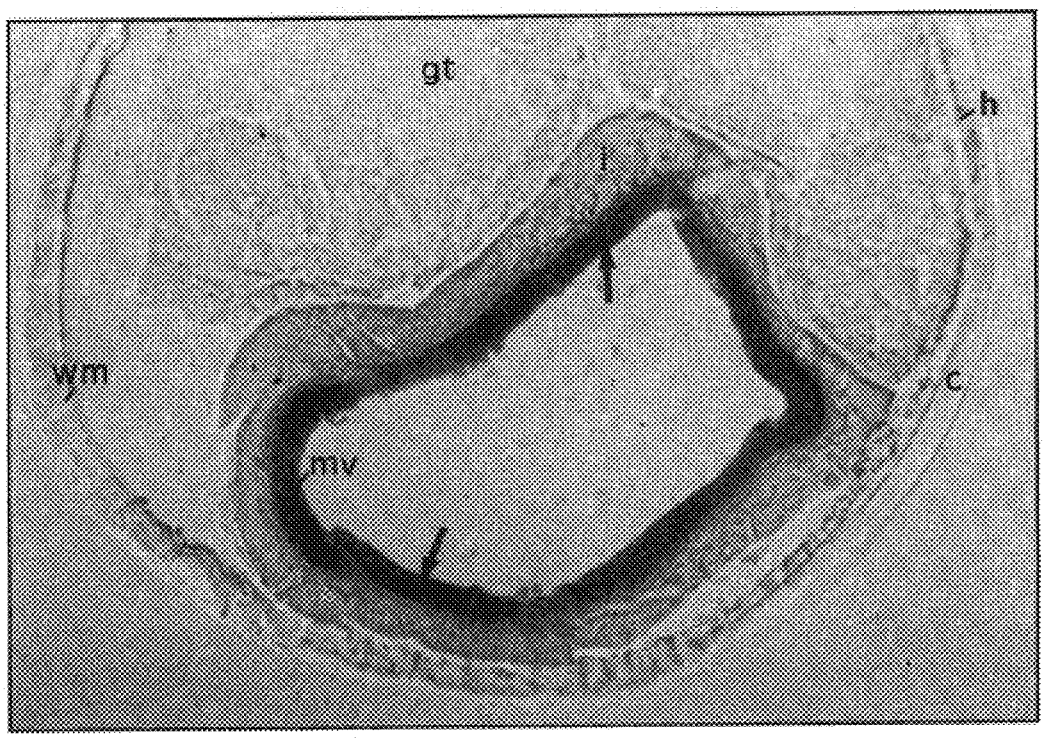
Figure 21:
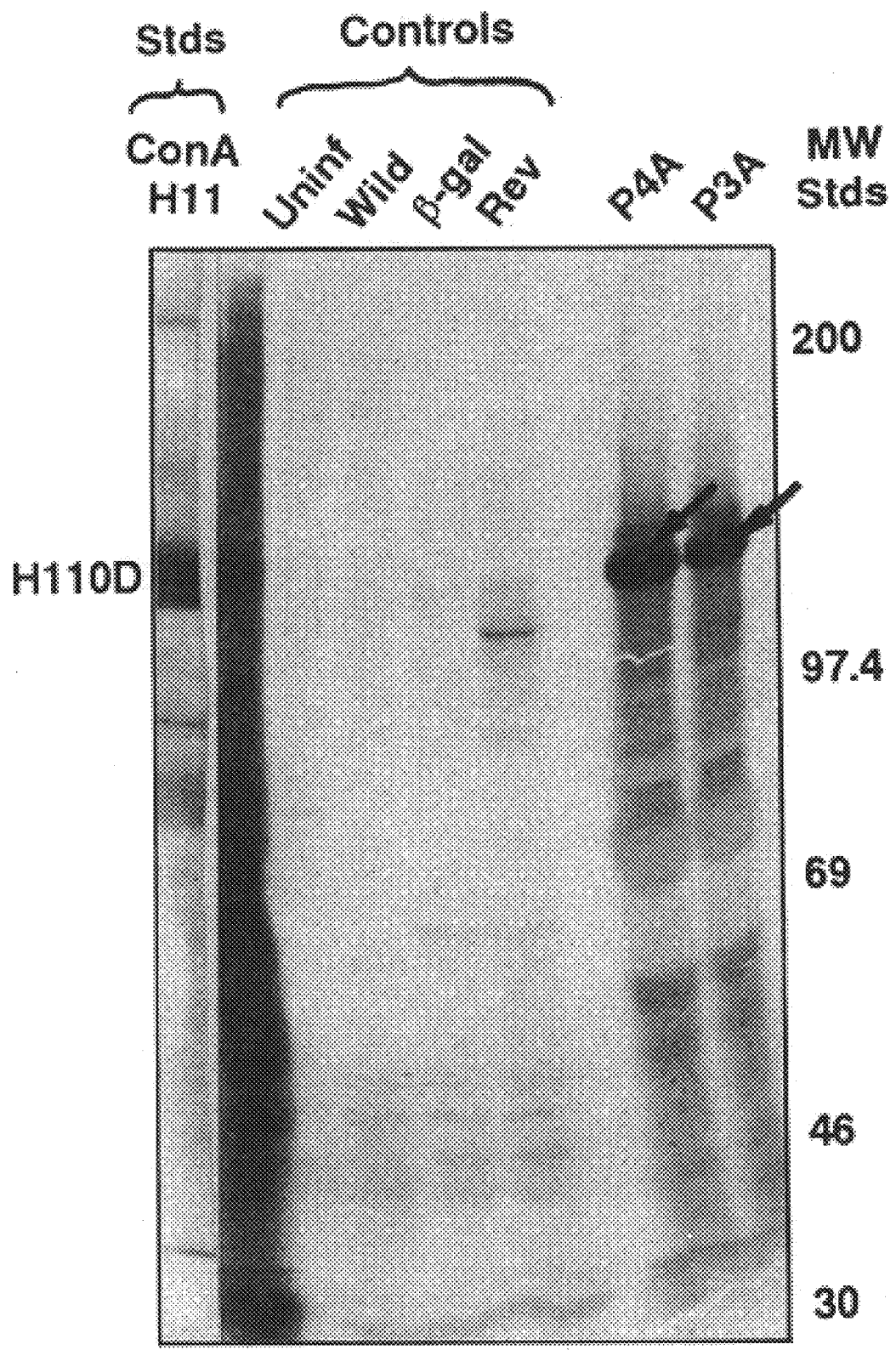

The following Example provides a description of the studies leading to determination of the sequences shown in FIGS. 1 to 7, with reference to the following additional Figures in which:

FIG. 8 shows Western blots of integral membrane proteins present in a detergent extract of *Haemonchus contortus* adults probed with affinity purified antibodies eluted from potential H110D clones; a) antigens in a detergent extract of Haemonchus recognised by antiserum to the extract; b) antibodies eluted from a strip such as that shown in a) re-tested against a blot of the detergent extract confirm the success of the elution step; c) antibodies as in b) which bind to clone M1 expressed protein strongly recognise a region at 110 kd (and a relatively sharp band at about 205 kd; d) there is no antibody binding when a non-recombinant is used to adsorb the serum;

FIG. 9 shows a Northern blot of mRNA purified from 11, 15 and 23 day-old *Haemonchus contortus* probed with a) cDNA clone M1 (SEQ ID NO:1); b) cDNA clone M1 AUS (SEQ ID NO:5); c) cDNA clone B1A (SEQ ID NOS:2 and 3); d) cDNA clone AustB1 (SEQ ID NO:6) ; e) cloned PCR product 014-872 (3.5-2, SEQ ID NO:8); and f) cloned PCR product 014-015 (SEQ ID NO:7). The numbers 11, 15 and 23 indicate the age of the Haemonchus from which the mRNA was obtained;

FIG. 10 shows Southern blots of *Haemonchus contortus* genomic DNA probed with cDNA clones M1AUS (SEQ ID NO:5), B1A (SEQ ID NOS:2 and 3) and AustB1 (SEQ ID NO:6) and PCR products 014-872 (3.5-2, SEQ ID NO:8) and 014-015 (SEQ ID NO:7); a) blots were washed at a moderate stringency, b) blots were washed at a high stringency; for each probe, track 1 contained a HindIII digest of λDNA as marker or was left blank, tracks 2 and 3 contained EcoRI and HindIII digests respectively of Haemonchus genomic DNA;

FIG. 11 shows Western blots of recombinant GST-M1 and GST-B1A fusion proteins probed with affinity purified antibodies to electrophoretically purified H110D (H110DE);

FIG. 12 shows Western blots of ConA H110D antigen probed with antisera to ConA H110D and to recombinant GST-M1 and GST-B1A fusion proteins;

FIG. 13 shows a) the results of analysis of H110D protein and aminopeptidase enzyme activities in fractions obtained by ion exchange chromatography of ConA H110D on a MonoQ column;

b) SDS-PAGE of the fractions shown in FIG. 13a);

FIG. 14 shows a) the pH values at which fractions were obtained in a free-flow isoelectric focussing experiment;

b) SDS-PAGE under reducing conditions of the fractions from 14a) in which the lower band of the H110D doublet is found in Fraction 6 and the upper band in Fraction 16, with varying amounts of each in the intervening fractions;

c) Western blots of the fractions shown in 14b) probed with i) monoclonal antibodies designated TS 3/19.7 and ii) affinity purified polyclonal anti-M1 antibodies; control antibodies gave no detectable reaction;

FIG. 15 shows a) the pH values at which fractions were obtained in another free-flow isoelectric focussing experiment; b) SDS-PAGE under reducing conditions of fractions from 15a) used in enzyme assays, in which the lower band of the H110D doublet is found in Fractions 4–6 and the upper band in Fractions 16–18 with varying amounts of each band in the intervening fractions; c) microsomal aminopeptidase specific activities of fractions shown in 15b);

FIG. 16 shows protection of sheep by vaccination with separated upper (U), lower (L), recombined U+L) and intermediate doublet (D) bands from H110D; a) parasite egg output, expressed as eggs per gram faeces, b) worm burden at post-mortem, relative to controls;

FIG. 17 shows protection of sheep by vaccination with a water-soluble fragment (H11S) obtained from H110D by digestion with elastase and H11A, the residual detergent-soluble H110D. a) parasite egg output, expressed as eggs per gram faeces; b) worm burden at post-mortem, relative to controls (C);

FIG. 18 shows examples of the relationship between inhibition of Ai, Bi) aminopeptidase M-like and Aii), Bii) aminopeptidase A-like activities of H110D by antisera of individual sheep vaccinated with H110D with levels of protection measured by Ai, ii) % reduction of worm burden at post-mortem and Bi, ii) % reduction reduction of faecal egg count; □ anti-H110D, ■anti-horse ferritin control;

FIG. 19 shows the histochemical localisation of aminopeptidase enzyme activities in adult *Haemonchus contortus*—the light micrographs of cryo-sections of adult female *Haemonchus contortus* show aminopeptidase activity (red reaction product appears as dark band (arrowed) in these black and white photographs) associated only with the microvilli (mv) of the intestine (i). None of the other tissues (eg. cuticle (c), hypodermis (h), genital tract (gt), wall muscle (wm)) show activity. In a) the substrate was L-leucine 4-methoxy-β-naphthylamide, in b) the substrate was L-glutamic acid α-(4-methoxy-β-naphthylamide);

FIG. 20 shows a map of the 3.5 PCR product (clone 2) (SEQ ID NO:8) sub-cloned into the baculovirus expression vector pBlueBacII®;

FIG. 21 shows a Western blot of extracts from baculovirus-infected insect *Spodoptera frugiperda* (Sf)9 cells probed with anti-H110DN antibodies. Two cloned plaques, P3A and P4A expressed the full-length immunopositive H110D (arrowed), the controls did not.

EXAMPLE

Methods

Construction of U.K. λGT 11 Library mRNA Isolation

Adult *Haemonchus contortus* (0.5 gm) of UK origin snap-frozen in liquid nitrogen were ground in liquid nitrogen using a pre-chilled mortar and pestle. The RNA was extracted from the grindate with 10 volumes of 4M guanidine hydrochloride in 25 mM sodium citrate containing 0.5% w/v sarkosyl and 0.7% w/v 2-mercaptoethanol, followed by extraction with phenol and chloroform using the method of Chomczynski & Sacchi (1987). Messenger RNA (mRNA) was prepared from this by affinity chromatography on oligo dT cellulose (twice) as described in Maniatis et al (1982) and the quality was assessed by in vitro translation using a rabbit reticulocyte lysate kit and $^{35}$S-methionine from Amersham International plc, according to the manufacturer's instructions. Polypeptides up to 120 kd were detected.

Complementary DNA Preparation

First strand complementary DNA (cDNA) was synthesized from 1 μg mRNA using random priming and avian reverse transcriptase and the second strand was synthesized using a replacement reaction with RNase H and *E. coli* DNA Polymerase I followed by repair of 3' overhangs using T4 DNA Polymerase, according to the method of Gubler & Hoffman (1983). The yield of double-stranded (ds) cDNA was approximately 400 ng from 1 μg mRNA. The ds cDNA was examined by electrophoresis in a 1% agarose gel followed by autoradiography. The ds cDNA was in the size range 0.2–9.4 kilobases (Kb), with the majority being in the range 0.5–2.3 Kb.

Cloning of cDNA in λgt11

Non-size selected cDNA was used to construct a library in λgt11 using the Amersham cDNA cloning system (kit no. RPN 1280, Amersham International plc) and in vitro packaging extracts (kit no. N334, Amersham International plc) as described in the manufacturer's instructions, and EcoRI linker oligonucleotides (5'GGAATTCC). The resulting library was plated on *E. coli* strain Y1090 in the presence of isopropylthio-β-D-galactoside (IPTG) and 5-bromo,4-chloro,3-indolyl β-D-galactoside (X-gal), under which conditions recombinant λgt11 appear as clear ("white") plaques and wild-type non-recombinant λgt11 as blue plaques. The library contained 90% white plaques and the cloning efficiency was calculated to be $4 \times 10^7$ plaque forming units (pfu)/μg cDNA and a library titre of $2 \times 10^6$ plaque forming units per ml. Analysis of the DNA from 20 recombinants picked at random revealed an average insert size of 0.51 kb. However this mean was distorted by one clone with an insert of 3.5 Kb. The majority of the inserts were >300 base pairs (bp). This unamplified λgt11 library derived from UK worm mRNA was then immunoscreened.

Preparation of Antibody Probes
Antiserum to Integral Membrane Proteins

Intestines were dissected from adult *Haemonchus contortus* (of UK origin) and homogenised in ice-cold phosphate buffered saline (PBS), pH 7.4, containing 1 mM ethylenediaminetetraacetic acid (EDTA) and 1 mM phenylmethylsulphonyl fluoride (PMSF). The homogenate was centrifuged for 10 minutes using a microfuge and the pellet resuspended in the same buffer containing 0.1% v/v Tween 20 (Tween is a Trade mark). After re-centrifugation, the pellet was resuspended in the same buffer containing 2% v/v Triton X-100 and extracted for two hours at 4° C. This extract was centrifuged as above, to obtain a supernatant consisting integral membrane proteins (IMP).

A sheep was hyperimmunised with IMP in Freund's Complete Adjuvant (FCA) by intramuscular injection of 50, 50, 120 and 130 μg of IMP given on weeks 0, 7, 11 and 15. Six weeks after the final injection, serum was harvested, and designated serum EE-068.

Preparation of Integral Membrane Proteins by Detergent Extraction of *Haemonchus contortus*

An extract was prepared by homogenizing worms in 5–10 volumes of PBS containing 1 mM EDTA and 1 mM PMSF. The suspension was centrifuged at 10,000×g for 20 minutes at 4° C. and the pellet washed in the same buffer containing 0.1% v/v Tween 20 then extracted with 5 volumes 2% v/v Triton X-100 as described above. The supernatant was re-centrifuged at 100,000×g for 1 hour, and the resulting supernatant, which was enriched in H110D but contained other IMP, was used in Western blotting experiments and for the preparation of non-denatured H110D (see below).

Preparation of H110D and Affinity Purified Anti-H110DN

The extract enriched for H110D, was subjected to affinity chromatography on ConA-agarose followed by ion exchange chromatography on MonoQ (as described in WO 88/00835 and WO 90/11086). The purified H110D was injected intramuscularly into lambs in FCA. Three doses of 100 μg were given at 3 week intervals. Serum collected from the lambs 4 weeks after the final injection was affinity purified by absorption to a column containing purified H110D which had been coupled to cyanogen bromide activated Sepharose (Pharmacia). Coupling to H110D to the Sepharose, binding of antiserum and elution of anti-H110D antibodies were according to the instructions supplied by Pharmacia. These affinity purified antibodies are designated anti=H110DN. The "N" distinguishes these antibodies from those raised to denatured, electrophoretically purified H110D, which are designated anti-H110DE.

Western Blotting

Western blotting was carried out using standard procedures (Johnstone et al., 1982).

Isolation and Characterisation of Clones
Immunoscreening of the U.K. λgt11 Library The method used to immunoscreen the library was essentially as described by Bowtell et al (1986). Prior to use, the serum (EE-068) was depleted of anti-*E. coli* antibodies by absorption with lysates and whole cells of *E. coli* Y1090. The library was plated on *E. coli* Y1090 cells at a density of $10^3$ pfu per 90 mm diameter plate. Plates were overlaid with nitrocellulose filters impregnated with IPTG and incubated overnight. The filters were washed with TBST (50 mM Tris, pH 7.4, 150 mM, NaCl, 0.05% v/v Tween 20) and then blocked with 5% v/v horse serum in TBST for 2 hours. Serum EE-068 diluted 1 in 200 in TBST containing 5% horse serum was added and the filters incubated for 4 hours with gentle rocking. The filters were again washed in TBST, then incubated with horseradish peroxidase (HRP)-conjugated horse anti-sheep IgG diluted 1 in 500 in TBST containing 5% v/v horse serum for 2 hours. (Anti-serum to sheep IgG was raised in a horse, the anti-sheep IgG purified by affinity chromatography on a sheep IgG Sepharose column, and the antibodies conjugated to HRP by the method of Nakane & Kawaoi, 1974.) Filters were further washed in TBST and positive plaques detected using 0.6 mg/ml 3,3'-diaminobenzidine (DAB) and 0.1% v/v hydrogen peroxide. Twenty-five putative positives were picked and were rescreened with affinity purified anti-H110DN as described above. Following this secondary screen 5 recombinants were still positive with the clone designated as M1 giving the strongest signal.

Affinity Purification of Antibody on Recombinant Phage

Confluent plates were prepared on *E. coli* Y1090 lawns by plating $10^3$ pfu of each of the antibody-positive λclones or non-recombinant λgt11 negative control phage. The lawns were incubated for 4 hours at 42° C. then overlaid with filters impregnated with IPTG and further incubated overnight at 37° C. The filters were removed form the plates and washed in TBST prior to being blocked with 5% v/v horse serum for 1 hour. The filters were then incubated with a 1 in 100 dilute of antiserum EE-068 for 6 hours, before being thoroughly rinsed with TBST. Bound antibodies were eluted from the filters by two applications of 2 ml of elution buffer (5 mM glycine, 500 mM NaCl, 0.2% Tween 20, pH 2.3) for 2 to 3 minutes each, neutralised by addition of 200 μl of 1M tris-HCl, pH 7.4, diluted 1 in 200 and used to immunoscreen a Western blot of an H110D-enriched extract.

DNA Sequencing of the M1 Clone

Lambda DNA was isolated from the M1 cone according to the methods described in Maniatis et al (1982). The 2.38 Kb KpnI-SstI fragment containing the 300 bp M1 fragment was isolated by gel electrophoresis, purified using a GENECLEAN kit (Stratagene) (GENECLEAN is a registered trade mark of BIO101) and subcloned into pBluescriptII SK⁺ (Stratagene). The EcoRI fragment was purified using the same methods and re-subcloned into the same vector.

The nucleotide sequence of the M1 insert was determined using a T7 Sequencing kit (Pharmacia, U.K.), using both the M13 forward and reverse primers.

Preparation of Australian λGT11 and λZAP cDNA Libraries mRNA Isolation 5 gm adult *Haemonchus contortus* (Australian McMaster susceptible strain) snap-frozen in liquid nitrogen were ground in liquid nitrogen and the RNA extracted using hot phenol by the method of Cordingley et al. (1983). Yield of total RNA was 10.35 mg. 1.3 mg of this RNA was used to prepare mRNA by affinity chromatography on oligo dT cellulose (2 sequential purifications) using the method described by Maniatis et al. (1982). Yield of mRNA was 21.6 µg. Quality of mRNA was assessed by in vitro translation in rabbit reticulocyte lysate in the presence of $^{35}$S-methionine (Amersham) according to the supplier's instructions. The translation products obtained had clearly distinguished bands including bands >200 kd in size as demonstrated by electrophoresis on SDS-polyacrylamide gels followed by fluorography.

cDNA Synthesis and Library Preparation

1 µg mRNA was used to make cDNA by priming with oligo dT or random primers, using a cDNA synthesis kit from Amersham International plc following the manufacturer's instructions. Yield was 115 ng double stranded (ds) cDNA. The quality of the cDNA was examined by electrophoresis of the $^{32}$p-labelled DNA on an alkaline agarose gel as described by the Amersham cDNA kit instructions. Size of the cDNA (by comparison with λ-HindIII markers, New England Biolabs) was from 150 bp to >10 Kb, with most of the products being in the size range 0.6–5 Kb. The oligo dT-primed and random-primed ds cDNAs were pooled and ligated to excess EcoRI 8-mer linkers (5'GGAATTCC3' (SEQ ID NO:55) New England Biolabs, Catalogue No. 1018) which had been labelled with λ-$^{32}$P-ATP and T4 polynucleotide kinase. The linkered cDNA was digested with EcoRI and excess linkers were removed by Sepharose 4B (Pharmacia) chromatography according to the methods described by Maniatis et al. (1982). Fractions from the column were pooled in two lots, one containing cDNA larger than 2Kb and one of cDNA less than 2 Kb. Each pool was then ligated separately to 1 µg EcoRI cut, phosphatased λZapII arms (Stratagene) and packaged separately using Gigapack Gold (Stratagene, registered trademark). The larger sized cDNA yielded 1.3×10⁵ recombinants and the smaller cDNA 1.4×10⁵ recombinants; there were pooled to yield a library of 2.7×10⁵. The λZap library was amplified by plating an XL1-Blue cells (Stratagene) at 2×10⁴ pfu per 135 mm plate. The titre of the amplified library was 7×10⁷ pfu/ml.

A further 2 µg mRNA was used to make cDNA as described above, but using only oligo dT as primer. The yield of ds cDNA was 740 ng. This cDNA was treated with EcoRI methylase as described in Maniatis et al (1982) prior to addition of EcoRI linkers, and in this case 12-mer linkers (5'CCGGAATTCCGG3' (SEQ ID NO:56) New England Biolabs, Catalogue No. 1019) were used. Following digestion of the linkered cDNA with EcoRI, all fractions from a Sepharose 4B column which contained cDNA were pooled, and ligated to 2 µg EcoRI cut, phosphatased λgt11 arms (Stratagene). The ligation mix was split in two and packaged with two lots of Gigapack Gold (Stratagene); these were pooled to yield a λgt11 library of 7×10⁶ pfu. The library was amplified by plating on ST9 cells at 5×10⁵ pfu per 135 mm plate. The titre of the amplified λgt11 library was 4.5×10¹¹ pfu/ml.

Screening of the Australian λgt11 Library with Antisera to H110D

Antisera was raised by injecting sheep with H110D protein (of UK origin) which had been electro-eluted from polyacrylamide after electrophoresis in SDS according to the following method: ConA H110D prepared as described in WO 88/00835 and WO 90/11086 was electrophoresed on SDS polyacrylamide gels (Laemmli 1970) to obtain electroeluted H110D. After electrophoresis, the area of the polyacrylamide gel containing H110D was cut out, place din an electroelute (Atto) and elution carried out for 3 hours at 10 watts. The electroeluted H110D (designated H110DE) was concentrated on a Centriprep 10 (Amicon) and buffer exchanged on a PD10 column (Pharmacia) into 50 mM ammonium bicarbonate/0.07% SDS, mixed with adjuvants and then injected into sheep. Immunoglobulins from the sera were precipitated with ammonium sulphate (Johnstone and Thorpe, 1982). The precipitated antibodies were resuspended at 60 mg/ml in phosphate buffered saline, dialysed against phosphate buffered saline and diluted 1:10 in Tris buffered saline (TBS) containing 5% w/v low fat milk powder. 10 mg of ConA H110D was made to 0.5% SDS, heated to 100° C. for 3 minutes and dried onto a nitrocellulose filter. Following washes with TBS containing 0.2% v/v Tween 20 and 0.5% Triton X-100 (TBSTT) the filter was incubated for 1 to 2 hours at room temperature with the antibodies to H110DE. After washing the filter for 2 hours with TBSTT, the bound antibodies were eluted with 3 ml of 0.1M glycine, 0.15M NaCl pH 2.6 for 2 minutes and immediately adjusted to neutral pH by the addition of 75 µl of 1.5M Tris pH 8.0. These affinity purified antibodies, designated anti-H110DE, were used to screen 5×10⁵ pfu of the Australian λgt11 cDNA library as described above.

5×10⁵ recombinants from the λgt11 library derived from Australian *Haemonchus contortus* were immunoscreened and three positives picked. Following further screening two of these recombinants were still positive and were designated B1A and B2.

Sequencing of B1A and B2 Clones

The two clones were digested with EcoRI, yielding a single insert of approximately 500 bp for B1A and three fragments, B2A (about 400 bp), B2B (about 100 bp) and B2C (about 100 bp), for B2. These were subcloned into pBluescript SK⁺ (Stratagene) and sequenced using a Sequenase 2.0 kit (United States Biochemicals).

Expression of Clones M1 and B1A

The M1 (SEQ ID NO:1) and B1A (SEQ ID NOS:2 and 3) inserts were expressed in *E. coli*, using pGEX vector (Smith and Johnson 1988). This vector expresses proteins at the C-terminus of *Schistosoma japonicum* glutathione-S-transferase ()GST). The M1 and B1A EcoRI inserts were ligated to EcoRI-cut, phosphatased pGEX1 and transformed into *E. coli* strain JM101 according to the methods described in Maniatis et al. 1982. Eight progeny were picked from each transformation and 2 ml cultures were grown for 6 hours at 37° C. IPTG was added to induce fusion protein synthesis, and the incubation continued overnight. Cells were harvested by centrifugation, disrupted by boiling in sample buffer (Laemmli, 1974), and the extracts analysed by SDS-PAGE and by Western blotting using affinity purified sheep antibodies specific for the SDS-denatured H110D doublet (anti-H110DE—see above). Bound antibodies were detected using alkaline-phosphatase conjugated rabbit anti-sheep IgG alkaline phosphatase conjugate (Jackson Immunoresearch) followed by colour development with 5-bromo,4-chloro,3-indolyl phosphate (BCIP) and nitroblue tetrazolium (NBT). Cultures of immunopositive clones were grown and induced as above and disrupted by sonication. The sonicates were separated into soluble and insoluble fractions by centrifugation (Sorvall RC-2B centrifuge, HS4 rotor, 7000 rpm, 30 minutes, 4° C.). The insoluble pellets were resuspended in 8M urea by sonication, and samples of fractions examined by SDS-PAGE. The fusion proteins were found to be in the insoluble inclusion body fraction. Each of these preparations was used to vaccinate 2 sheep three times at 150 μg fusion protein per dose in Freunds adjuvants. Positive control sheep were immunised with native ConA H110D protein, and negative control sheep were immunised with solubilised protein from *E. coli* containing the pGEX vector without an Haemonchus insert. Sera from vaccinated sheep were analysed by Western blotting against H110D.

Screening of the Australian λZAP Library by DNA Hybridisation with M1 and B1A Inserts M1 and B1A plasmid DNAs (cloned in pBluescript) were digested with EcoRI and the inserts isolated by electrophoresis in TBE (tris-borate-EDT; 89 mM tris-=borate, 89 mM boric acid, 2 mM EDTA pH approximately 8.3) buffer in 1% agarose gel, followed by purification using a GENECLEAN hit. The isolation and purification were repeated to avoid contamination of the probe with plasmid DNA sequences which would hybridise to λZAP sequences, causing unacceptable levels of background. The purified insert DNAs were labelled with α-$^{32}$P-dCTP using a Nick Translation kit from Promega Biotech according to the manufacturer's instructions. Labelled DNA was separated from unincorporated label by spin column chromatography (Maniatis et al., 1982). Eight 135 mm plates of the λZAP library were plated at 10$^5$ pfu/plate, and plaque lifts performed onto nitrocellulose filters (Maniatis et al., 1982). Following baking in a vacuum oven for two hours at 80° C., filters were prehybridised for two hours at 42° C. overnight (as described below in the Southern Blot analysis section). Four filters were screen with the M1 probe and four with the B1A probe. Filters were washed twice in 2× SSC containing 0.5% SDS, once in 1× SSC containing 0.5% SDS and once in 0.5× SSC containing 0.5% SDS, all at 50° C., and autoradiographed. Potential positive plaques were picked, and re-screened with the probes. High titre phage stocks were prepared from confirmed positives (designated M1AUS for the M1-hybridising clone and AustB1 for the B1A-hybridising clone) and the clones rescued into pBLUESCRIPT according to the λZAP manufacturer's instruction manual (Stratagene), using BB4 as the host *E. coli* strain. Plasmid DNA minipreps of the resultant progeny were prepared by alkaline lysis (Maniatis et al., 1982) and digested with EcoRI. Digests were analysed by agarose gel electrophoresis.

Sequencing of the M1AUS Insert

DNA sequencing was carried out in purified pBLUESCRIPT plasmid DNA using the United States Biochemicals version 2.0 Sequenase kit, according to the manufacturer's instructions. For the first sequencing reactions primers from the ends of the vector sequence were used to prime the reactions. The sequencing data obtained from these reactions was used to design a second pair of primers and from the data generated with these second primers a third pair were designed. In this way the DNA was sequenced by 'walking' from both the 5' and 3' ends.

Sequencing of the AustB1 Insert

This was carried out using Sequenase 2.0 T7 polymerase (USB Biochemicals) as described for the sequencing of the M1AUS insert.

Polymerase Chain Reactions

Preparation of cDNA mRNA (1 μg) from 11 day old post-infection U.K. *H. contortus*, prepared as described for adult UK worms, was mixed with T17 adaptor-primer (5'GACTCGAGTCGACATCGATTTTTTTTTTTTTTTT 3' (SEQ ID NO:57)) in diethyl pyrocarbonate (DEPC)-treated water, then heated to 65° C. for 5 minutes and immediately placed on ice. Methylmercury hydroxide was added to a final concentration of 28.6 mM and the mixture incubated at room temperature for 3 minutes. 2-mercaptoethanol was added to a final concentration of 14.2 mM and the mixture was placed on ice. To synthesize cDNA, RNAse Guard (Pharmacia) was added to 1 unit/μl, Reverse Transcriptase buffer (Life Sciences) to 1 times concentration, dATP, dGTP, dCTP and dTTP each to 1 mM, and AMV Reverse Transcriptase (Life Sciences) to 2 units/μl (all given as final concentrations). The reaction was incubated at 41° C. for 75 minutes, then extracted with phenol and chloroform and purified by spun column chromatography (Maniatis et al, 1982). The purified reaction mix was diluted 2.5-fold and stored at 4° C.

PCR Amplification of the cDNA Using M1AUS-Specific Primers

PCR reactions were carried out using a Programmable Thermal Cycler (M.J. Research Inc.). The reaction mix contained 1 μl out of the 250 μl diluted cDNA prepared as described above, 25 pmol of the first strand T17-adaptor-primer, 25 pmol of second strand amplification primer (either that based on positions 865–884 (5'ACGGGTGTTCGGTTCCGTAT 3' (SEQ ID NO:58)) or that based on positions 30–49 (5'GCTGAATCTAACTCCAATCC 3' (SEQ ID NO:59)) of the M1AUS sequence (SEQ ID NO:5)), 1× Taq buffer (Northumbria Biologicals Ltd) and 0.5 mM each of dATP, dTTP, dGTP and dCTP, in a 100 μl reaction volume and covered with 40 μl mineral oil to prevent evaporation. This mix was then heated in the thermal cycler to 95° C. for 2 minutes then held at 72° C. Whilst at 72° C. 2 units for Taq Polymerase (Northumbria Biologicals Ltd) was added and mixed gently with the other reactants. The following program was then carried out in the thermal cycler:

Step 1 Anneal at 50° C. for 5 minutes
Step 2 Extend at 72° C. for 40 minutes
Step 3 Denature at 94° C. for 40 seconds
Step 4 Anneal at 50° C. for 2 minutes
Step 5 Extend at 72° C. for 3 minutes
Step 6 29 cycles of steps 3 to 5
Step 7 Final extension at 72° C. for 15 minutes
Step 8 Hold at 4° C.

These conditions were established from Frohman et al., (1988).

Cloning of the PCR Products

The PCR products from the above reactions were separated by electrophoresis in an agarose gel. Bands of DNA of approximately 2.5 and 3.5 kb were electroeluted onto glass fibre (Whatman), phenol extracted and purified by G50 chromatography (Pharmacia) (Sambrook et al., 1989). The purified DNA was ligated into pT7Blue T-vector (Novagene) following the manufacturer's instructions.

Sequencing of the 2.5 kb and 3.5 kb PCR Products

DNA sequencing was carried out with a Sequenase 2.0 kit (US Biochemicals) using the "oligonucleotide walking" technique described in the section on sequencing of M1AUS.

Polymerase Chain Reactions for the 5' Ends
Preparation of First Strand cDNA

1 μg of mRNA from 11 day post-infection UK *Haemonchus contortus* prepared as described for adult worms was mixed with a constant primer (5'AAIGAAAGCGGATGGCTTGAIGC 3' (SEQ ID NO:60)) designed from a conserved region in AustB1 and the 2.5 kb PCR and 3.5 kb PCR products (SEQ ID NOS:6, 7 and 8 respectively). The mixture was heated to 65° C. for 5 min., placed on ice and methyl mercury hydroxide added to a final concentration of 28.6 mM. The mixture was incubated at room temperature for 5 min., then 2-mercaptoethanol added to a final concentration of 14.2 mM and the mixture placed on ice. First strand DNA was prepared using reagents from the 5' RACE system (Gibco/BRL) at a final concentration of 20 mM Tris/HCl pH 9.4, 50 mM KCl, 2.5 mM MgCl$_2$, 100 μg/ml BSA, 0.5 mM of dATP, dCTP, dGTP, dTTP. 200 Units of Superscript Reverse Transcriptase were added and the reaction was incubated at 42° C. for 30 min. and then heated at 55° C. for 5 min. RNase H was added to a final concentration of 100 Unit/ml and the reaction incubated at 55° C. for 10 min. and then placed on ice. The cDNA was purified through a Glassmax spin column (Gibco/BRL) and stored at −20° C.

C-Tailing of the cDNA

⅕ of the first strand cDNA was heated at 70° C. for 5 min then chilled on ice for 1 min. Reagents from the 5'RACE system (Gibco/BRL) were added to a final concentration of 10 mM Tris/HCl pH 8.4, 25 mM KCl, 1.25 mM MgCl, 50 ug/ml BSA, 0.2 mM dCTP. 500 Units/ml Terminal transferase were added and the reaction incubated at 37° C. for 10 min, then heated at 70° C. for 15 min and stored on ice.

PCR Amplifications Using AustB1, 2.5 kb PCR and 3.5 kb PCR Specific Primers

The PCR reactions were carried out in a programmable Thermal Cycler (M.J. Research Inc.). For the 3' end one of 3 primers was used.

1. A primer specific for the 2.5 kb PCR product based on positions 374 to 394 (5'TGTTGTGGCTAATTTCGTCCA 3' (SEQ ID NO:61 and 62)).
2. A primer specific to the 3.5 kb product based on positions 1210 to 1229 (5' CATCTTIAGTTATCTGACCAG 3').
3. A primer specific for the cDNA clone AustB1 based on positions 357 to 377 (5' GACCATCGCTGATGAAGTCGG 3' (SEQ ID NO:63)).

For the 5' end of the reactions a common 'Anchor primer' (5'CUACUACUACUAGGCCACGCGTCGACTAGT ACGGGIIGGGIIGGGIIG3' (SEQ ID NO:64)) was used. Each reaction mixture contained 4 μl of the 50 μl of C-tailed cDNA, 25 pMol of the appropriate 2 primers, 1× Taq polymerase buffer (Boehringer/Mannheim) and 0.5 mM each of dATP, dCTP, dGTP and dTTP to a final volume of 100 μl. This mix was covered with 50 μl of mineral oil and heated to 95° C. in in the cycler for 2 min. The reaction mix was held at 80° C. whilst 0.6 units of Taq Polymerase were added and then put through the following programme:

1. Anneal at 50° C. for 5 min.
2. Extend at 72° C. for 10 min.
3. Denature at 94° C. for 45 sec.
4. Anneal at 50° C. for 1 min.
5. Extend at 72° C. for 2.5 min.
6. 39 cycles of 3 to 5.
7. Extend at 72° C. for 15 min.
8. Hold at 4° C.

Cloning of the 5' PCR Products

The PCR products were separated by electrophoresis on an agarose gel and bands of the expected size, circa 1.3 kb, were cut out, the DNA purified using a GENECLEAN kit and ligated into PT7Blue T-Vector (Novagene) according to the manufacturer's instructions.

Polymerase Chain Reaction for the Production of the 3' End of AUSTB1

The first strand cDNA used was that described for the production of cDNA for use with M1AUS primers. A specific primer from 1414 to 1435 (5'TCTTGAAGAAATGAAAAAGCTT 3' (SEQ ID NO:65)) in AustB1 (SEQ ID NO:6) was used with the T17 Adaptor primer used for the M1AUS PCR and the reactions carried out in a thermal cycler (M.J. Research Inc). The reaction mixture consisted of 25 pMol of each primer, 2 μl of cDNA, 1× Taq Polymerase buffer (Boehringer Mannheim), 0.5 mM dATP, dCTP, dGTP and dTTP in 100 μl. These were covered with 50 μl mineral oil and heated to 95° C. for 2 min. 0.6 μl of Taq polymerase was added and the same programme cycle carried out as for the 5' PCR described above.

Cloning and Sequencing of the 3' Products

The products of the PCR were separated by electrophoresis in an agarose gel and a band of the expected size, 1.3 kb, cut out and the DNA purified using a GENECLEAN kit and ligated into PCR-Script (Stratagene) according to the manufacturer's instructions.

Sequencing of the Cloned PCR Products

The DNA from the PCR clones was sequenced using a Sequenase 2.0 kit (United States Biochemical) as instructed by the manufacturer. Oligonucleotide primers were used to "walk along" the DNA of the clones from both the 5' and 3' ends.

Analysis of All DNA Sequences

Sequences were analysed using the GCG (Genetics Computer Group) Sequence Analysis Software Package, Devereux et al., 1984.

Northern and Southern Blot Analyses
Preparation of Northern Blots

Northern blots were performed in formaldehyde gels essentially as described in Maniatis et al. (1982). mRNA samples (from 11-, 15- and 23-day old adult *H. contortus*) were treated with 17.5% v/v formaldehyde and 50% v/v formamide in MOPS buffer (20 mM 3-(N-morpholino) propanesulphonic acid, pH 7.0, 8 mM sodium acetate, 1 mM EDTA) at 65° C. for 15 minutes, and cooled on ice. Gels were electrophoresed in MOPS buffer, and blotted onto Duralon membranes by capillary transfer as described in Sambrook et al., (1989).

Preparation of Southern Blots

Two gm of adult *Haemonchus contortus* which had been snap-frozen in liquid nitrogen were ground to a fine powder in liquid nitrogen. The powder was added slowly to 25 ml of lysis buffer (0.05M Tris-HCl, pH 8, 0.1% EDTA, 1% w/v Sarkosyl, 0.05 mg/ml proteinase K (Boehringer Mannheim)) and incubated for two hours at 65° C. The suspension was then extracted twice with one volume of phenol plus chloroform, twice with two volumes of chloroform, and ethanol precipitated. The precipitated genomic DNA was resuspended in 20 ml of Tris, EDTA buffer (TE, pH 8) overnight at 4° C. on a rocking table, then dialysed against two changes of one liter of TE. RNA was removed by incubating with DNase-free RNase A type 1 (Sigma) at a final concentration of 20 μg/ml, at 37° C. for one hour, followed by one extraction with phenol-chloroform, one extraction with chloroform, and ethanol precipitation, as above. The precipitated genomic DNA pellet was washed twice with 70% v/v ethanol, and resuspended in one ml TE, as above.

Genomic DNA was digested with EcoRI or HindIII (25 μg of DNA in each digest) overnight at 37° C., then electrophoresed at 5 μg per track on a 1% w/v agarose gel in Tris-acetate buffer. The gel was Southern blotted by capillary transfer as described in Maniatis et al., (1982) onto Hybond-N membrane (Amersham International). DNA was fixed onto the membrane using ultraviolet light, according to the manufacturer's recommendations.

Preparation of Probes pBLUESCRIPT plasmids containing the M1AUS, B1A or AustB1 inserts were digested with EcoR1. pT7Blue plasmids containing 3.5 kb PCR product inserts were digested with BamH1 and those containing 2.5 kb PCR product inserts were digested with BamH1 and Xba1. Digests were electrophoresed, the inserts recovered and radioactively labelled with α-$^{32}$P-dCTP by nick translation as described above under screening of the λZAP library.

Hybridization Conditions

For Southern Blots

The membranes were cut into strips and prehybridised in hybridisation buffer as described earlier for 3 hours at 28° C. Genomic DNA Southern blot strips were hybridised to each of the above probes overnight at 28° C., washed twice at room temperature (24° C.) then twice at 42° C., in 2× SSC containing 0.1% w/v SDS (moderate stringency) and autoradiographed. Following development of the autoradiographs, strips were re-washed at a high stringency (0.1× SSC, 0.1% w/v SDS at 65° C.) and re-autoradiographed.

For Northern Blots

For probes M1, M1AUS and B1A (SEQ ID NOS:1, 5 and 2 respectively)

The Northern blot of mRNA from 11, 15 and 23 day-old *Haemonchus contortus* was probed first with the M1 insert. The filter was prehybridised for 2 hours at 42° C. in 2× SSC (where 20× SSC=3M NaCl, 0.3M sodium citrate, pH 7.2) containing 5× Denhardt's (0.1% w/v Ficoll 400 (Pharmacia), 0.1% polyvinylpyrrolidone, 0.1% bovine serum albumin Fraction V (Sigma Chemical Corp)), 0.5% SDS (sodium dodecylsulphate), 10% dextran sulphate, 0.1 mg/ml salmon testes DNA and 50% de-ionised formamide. The hybridisation to the probe was performed in the same buffer overnight at 42° C. The filters were washed twice for 30 minutes in 2× SSC containing 0.5% SDS and 50% formamide, twice for 30 minutes in 2× SSC containing 0.5% SDS and twice for 30 minutes in 2× SSC. The first wash was at 42° C. and all remaining washes were at 37° C. After autoradiography the blot was stripped by washing in boiling 0.1% SDS and re-autoradiographed to ensure removal of the probe. The same blot was then probed with the M1AUS insert, washed and autoradiographed. The blot was again stripped and checked and when clear was then probed with the B1A insert. After stripped again the blot was then probed as described below.

For probes AustB1, 2.5 kb and 3.5 kb PCT products (SEQ ID NOS:6, 7 and 8)

The Northern blot was hybridised with the AustB1 insert using the conditions of moderate stringency as described for Southern blot hybridisation. After autoradiography the blot was stripped with boiling 0.1% SDS according to the membrane manufacturer's instructions (Amersham), then probed with the 2.5 kb PCR insert (clone 2), stripped again and probed with the 3.5 kb PCR (clone 2) insert.

Digestion of H110D and Assays of Enzyme Activity

Preparation of H110D

Native H110D (H110DN) was prepared according to the methods described in WO 88/00835 and WO 90/11086.

Preparation of an Elastase Fragment (H11S) of H110D

Adult Haemonchus were homogenized in 10 volumes of ice cold PBS/0.02% sodium azide and then centrifuged for 20 minutes at 13000 rpm. The pellet was resuspended in 10 volumes of PBS/azide, rehomogenised and the centrifugation repeated. Following resuspension in 50 mM MOPS buffer pH 7.4 (the volume for suspension is 1 ml for each 0.17 g of worms) and pre-warming at 37° C. for 30 minutes, the pellet material was digested with elastase (800 μl/20 ml of suspension; 1 mg/ml fresh stock solution made up in 1 mM HCl/2 mM Ca$^{2+}$) for one hour. The digestion was stopped by the addition of 3,4 dichloroisocoumarin (300 μl of stock 10 mM in DMSO/20 ml of digest). The mixture was centrifuged at 13000 rpm for 20 minutes and the pelleted material retained. The supernatant was ultracentrifuged at 100000 g for 1 hour 20 minutes. The resultant supernatant liquid was applied to a ConA column and the binding fractions obtained. For analysis, this fraction was run on an SDS-polyacrylamide gel and electrophoretically transferred to polyvinylidene difluoride membrane (Immobilon-P, Millipore), lightly stained with Coomassie blue, the 105 kd band excised and analysed in a gas phase amino acid sequenator. For vaccination studies, the ConA binding fractions were further purified by concentrating and applying to a Superose 12 (Pharmacia) gel filtration column and collecting those fractions containing aminopeptidase activity.

Thermolysin Digestion of H110D

The H110D doublet was purified by electroelution from a preparative scale 8% SDS-polyacrylamide gel to give H110DE, as described in WO 90/11086 and by electroelution of a dimeric form, running at just over 200 kd (which yielded the characteristic doublet at 110 kd when re-run on SDS-PAGE) to give H110DE. Solutions of H110DE were concentrated to 200 μl, calcium chloride was added to 5 mM and the mixture warmed to 37° C. A freshly prepared solution of 1 mg/ml Thermolysin (in 1 mM HCl, 2 mM CaCl$_2$) was added in a ratio of 0.1 μg Thermolysin per μg H110DE. The mixture was incubated at 37° C. for 120 minutes and the reaction then stopped by addition of 5 μl of 0.5M EDTA.

The protein fragments were separated by 15% SDS-polyacrylamide gel electrophoresis and electrophoretically transferred to polyvinylidene difluoride membrane (Immobilon-P, Millipore). Following staining with Coomassie blue the most intense discrete bands were excised and analysed in a gas phase amino acid sequenator.

Preparation of an H110D fraction (H11A) Enriched for Aminopeptidase A Activity

The pelleted material obtained after elastase treatment by centrifugation at 17000 g for 20 min. (see above) was resuspended in PBS at 4° C. and repelleted by centrifugation then resuspended in 1% Tween in PBS/azide and left (with stirring) for 1 hour. The suspension was centrifuged at 17,000 g for 20 minutes and the supernatant removed. The pellet was repeatedly extracted with 1% Thesit in PBS/azide. The supernatants after centrifugation at 17,000 g for 20 minutes were combined and ultracentrifuged for 1 hour 20 minutes at 100,000 g. The supernatant was applied to a ConA affinity column (Affigel, Biorad) and the bound material eluted and further fractionated by ion exchange chromatography on a MonoQ column.

Assays of Enzyme Activities

α-amino acylpeptide hydrolase (microsomal) aminopeptidase activities in H110D preparations were characterised by assays, in solution, using L-leucine, methionine, phenylalanine, α-glutamic acid and lysine p-nitroanilides (pNA). All the amino acid p-nitroanilide substrates (except α-glutamic acid) were obtained from Sigma, Poole, Dorset UK, α-glutamic acid was from Fluka, Dorset, UK. Single hydrophobic (leucine- or phenylalanine-) and charged (α-glutamic acid-) amino acid pNA known to be substrates for mammalian aminopeptidase-M (ApM) and -A (ApA) respectively, were chosen to measure the effect of enzyme inhibitors and serum inhibition on H110D aminopeptidase activities.

(a) Microplate assay

Micro-ELISA plate (Cynatech Immulon 1, Virginia, USA) wells were each filled with 250 μl of either 50 mM HEPES or MOPS pH 7 plus 1–10 μl of the fraction to be assayed. The plates were then pre-incubated at 37° C. for 10 minutes prior to the addition of 10 μl of 25 mM amino acid p-nitroanilide substrate per well. The time zero optical density (OD) at 405 nm was then measured using an ELISA plate reader and the plates were then incubated at 37° C. for 15–30 minutes. The final OD reading was then taken as before and the OD change per minute per milligram of protein calculated.

(b) Inhibitor sensitivity

The method used for the enzyme assay was as described in (a) above except that the inhibitors were added to the 250 μl of buffer plus 10 μl of 1 mg/ml ConA H110D and pre-incubated for 10 minutes at 37° C. prior to addition of the substrates (leucine-pNA or α-glutamic acid-pNA). The percentage inhibition was calculated as follows $$\frac{x - y}{x} \times 100 = \text{percentage inhibition}.$$

Where x=the ΔOD/min of the enzyme with no inhibitor added and y=ΔOD/min of the enzyme plus inhibitor. Nine compounds with differing enzyme class inhibition were tested individually: Amastatin, Bestatin (metalloprotease, aminopeptidase), 1,10 phenanthroline, EDTA (metalloprotease), phosphoramidon (metalloprotease, thermolysin, collagenase), Aprotinin (serine protease), Pepstatin (aspartic protease), PMSF (serine and cysteine protease) and E64 (cysteine protease). Amastatin, bestatin, 1,10 phenanthroline, PMSF and pepstatin were obtained from Sigma, Dorset, UK. All the other inhibitors were obtained from Boehringer-Mannheim. Each inhibitor was used at two concentrations equal to or greater than the maximum concentrations recommended by Boehringer-Mannheim.

(c) Assay of antiserum inhibition of enzyme

The assay was as described in (a) above except that two micro-ELISA plates were set up. In one plate 10 μl of ConA H110D (1 mg/ml) plus 10 μl of antiserum from each sheep per well were pre-incubated at 37° C. for 15 minutes. The second plate, with 250 μl of HEPES/bicarbonate buffer plus 10 μl of either phenylalanine-pNA or α-glutamic acid-pNA substrate per well was also pre-incubated at 37° C. for 15 minutes. The ConA H110D-serum mixtures were then added to the buffer-substrate mixtures in the second plate with a multi-pipette. The ΔOD/min was determined. For the purposes of the correlations, percentage inhibition was calculated using the formula in (b) above where x represents the mean ΔOD/min for the wells which contained enzyme plus serum from negative control sheep (vaccinated with horse spleen ferritin) and y=the ΔOD/min for the wells which contained enzyme plus sera from individual sheep vaccinated with H110D. For the purposes of the correlations (FIG. 18), the percentage protection was calculated using the formula in (b) above where x=either the average faecal egg output per gram or the average worm burden of the controls, and y=either the faecal output per gram during the experiment or the worm burden of the individual sheep vaccinated with H110D.

Localisation of Enzyme Activity by Histochemistry

Aminopeptidase activity was demonstrated on 10 μm cryostat sections of adult *Haemonchus contortus* using L-leucine 4-methoxy-β-naphthylamide and L-glutamic α-4-methoxy-β-naphthylamide as substrates by the methods of Nachlas et al. (1957), Nakane et al. (1974) and Lojda et al. (1980).

Expression of Recombinant H110D in the Eukaryotic Baculovirus-Insect Cell System Construction of Expression Plasmids The 3.5K PCR fragments described above, were generated by amplification between an oligo dT adaptor (which contained a SalI site) and oligo 872, which represents base no.'s 30–49 in the M1AUS sequence, and were cloned in the pT7Blue vector. Clone pT73.5-2 is oriented with the vector polylinker BamHI site at its 5' end and the HindIII, XbaI and SalI sites at the 3' end. The sequence at the 5' end is (SEQ ID NO:66):

```
    BamHI      *!-----oligo 872-----------!--3.5K------
5'  GG ATC CGA TTG CTG AAT CTA ACT CCA ATC C .......3'
                   Leu Asn Leu Thr Pro Ile .........
```

The asterisk indicates the 3' dT/dA overhand used for cloning in the pT7 Blue Vector.

The 3.5 PCR clone 2 was digested with HindIII (single site in the vector polylinker sequence at the 3' end of the 3.5K gene) and the ends filled in with deoxynucleotides using DNA polymerase I (Klenow fragment), according to Maniatis et al (1982). A BamHI linker (5' CGGATCCG 3' (SEQ ID NO:68)), New England Biolabs Catalog no. 1021) was ligated to the blunt ends, and clones with an extra BamHI site, allowing a full-length H110D gene sequence to be excised as a BamHI fragment, selected. The BamHI fragment was isolated by electrophoresis on a 0.6% w/v agarose gel in tris-acetate buffer, followed by purification using GENECLEAN (BIO101); this procedure was carried out twice. The purified fragment was then ligated to BamHI-cut, phosphatased pBlueBac II (Invitrogen Corp.), and clones carrying the fragment in the correct orientation (ie. with the 5' end of 3.5 PCR clone 2 placed under control of the baculovirus polyhedrin promoter) determined by digestion with NheI and XbaI. The resultant plasmid was partially digested with BamHI and the ends filled in as described above. An NcoI linker containing an ATG (5'CCCATGGG 3' (SEQ ID NO:69); New England Biolabs Catalog no. 1040) was added and the mixture ligated. Clones which had the linker ligated at the 5' end BamHI site of 3.5 PCR clone 2 rather than the 3' site, were determined by digestion with NcoI. The resultant plasmid, designated pBB3.5-2(N), is depicted diagrammatically in FIG. 19.

This construction results in the insertion of an in-frame ATG at the 5' end of the 3.5 PCR clone 2 insert, to initiate translation. The sequence surrounding this initiating ATG (SEQ ID NO:70) is:

```
   BamHI--NcoI link-BamHI----*!-----oligo 872-----------
!--
5'GGATCCCC ATG GGG ATC CGA TTG CTG AAT CTA ACT CCA ATC
C..
          Met Gly Ile Arg Leu Leu Asn Leu Thr Pro Ile
...
```

The expressed protein will be missing amino acids 2–9 of the corresponding H110D sequence, and will have 3 amino acids of linker sequence immediately following the ATG.

Generation of Recombinant Baculovirus Containing H110D Sequences

The plasmid pBB3.5-2(N) was transfected into *Spodoptera frugiperda* (Sf9) cells (obtainable from Invitrogen Corp), using linear *Autographica californica* nuclear polyhedrosis virus (ACNPV) DNA and cationic liposomes (Invitrogen Corp. transfection module), according to the manufacturer's instructions. Cells were cultured in TC-100 medium (SIGMA) supplemented with foetal calf serum (CSL Ltd; heat-inactivated at 56° C. for 45 minutes) and antibiotics (penicillin/streptomycin, gentamycin; CSL Ltd). A control transfection, using a pBB3.5-2 (N) plasmid with the ATG inserted at the 3' end of the 3.5 PCR clone 2 sequence, was also carried out. Recombinant plaques were selected on the basis that the pBlueBac II vector also encodes *E. coli* β-galactosidase (β-gal), by including X-gal in the agarose overlay at the recommended level. A selection of blue plaques were picked and subjected to two further rounds of plaque purification, after which time infected monolayers showed no evidence of contaminating wild-type virus (which would be evidenced by the presence of nuclear polyhedra). Purified viruses were designated 3.5-2-P2A, -P3A and -P4A, and were amplified be two sequential infections of Sf9 cells before use. A plaque purified from the control transfection was designated 3.5-2-rev.

Assessment of H110D Expression in Insect Cells Infected with Recombinant Baculovirus Monolayers of Sf9 cells ($1 \times 10^6$ cells in 25 cm² bottles) were infected with the 3.5-2 viruses, with wild-type (wt) virus, with a control virus expressing β-gal, or were not infected. After four days growth at 26° C., monolayers were detached by gentle shaking, the cells recovered by centrifugation (2000 rpm, 10 minutes), and the cell pellets disrupted by three cycles of freeze-thawing. The lysates were resuspended in 500 μl PBS, and 25 μl aliquots assayed for ApM activity by the micro-well assay.

15 μl aliquots ($3 \times 10^4$ cell equivalents) of the above lysates were electrophoresed on denaturing 7.5% SDS-polyacrylamide gels. One gel was then stained with Coomassie blue to assess levels of expression. The other gel was Western blotted, and the blot probed with anti-H110DN (as described earlier).

RESULTS

Analysis of Immunopositive Clones
Analysis of Antibodies Affinity Purified on Clone M1

Affinity-purified antibodies specific for each of the 5 antibody-positive clones were prepared and used to probe a Western blot of H110D-enriched extract. As shown in FIG. 8, all 5 clones appeared to recognise the H110D doublet. However, the reaction with clone M1 gave the strongest signal (FIG. 8*d*) compared to the λgt11 negative control blot (FIG. 8*e*). This clone was therefore investigated further.

Northern Blot Analysis with Clone M1

Northern blot analysis of *Haemonchus contortus* mRNA probed with the M1 insert is shown in FIG. 9. A single mRNA band was recognised, at approximately 3.5 kb. This is of sufficient size to code for a protein of about 110 kd.

Sequence Analysis of Clone M1

Analysis of restriction digests of the DNA with EcoR1 showed the M1 insert to be approximately 300 bp. The DNA sequence of the M1 fragment was determined (SEQ ID NO:1) and is shown in FIG. 3. The fragment comprises 295 bp with an open reading frame starting at base number 3.

Northern Blot Analysis with Clone B1A

Northern blot analysis of *Haemonchus contortus* mRNA probed with the B1A insert is shown in FIG. 9*c*. As for M1, a single mRNA band was recognised, at approximately 3.5 kb.

Sequencing of Clones B1A and B2

Clones of B1A were sequenced (SEQ ID NOS:2 and 3) and the full sequence (SEQ ID NO:2) is shown aligned to H11-1 (SEQ ID NO:19) and AustB1 (SEQ ID NO:6) in FIG. 5. The insert is 484 bp and has a full ORF from the first base. The 3 fragments of B2 resulting from digestion with EcoR1 were sequenced and the complete sequence for B2 (SEQ ID NO:4) is 581 bp. It is shown aligned with H11-2 in FIG. 4. The sequence has an ORF from position 3 to 213 bp, the stop codon and untranslated region matching that of the 2.5 kb PCR product sequence (SEQ ID NO:7).

Expression of M1 and B1A in *E. coli*

When subcloned into a GST expression vector, clones were obtained which expressed fusion proteins of 38–40 kd for M1 and of 45 kd for B1A. These agree with the predicted sizes for these inserts, allowing for the molecular weight of glutathione-S-transferase. Both fusion proteins reacted very strongly on Western blots with affinity-purified antibodies to H110DE (FIG. 11). The fusion proteins were expressed as insoluble inclusion bodies.

Antibody Responses in Sheep Vaccinated with M1-GST and B1A-GST Fusion Proteins

Antisera from sheep injected with the fusion proteins were tested by Western blotting against H110D preparations. Both GST-M1 and GST-B1A raised antibodies which specifically recognised the H110D doublet (FIG. 12). Sera from negative control sheep did not recognise the H110D doublet.

Isolation and Characterisation of Clones Selected By Hybridisation with M1 or B1A Insert DNA The confirmed positive clone hybridising to the M1 probe was designated M1AUS (SEQ ID NO:5), a d the clone hybridising the B1A was designated AustB1 (SEQ ID NO:6). Restriction digestion of purified plasmid DNAs with EcoRI indicated an insert size of about 900 bp for M1AUS and of about 1.6 Kb for AustB1. As shown in FIG. 9b) and 9d), on Northern blots, M1AUS and AustB1 hybridised to the same-sized mRNA (about 3.5 kb) as did M1 and B1A.

Sequence Analysis of M1AUS

Full sequencing of the M1AUS fragment was carried out using synthetic oligonucleotides to "walk" along the DNA from either end. Analysis of the sequence obtained revealed that the M1AUS insert was 948 bp, as shown in FIG. 3. The sequence (SEQ ID NO:5) begins with an ATG (which codes for methionine) and has an open reading frame (ORF) over the whole of its length. The sequence is 19 base pairs longer than the M1 sequence at the 5' end, and 634 bp longer at the 3' end. The sequence common to the two clones (bases 20 to 314) were identical except for two nucleotide differences in a third codon position. Comparison of all possible reading frames to various databases showed that the reading frame starting with the ATG at base number one shared homology with the members of a family of microsomal aminopeptidases.

Sequence of AustB1

Full sequencing of the AustB1 fragment was carried out using synthetic oligonucleotides to "walk" along the DNA from either end. The DNA sequence (SEQ ID NO:6) is shown in FIG. 5. The clone is 1689 bp long and has an ORF from residue 2. This sequence forms part of H11-1 as shown in FIG. 1. The amino acid translation of this sequence showed the zinc binding site motif characteristic of aminopeptidases.

PCR Amplification of the cDNA of the H110D mRNAs PCR Using M1 AUS Primers cDNA was synthesized from *Haemonchus contortus* mRNA using as primer oligo-dT containing an adaptor sequence to facilitate subsequent cloning and manipulation of the DNA. The cDNA was then used to amplify the M1AUS sequence by PCR, using as the 5' and primer a synthetic oligonucleotide based on positions 765–885. A PCR fragment of about 2.5 Kb was amplified. This is approximately the expected size of the fragment, based on the known size of the mRNA and on mammalian aminopeptidase cDNA sequences.

A second set of PCR reactions was performed using a primer near the 5' end of M1AUS (bases 30–49). Four bands were detected on an agarose gel. The largest of these, at 3.5 kb, corresponds to the predicted size for the PCR product.

Cloning and Sequencing of 2.5 kb and 3.5 kb PCR Products from M1AUS Primers

The 2.5 kb and 3.5 kb PCR products were cloned and designated 2.5 PCR (SEQ ID NO:7) and 3.5 PCR (SEQ ID NOS:8, 14 and 15 for clone numbers 2, 10 and 19 respectively). On Northern blots 2.5 PCR and 3.5 PCR (clone 2, 3.5 PCR-2) hybridised with mRNA of about 3.5 kb (FIG. 9e, f) in the same pattern (with respect to age of Haemonchus used to obtain the mRNA) as M1, B1A, M1AUS and AustB1.

Full sequencing of clones was carried out by 'oligonucleotide walking'. As shown in FIG. 1, the sequence for the 2.5 kb product (SEQ ID NO:7) is part of H11-2 (SEQ ID NO:20) and the sequence for the 3.5 kb product (SEQ ID NO:8) is the major part of H11-3 (SEQ ID NO:21). The amino acid translations of both these sequences (shown in FIG. 6) contain the zinc binding motif (SEQ ID NO:72) His Glu Xaa Xaa His Xaa Trp (HEXXHXW) characteristic of microsomal aminopeptidases.

Sequencing of 5' end PCR Clones cDNA was synthesised using a primer matching a conserved sequence in cDNA clone AustB1, 2.5 PCR and 3.5 PCR (SEQ ID NOS:6, 7 and 8) which hybridises with the mRNA for these sequences about 1.3 Kb from the 5' end. The cDNAs were C-tailed at the 5' end and then PCR reactions carried out with a universal Anchor (A) primer for the 5' end and three primers specific for each of the sequences AUSTB1, 2.5 PCR and 3.5 PCR-Clone 2 (SEQ ID NOS:6, 7, 8) for the 3' end. The reactions each gave a product of the predicted size, just under 1.3 kb: 1301 bp (SEQ ID NO:9), 1280 bp (SEQ ID NO:10) and 1292 (SEQ ID NO:11) respectively. All three sequences have an untranslated region at the 5' end (FIG. 2). All begin with the same 22 bp sequence (5' GGTTTAATTAC-CCAAGTTTGAG 3' (SEQ ID NO:73)) which is known as the Spliced Leader Sequence 1 (SL1) and is present in the untranslated 5' region of a wide variety of nematodes Huang et al., 1990. In SEQ ID NOS:9 and 10, the SL1 sequence is immediately before the initiating ATG. In SEQ ID NO:11 there are 13 bp between the SL1 and the initiating ATG. All three sequences have full ORFs.

Sequencing of AustB1 3' End PCR Clone

Using a specific primer matching positions 1414–1438 in Aust B1 (SEQ ID NO:6), the PCR product gave a band as predicted of about 1.3 kb. Sequencing of the cloned band yielded the sequences SEQ ID NOS:12 and 13. They gave an ORF from 1–615 bp and a substantial untranslated region.

Sequence Analysis of Cloned PCR Products

Composites of the sequences described above, designated H11-1, H11-2 and H11-3, are shown in FIG. 2. The amino acid sequences predicted from these are shown in FIG. 6a. The validity of the predicted translations of the DNA sequences presented is substantially confirmed by the matches with amino acid sequences determined by Edman degradation from CNBr and proteolytic cleavage fragments (FIG. 7). Thus 27 residues of the 29 residue N-terminal sequence of H11S (SEQ ID NO:16) match H11-2 from residues 61–90 (FIG. 7b). The matches of valine (V) at position 78 and glycine (G) at position 90 are characteristic of H11-2 since H11-3 has asparagine (N) at position 90 and H11-1 has leucine (L) at position 86 (which corresponds to position 78 in H11-2). Two residues of the H11S N-terminus amino acid sequence (SEQ ID NO:16) do not match any of the three H110D sequences presented here. To be particularly noted are the exact matches of the very similar, but distinctive sequences Pep A and B (previously described in WO 90/11086) with H11-2 and H11-1 respectively in the region of residues 540–555. Similarly in the 450–470 residue region, Pep D is an exact match for H11-2, while the similar but distinct Pep E matches more closely H11-3.

By way of example the translated amino acid sequence of one of the full-length sequences (H11-3) is compared in FIG. 6b with two sequences for mammalian microsomal aminopeptidases. The homology of the H110D translation with these aminopeptidases is shown by boxing identical amino acids. A characteristic motif of microsomal aminopeptidases is the amino acid sequence HEXXHXW, which functions as the zinc binding site (Jongeneel et al., 1989; Vallee et al., 1990); this is shown by asterisks in FIG. 6. This sequence, which is shown to be present in the translations of H11-1, H11-2 and H11-3, is conserved in all the microsomal aminopeptidases. Other features common to the mammalian and Haemonchus microsomal aminopeptidases are the presence of a comparatively short intracellular region, a single transmembrane sequence adjacent to the N-terminus and several potential glycosylation sites. The levels of homology (similarities of 52–55% and identities of 30–32%) of H11-1, -2 and -3 to mammalian microsomal aminopeptidases are shown in Table 2.

Southern Blot Analyses

The results of *H. contortus* genomic DNA Southern blots probed with various H110D cDNA clones and PCR products are shown in FIG. 10. All probes show multiple bands of hybridisation; this typical of a multigene family. As expected, B1A and AustB1 showed similar hybridisation patterns to each other, as did M1AUS and 3.5 kb PCR. However, these patterns were noticeably different from each other and from that seen with the 2.5 Kb PCR probe, even under conditions of moderate stringency (FIG. 10A), reflecting the differing levels of homology between these three cDNAs.

Demonstration of Aminopeptidase Activities Associated with H110D

Microsomal aminopeptidase activity was found to associate with those fractions containing H110D, that is the supernatants from ultracentrifugation of Thesit extracts, ConA binding fraction (ConA H110D) and the fractions containing H110D obtained by ion exchange chromatography on a MonoQ column (Table 3). The specific activities with all substrates tested increased as the purity of the H110D increased.

TABLE 3

ENZYME ACTIVITIES OF FRACTIONS
FROM A TYPICAL H110D PREPARATION

SPECIFIC ENZYME ACTIVITIES (O.D./minute/mg protein)

| FRACTION | Phenyl-alanine-pNA | Leucine-pNA | Lysine-pNA | α-Glutamic acid-pNA | Methionine-pNA |
|---|---|---|---|---|---|
| Phosphate buffered saline (PBS) | 0.20 | 0.08 | 0.12 | 0.01 | 0.16 |
| 1% Tween 20/PBS | 0.15 | 0.15 | 0.09 | 0.01 | 0.09 |
| 1% Thesit/PBS | 1.94 | 1.25 | 0.57 | 0.54 | 1.91 |
| ConA H110D | 4.08 | 3.01 | 1.43 | 2.09 | 3.84 |
| CamQ H110D | 6.55 | 5.01 | 3.01 | 3.90 | 6.41 |

Effects of Inhibitors of Mammalian Aminopeptidases on H110D Aminopeptidase Activities Addition of the inhibitor bestatin (which inhibits mammalian microsomal aminopeptidase) to ConA H110D at the concentration recommended by the supplier (Boehringer Mannheim) reduced the activity against leucine-p-nitroanilide by approximately 70%. A series of experiments were performed to test inhibition of activity by a range of protease inhibitors. Those inhibitors which were not specific for metalloproteases or aminopeptidases had no inhibitory effects on the reaction rate. Inhibitors that are known to affect metalloproteases or aminopeptidases did have an effect on reaction rates, as shown in Table 4. The most effective inhibitor was 5 mM phenanthroline.

TABLE 4

Inhibition of H110D aminopeptidase activities using various protease inhibitors

| INHIBITOR | CONCEN-TRATION | PERCENTAGE INHIBITION α-glutamic acid-p-nitroanilide substrate[1] | PERCENTAGE INHIBITION Leucine-p-nitroanilide substrate[2] |
|---|---|---|---|
| Amastatin | 10 µM | 0 | 61 |
|  | 50 µM | 0 | 66 |
| Bestatin | 50 µM | 23 | 63 |
|  | 100 µM | 35 | 68 |
| EDTA | 1 mM | 17 | 8 |
|  | 10 mM | 21 | 16 |
| 1,10 phenanthroline | 1 mM | 78 | 78 |
|  | 10 mM | 85 | 87 |
| Phosphoramidon | 10 µM | 1 | 0.8 |
|  | 50 µM | 1 | 7 |

[1]A mammalian aminopeptidase-A substrate.
[2]A mammalian aminopeptidase-M substrate.

Sub-Fractionation of H110D

Figure 13B:
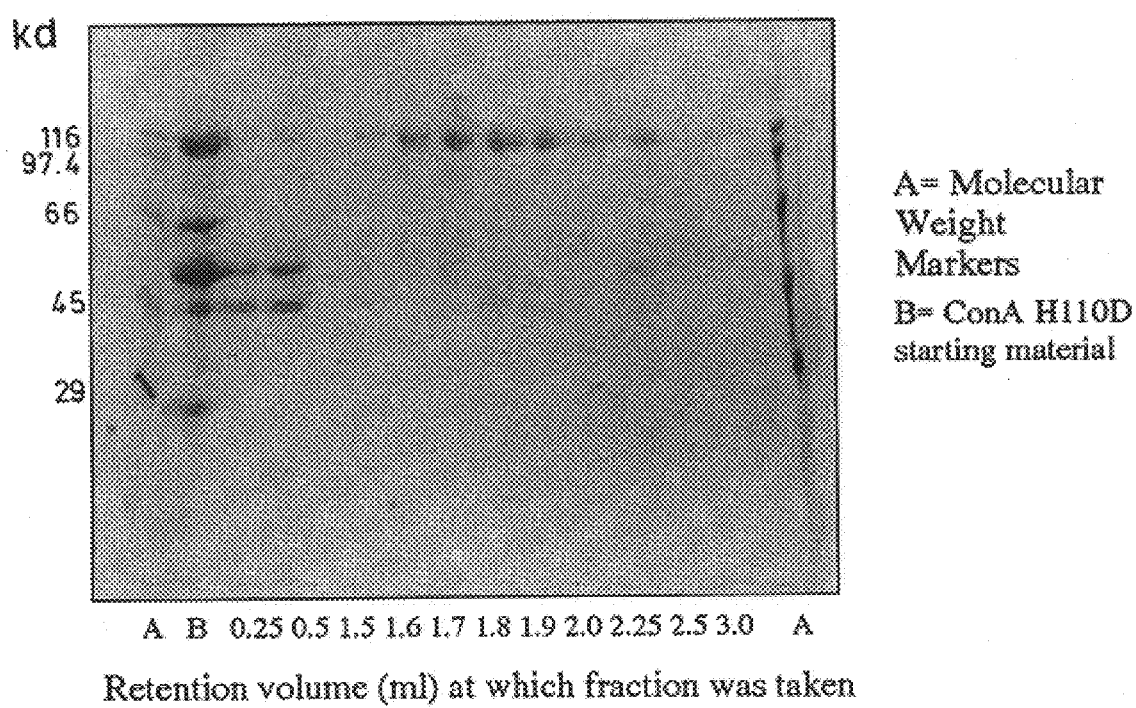

The distribution of activities associated with fractions from ion exchange chromatography of ConAH110D on MonoQ are shown in FIG. 13a and SDS-PAGE of the fractions in FIG. 13b.

Figure 15C:
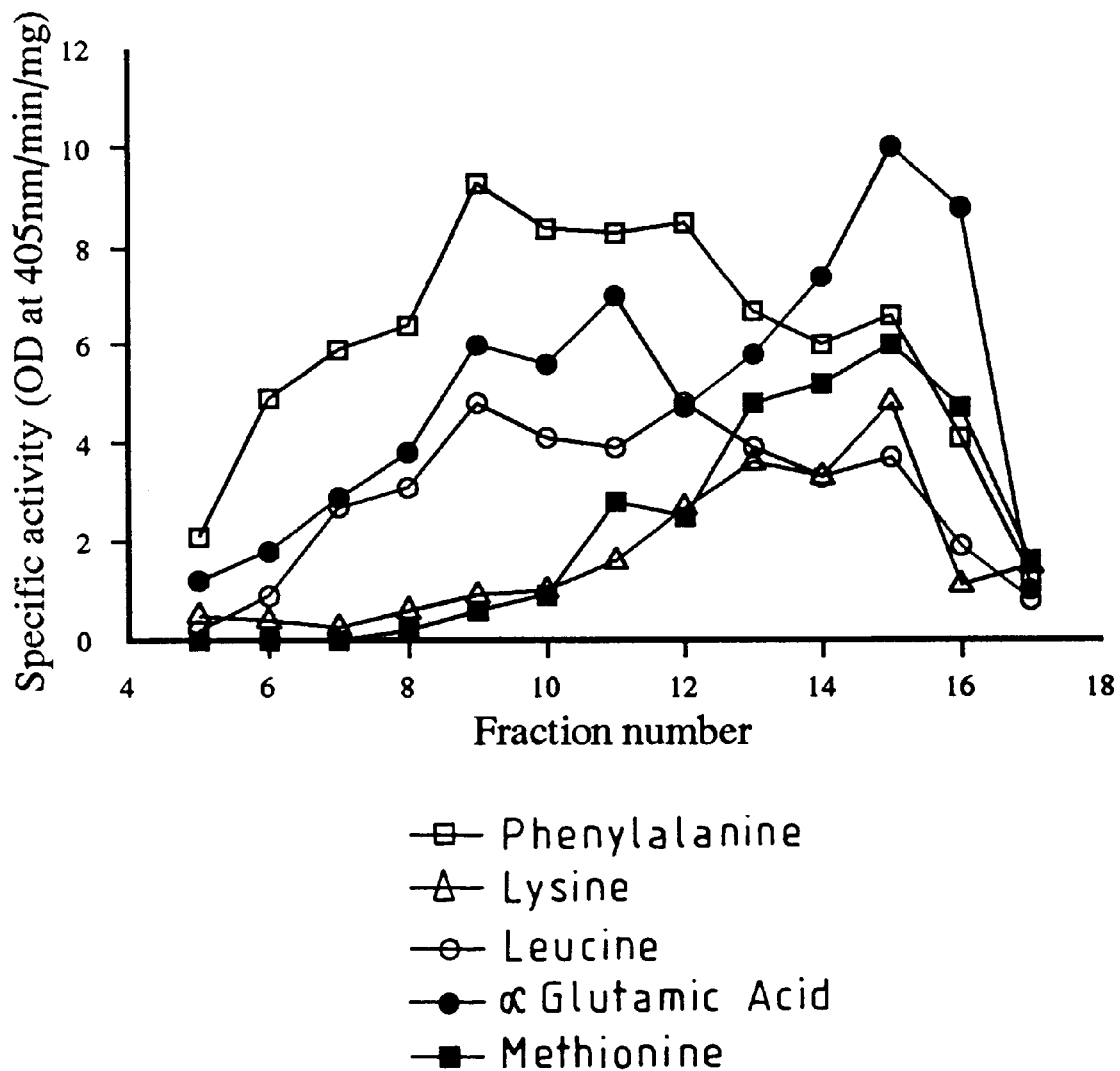

Further, enzymatic activity was associated with sub-fractions of H110D separated by re-cycling free flow iso-electric focussing (FIGS. 14 and 15). At lower pI values (pH 4.5) these sub-fractions contain only the larger of the bands which make up the H110D doublet seen on SDS-PAGE and at higher values (pH 6.5) they contain only the smaller of bands which make up the H110D doublet. Intermediate fractions contain both these bands. The smaller band may also be obtained as a separate fraction by ion exchange chromatography on MonoQ using the Pharmacia SMART[R] apparatus. All these sub-fractions bind sheep antibodies to H110D affinity purified on the protein expressed by the λgt11 clone M1 whereas antibodies eluted from λgt11 with no insert do not bind (FIG. 14c). All the sub-fractions bind mouse monoclonal antibodies designated TS 3/19.7 (FIG. 14c) which also bind to the recombinant protein expressed by clone M1. All the sub-fractions show microsomal aminopeptidase activity (FIG. 15c) although this activity is comparatively low in the fractions obtained at the highest and lowest pIs. This lower activity may be attributed to lowered protein concentrations, effects of extremes of pH during sub-fractionation or a requirement for the presence of both larger and smaller bands for maximal activity.

Vaccination with Separated Components of H110D

The separated upper and lower bands obtained by free flow isoelectric focussing or by ion exchange chromatography induce the formation of protective antibodies when injected into sheep as exemplified in the following experiment. Thirty sheep approximately six months old were assigned to 5 groups of 6 so that each group was matched for range of weights of sheep. Each animal was injected with a total of 150 µg protein given in 3 equal doses as described in Munn et al. (1992) and Tavernor et al. (1992a, b) over a period of 54 days. The animals in group L were injected with the lower (smaller) band of the H110 Doublet, those in group U with the upper band, U+L with recombined upper and lower bands, D with the two (unseparated) bands obtained by free-flow isoelectric focussing at intermediate pH values and as a control (group C) horse spleen ferritin (an antigenic unrelated protein). The sheep were challenged with 10,000 infective larvae three weeks after the third injection and the experiment terminated 29–31 days post infection. The outcome of the experiment is summarised in FIG. 16. Injection of any of the sub-fractions reduced parasite egg output throughout the trial by some 90% and reduced total worm numbers by 63–84%, all showing a significant difference ($p<0.05$) to the controls using non-parametric statistical analyses. Reductions (70–88%) in the numbers of female worms were greater than the reductions in the numbers of male worms, and (except for the reduction in male worm numbers in the sheep injected with the recombined upper and lower bands where $p<0.07$) for both sexes the reductions were significant ($p<0.05$).

Vaccination with H11S and H11A

A truncated, water-soluble form of H110D (H11S; which retains its enzymic activity) may be obtained from the native molecule by treatment with elastase. This form was found to contain predominantly ApM-like enzyme activity and a Thesit extract of the elastase digested pellet (H11A) was enriched for ApA-like activity (see Table 5).

TABLE 5

| Ratio Aminopeptidase-M:Aminopeptidase-A | |
|---|---|
| (leucine-pNA) | (α-glutamic acid-pNA) |
| H110D 1.44:1 | |
| H11S 26.0:1 | |
| H11A 0.48:1 | |

The following experiment shows that vaccination of sheep with either H11S or H11A gives protection against Haemonchus challenge or infection. Eighteen sheep approximately eight months old were assigned to 3 groups of 6 so that each group was matched for range of weights of sheep. Each animal was injected with a total of 100 µg protein given in 2 equal doses as described in Munn et al. (1992) and Tavernor et al. (1992a, b) over a period of 23 days. The animals in group A were injected with H11A, those in group S with H11S and those in group C with horse spleen ferritin (an antigenically unrelated protein) as a negative control. The sheep were then challenged with 10,000 infective larvae 25 days after the second injection and the experiment terminated at 34–36 days post infection. The outcome of the experiment is summarised in FIG. 17. Injection of H11S reduced parasite egg output throughout the trial by 89% and reduced total worm numbers by 76%. Injection of H11A reduced parasite egg output throughout the trial by 98% and reduced total worm numbers by 84%. These showed a significant difference ($p<0.05$) from the controls using non-parametric statistical analyses.

Inhibition of H110D Aminopeptidase Activities By Antibodies

Solutions containing H110D were incubated with sera from individual sheep injected with fractions containing H110D or from control sheep. The solutions were then assayed for aminopeptidase activities using phenylalanine and α-glutamic acid pNAs as substrates. The degree of inhibition of activity (maximally 80%) correlated with the level of protection shown by the individual sheep from which the sera were obtained (see FIG. 18).

Localisation of Enzyme Activity

Frozen sections of adult *Haemonchus contortus* were examined for aminopeptidase activity. As shown in FIG. 19, aminopeptidase enzyme activities are localised to the luminal surface of the intestine. H110D protein is also specifically found in this location.

Expression of H110D (3.5 PCR Clone 2) Using the Eukaryotic Baculovirus-Insect Cell System Expression of Aminopeptidase Activity in Insect Cells Infected cells were harvested and assayed for aminopeptidase activities using phe-, leu-, met- and lys-pNA as substrates. The assay was complicated by the observation that the insect cells possess an aminopeptidase activity with a marked preference for lys-linked amide bonds. However, cell extracts containing the expressed H110D additionally cleaved leu-, met- and phe-pNA in that order of preference.

Molecular Weight and Immunoreactivity of the Expressed H110D (3.5 PCR Clone 2) Protein Samples of infected or control cell extracts were electrophoresed on a 7.5% SDS-polyacrylamide gel, which was then stained with Coomassie Blue. The 3.5-2-P3A and 3.5-2-P4A infected cell lysates both had a band at the same size as H110D, 110 kd, which migrated directly beneath the co-expressed β-gal, which has a molecular weight of 120 kd. This 110 kd band was not present in any of the negative control lysates. (It was also absent from the P2A lysate, which did not express enzyme activity).

A duplicate gel was Western blotted and probed with anti-H110DN (FIG. 21). A very strong, specific positive immunoreaction was obtained to the 110 kd band expressed by 3.5-2-P3A and 3.5-2-P4A, and to the native H110D doublet in a control track containing ConA H110D, while no reaction was seen in any of the negative control tracks.

REFERENCES

Andreason, G. L. & Evans, G. A. (1980) Biotechniques 6, 650.

Blin, N., & Stafford, D. W. (1976). Nucleic Acids Research 3, 2303–2308.

Bowtell, D. D. L., Saint, R. B., Rickard, M. D. & Mitchell, G. F. (1986). Parasitology 93, 599–610.

Chomcyznski, P. & Sacchi, N. (1987). Analytical Biochemistry 162, 156–159.

Cordingley, J. S., Taylor, D. W., Dunne, D. W. & Butterworth, A. E. (1983) Gene 26, 25–39.

Devereux, J., Haerberli, S. & Smithies, O. (1984), Nucleic Acids Research 12, 387–395.

Feinberg, A. P. & Vogelstein, B. (1983). Analytical Biochemistry 132, 6–13.

Fire, A. (1986) EMBO Journal 5, 2673–2680.

Fire, A. & Waterston, R. H. (1989) EMBO Journal 8, 3419–3428.

Francis, M. J. & Clarke, B. E. (1989) Methods in Enzymology 178, 659.

Frohman, M. A., Dush, M. K. and Martin, G. R. (1988). Proceedings of the National Academy of Sciences, Washington 85, 8998–9002.

Gubler, U. & Hoffman, B. J. (1983). Gene 25, 263–265.

Han, M. & Sternberg, P. W. (1990) Cell 63, 921–931.

Huang, X.-Y. & Hirsch, D. (1990) Proceedings of the National Academy of Sciences Washington 86, 8640–8644.

Johnstone, A. and Thorpe, R. (1982) Immunochemistry in Practice. Blackwell Scientific. London Jongeneel, C. V., Bouvier, J. & Bairoch, A. (1989). FEBS Letters 242, 211–214.

Kenny, A. J. & Maroux, S. (1982). Physiological Reviews, 62, 91–128.

Kenny, A. J. & Turner, A. J. (1987). Mammalian Ectoenzymes. Elsevier Press, Amsterdam. Volume 14 of Research Monographs in Cell and Tissue Biology. (editors J. T. Dingle & J. L. Gordon).

Laemmli, U. K. (1970) Nature 227, 680–685.

Lojda, Z. & Gossrau, R. (1980) Histochemistry 67, 267–290.

Maniatis, T., Fritsch, E. F. & Sambrook, J. (1982). Molecular Cloning, a Laboratory Manual. Cold Spring Harbor Laboratory Publication.

Merrifield, R. B. (1964) Biochemistry 3, 1385–1390.

Munn, E. A., Smith T. S., Graham, M., Greenwood, C. A., Tavernor, A. S. & Coetzee, G. (1992) Parasitology 106, 63–66.

Nachlas, M. M., Crawford, C. T. and Seligman, A. M. (1957). J Histochem & Cytochem. 5, 264–278.

Nakane, P. K. & Kawoi, A. K. (1974). Journal of Histochemistry and Cytochemistry, 22, 1084–1091.

Noren, O., Sjostrom, H., Danielsen, E. M., Cowell, G. M. & Skovbjerg, H. (1986). The Enzymes of the Enterocyte Plasma Membrane. In Molecular and Cellular Basis of Digestion. Elsevier Press, Amsterdam, (editors P. Desnuelle, H. Sjostrom & O. Noren).

Sambrook, J., Fritsch, E. F. & Maniatis, T. (1989). Molecular Cloning, a Laboratory Manual, 2nd Edition. Cold Spring Harbor Laboratory Press.

Semenza, G. (1986). Annual Review of Cell Biology, 2, 255–313.

Smith, D. B. & Johnson, K. S. (1988) Gene 67, 31–40.

Spieth, J. MacMorris, M., Broverman, S., Greenspoon, S. & Blumenthal, T. (1988) Dev. Biol. 130, 285–293.

Tavernor, A. S., Smith, T. S. Langford, C. F., Graham, M. & Munn, E. A. (1992a) Parasite Immunol. 14, 671–675.

Tavernor, A. S., Smith, T. S., Langford, C. F., Munn, E. A. & Graham, M. (1992b) Parasite Immunol 14, 645–655.

Vallee, B. L. & Auld, D. S. (1990) Biochemistry 29, 5647–5659.

Watt, V. M. & Yip, C. C. (1989) Journal of Biological Chemistry 264, 5480–5487.

Woodward, M. P., Young, W. W. Jr. and Bloodgood, R. A. (1985). Detection of Monoclonal Antibodies specific for carbohydrate epitopes using periodate oxidation. J. Immunol. Meth. 78, 143–153.

Wu, Q., Lahti, J. M., Air, G. M., Burrows, P. D. & Cooper, M. D. (1990) Proceedings of the National Academy of Sciences, Washington 87, 993–997.

We claim:

1. An isolated nucleic acid molecule which encodes a helminth aminopeptidase comprising at least one nucleotide sequence selected from the group of sequences consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:19, SEQ ID NO:20, SEQ ID NO:21, sequences fully complementary to one of said sequences, portions of said sequences, wherein said portions of said sequences encode an antigenic peptide of said helminth aminopeptidase.

2. An isolated nucleic acid molecule comprising at least one nucleotide sequence encoding a polypeptide capable of raising protective antibodies against helminths, wherein said nucleotide sequence comprises at least one of the aminopeptidase-encoding sequences shown in FIGS. 2, 3, 4 or 5 (SEQ ID NOS:1–15 and 19–21).

3. A method for preparing a synthetic polypeptide comprising the amino acid sequence of an aminopeptidase enzyme wherein the amino acid sequence is encoded by at least one of SEQ ID NO:1–15 or 19–21, portions of said sequences, wherein said portions of said sequences encode an antigenic peptide of said helminth aminopeptidase, and wherein the synthetic polypeptide is not a synthetic polypeptide corresponding to the protein doublet H110D and is not a synthetic polypeptide with a sequence of any one of SEQ ID NO:25–54, wherein the method comprises culturing a prokaryotic or eukaryotic cell containing a nucleic acid molecule as defined in claims 1 or 2, under conditions whereby said synthetic polypeptide is expressed, and recovering said synthetic polypeptide thus produced.

4. The method of claim 3 wherein the synthetic polypeptide is in the form of fusion polypeptide wherein an additional polypeptide is fused to said amino acid sequences.

5. An expression or cloning vector comprising a nucleic acid molecule as defined in claims 1, 2, 3 or 4.

6. An isolated prokaryotic or eukaryotic cell containing a nucleic acid molecule as defined in claims 1, 2, 3 or 4.

* * * * *